US012676231B2

(12) United States Patent
Lefkofsky

(10) Patent No.: US 12,676,231 B2
(45) Date of Patent: Jul. 7, 2026

(54) ARTIFICIAL INTELLIGENCE ASSISTED PRECISION MEDICINE ENHANCEMENTS TO STANDARDIZED LABORATORY DIAGNOSTIC TESTING

(71) Applicant: Tempus AI, Inc., Chicago, IL (US)

(72) Inventor: Eric Lefkofsky, Glencoe, IL (US)

(73) Assignee: Tempus AI, Inc., Chicago, IL (US)

( * ) Notice: Subject to any disclaimer, the term of this patent is extended or adjusted under 35 U.S.C. 154(b) by 984 days.

(21) Appl. No.: 17/076,801

(22) Filed: Oct. 21, 2020

(65) Prior Publication Data

US 2021/0118559 A1 Apr. 22, 2021

Related U.S. Application Data

(60) Provisional application No. 62/924,515, filed on Oct. 22, 2019.

(51) Int. Cl.
| | |
|---|---|
| *G16H 40/20* | (2018.01) |
| *A61B 6/03* | (2006.01) |
| *G16B 15/30* | (2019.01) |
| *G16H 10/40* | (2018.01) |
| *G16H 15/00* | (2018.01) |
| *G16H 30/20* | (2018.01) |
| *G16H 30/40* | (2018.01) |
| *G16H 50/20* | (2018.01) |
| *G16H 50/70* | (2018.01) |

(52) U.S. Cl.
CPC ............. *G16H 40/20* (2018.01); *A61B 6/032* (2013.01); *G16B 15/30* (2019.02); *G16H 10/40* (2018.01); *G16H 15/00* (2018.01); *G16H 30/20* (2018.01); *G16H 30/40* (2018.01); *G16H 50/20* (2018.01); *G16H 50/70* (2018.01)

(58) Field of Classification Search
CPC ........ G16H 40/20; G16H 10/40; G16H 15/00; G16H 30/20; G16H 30/40; G16H 50/20; G16H 50/70; A61B 6/032; A61B 6/037; A61B 6/5217; A61B 6/563; G16B 15/30; G16B 20/00; Y02A 90/10
See application file for complete search history.

(56) References Cited

U.S. PATENT DOCUMENTS

| | | |
|---|---|---|
| 2020/0126663 A1 | 4/2020 | Lucas |
| 2020/0210852 A1 | 7/2020 | Igartua |
| 2020/0211716 A1 | 7/2020 | Lefkofsky |
| 2020/0258223 A1 | 8/2020 | Mp |
| 2020/0273576 A1 | 8/2020 | Lozac'hmeur |
| 2020/0365268 A1 | 11/2020 | Michuda |

OTHER PUBLICATIONS

Li Li et al. ,Identification of type 2 diabetes subgroups through topological analysis of patient similarity.Sci. Transl. Med.7,311ra174-311ra174(2015). DOI:10.1126/scitranslmed.aaa9364 (Year: 2015).*

Mandl, K. D., & Manrai, A. K. (2019). Potential Excessive Testing at Scale: Biomarkers, Genomics, and Machine Learning. JAMA, 321(8), 739-740. https://doi.org/10.1001/jama.2019.0286 (Year: 2019).*

Dash, S., Shakyawar, S.K., Sharma, M. et al. Big data in healthcare: management, analysis and future prospects. J Big Data 6, 54 (2019). https://doi.org/10.1186/s40537-019-0217-0 (Year: 2019).*

Adithi Gandhi and Jeemin Kwon, What's a 'Normal' A1C? When is it Misleading?. diaTribe Learn Making Sense of Diabetes 2017. https://web.archive.org/web/20191215211352/https://diatribe.org/whats-normal-a1c-when-it-misleading, 8 pages Accessed Jan. 28, 2024 (Year: 2017).*

Ball, John R., Bryan T. Miller, and Erin P. Balogh, eds. "Improving diagnosis in health care." (2015), chapter 2. (Year: 2015).*

Benjamini, Y. et al. "Summarizing and correcting the GC content bias in high-throughput sequencing." Nucleic acids research 40.10 (2012): e72-e72.

Broughton, J. P., et al. "CRISPR-Cas12-based detection of SARS-CoV-2." Nature biotechnology 38.7 (2020): 870-874.

Cameron, D.L. et al. (2019). Comprehensive evaluation and characterisation of short read general-purpose structural variant calling software. Nature communications, 10(1), 1-11.

Flicek, P. et al. "Sense from sequence reads: methods for alignment and assembly." Nature methods 6.11 (2009): S6-S12.

Garrison, E. et al. Vcflib: A C++ library for parsing and manipulating VCF files, GitHub https://github.com/ekg/vcflib (2012). Version accessed on Jul. 10, 2017 at https://web.archive.org/web/20170710082528/https://github.com/vcflib/vcflib.

Hatem et al., 2013, "Benchmarking short sequence mapping tools," BMC Bioinformatics 14: p. 184.

Huang, X. et al. "A time-efficient, linear-space local similarity algorithm." Advances in Applied Mathematics 12.3 (1991): 337-357.

Jiang, H., et al. "Skewer: a fast and accurate adapter trimmer for next-generation sequencing paired-end reads." BMC Bioinformatics 15 (2014): 182.

Kalendar et al., 2009 Genes, Genomes, and Genomics, 3 (Special Issue 1), pp. 1-14.

Li, H. et al. 2010, "A survey of sequence alignment algorithms for next-generation sequencing," Brief Bioinformatics 11, pp. 473-483.

Ma B. et al. "PatternHunter: faster and more sensitive homology search." Bioinformatics 18.3 (2002): 440-445.

(Continued)

*Primary Examiner* — Karlheinz R. Skowronek
*Assistant Examiner* — Nidhi Dharithreesan
(74) *Attorney, Agent, or Firm* — MORGAN, LEWIS & BOCKIUS LLP

(57) ABSTRACT

A system and method, the method comprising receiving a laboratory diagnostic testing result associated with a specimen of a subject, the steps of receiving a clinomic profile of the subject, identifying a cohort of similar subjects based at least in part on the clinomic profile of the subject, providing the diagnostic testing results, clinomic profile, and the cohort of similar subjects to a smart output module to generate a personalized, precision medicine based laboratory diagnostic testing result as a smart output and displaying the smart output to a user.

82 Claims, 10 Drawing Sheets

(56) References Cited

OTHER PUBLICATIONS

Roche. Cobas Liat Influenza A/B & RSV Assay. Version accessed online on Sep. 26, 2020 at https://web.archive.org/web/20200926000246/https://diagnostics.roche.com/us/en/products/params/cobas-influenza-a-b-and-rsvassay.html.

Sails, A. D., et al. "Comparison of the Luminex NxTAG respiratory pathogen panel and a multiplex in-house real-time PCR panel for the detection of respiratory viruses in symptomatic patients." Journal of medical microbiology 66.9 (2017): 1291-1296.

Schwartz et al. "Detection and removal of biases in the analysis of next-generation sequencing reads." PloS one 6.1 (2011): e16685.

Selvin et al, Elevated A1C in Adults Without a History of Diabetes in the U.S. Diabetes Care. May 2009; 32(5): 828-833.

Smith, T. F., et al. (1981). Identification of common molecular subsequences. Journal of molecular biology, 147(1), 195-197.

Tang, Y.-W. et al. "Clinical evaluation of the Luminex NxTAG respiratory pathogen panel." Journal of Clinical Microbiology 54.7 (2016): 1912-1914.

Thermofisher. Real-Time PCR Solution for Respiratory Tract Microbiota Detection. Version accessed Oct. 21, 2020 at https://web.archive.org/web/20201021225204/www.thermofisher.com/us/en/home/clinical/clinical-genomics/pathogen-detection-solutions/real-time-pcr-respiratory-tract-microbiota-detection.html.

Wesselschmidt, R. L. et al. "The Stem Cell Laboratory: Design, Equipment, and Oversight." Methods in molecular biology 767 (2011): 3.

World Health Organization. World Health Organization Model List of Essential in Vitro Diagnostics (1st ed. 2018) at https://www.who.int/medical_devices/diagnostics/WHO_EDL_2018.pdf.

U.S. Appl. No. 62/978,067 "Systems and Methods for Detecting Viral DNA from Sequencing," filed Feb. 18, 2020.

* cited by examiner

600

700

ARTIFICIAL INTELLIGENCE ASSISTED PRECISION MEDICINE ENHANCEMENTS TO STANDARDIZED LABORATORY DIAGNOSTIC TESTING

CROSS-REFERENCE TO RELATED APPLICATIONS

This application claims the benefit of priority to U.S. provisional application No. 62/924,515, filed Oct. 22, 2019.

STATEMENT REGARDING FEDERALLY SPONSORED RESEARCH OR DEVELOPMENT

Not applicable.

BACKGROUND OF THE DISCLOSURE

The present disclosure relates to personalizing diagnostic testing results to each and every subject and, more particularly, to systems and methods that comprise a plurality of models to predict, quantify, and correct biases in diagnostic testing results unique to the subject.

Diagnostic laboratory tests generally use fixed reference values to give doctors and other health care providers information about whether a subject has a particular condition or disease. They render a result that is often static, at a point in time, and often not connected to any other data set as a matter of practice. Physicians often order tests in order to determine if a particular result has been achieved. For example, if a physician wants to know if a subject has high cholesterol, they may order a test to determine the values of LDL and HDL in the subject's blood. If they want to want to know if a particular sample of tissue is cancerous, they may order a biopsy and have the pathology slides stained and reviewed to determine if a massive is malignant or benign. The results of such testing is static: they exist in a point in time and they reference a particular value, finding, or result. They are often not connected to phenotypic or therapeutic data relevant to the subject for whom the test was ordered. They are rarely, if ever, connected to molecular data or other morphologic data sets. And they are not enriched by other orthogonal data through the use of machine learning and artificial intelligence. The vast majority of clinical tests are, for lack of a better word, unaware.

For instance, the American Diabetes Association describes the A1C test as a test that measures a subject's average blood sugar for the past 2 to 3 months. Specifically, the A1C test returns a raw test result that is a percentage of the amount of hemoglobin with attached glucose. Diabetes is diagnosed at an A1C of greater than or equal to 6.5%; prediabetes is diagnosed at an A1C of between 5.7% to 6.4%. Normal is diagnosed as an A1C of less than 5.7%.

However, the reference values for A1C and many other lab tests do not adequately identify whether a subject is at risk of developing diabetes or another disease in the future, if the test result is a normal result. For example, an A1C result of 5.6% indicates a diagnosis of no diabetes but, standing alone, provides the ordering doctor with no information about whether the subject is likely to develop diabetes in the future. Similarly, some subjects may have an A1C that is higher than 6.5% but not be diabetic. One study suggested that elevated A1C levels are common in the general population of nondiabetic adults. Selvin et al, *Elevated A1C in Adults Without a History of Diabetes in the U.S. Diabetes Care.* 2009 May; 32(5): 828-833.

There is a need for systems and methods that make use of a personalized medicine approach to analyze the results of laboratory, imaging, and other testing in medicine that make use of fixed reference values. In particular, there is a need for systems and methods for applying methods and systems employing health information data sets, machine learning, and artificial intelligence principles improving an individual's raw test results through the use of that individual's personalized health information—spanning phenotypic, morphologic, and molecular insights.

SUMMARY OF THE DISCLOSURE

In some aspects, the systems and methods may interpret a raw test result in light of an individualized clinomic profile. A "clinomic profile" is a set of information about a subject's medical history and circumstances. A clinomic profile, for instance, may include information from the subject's medical history, genomic profile, metabolomic profile, imaging results, results of other molecular testing (transcriptomic, proteomic, epigenetic, etc.), nutrition history, social and housing history, and family medical history, subject reports and outcomes, among other information. Clinomic profiles may include fields which affect the outcome of testing results, including: the subject's sex, age, race, medical history, general health, diet, and medications. Clinomic profiles may also include metadata about the particular testing or other health care that a subject has received, such as, in the case of laboratory testing, the laboratory's attention to detail in following preparatory instructions for specific testing, variations in laboratory techniques, and variation factors from one laboratory to another.

The raw test result may be a result from a medical test. Exemplary medical tests include, but are not limited to, tests to diagnose or predict the risk of a disease or other health condition, such as cancer, cardiovascular disease, diabetes and other endocrine diseases, skin disease, immune-mediated diseases, stroke, respiratory disease, cirrhosis, high blood pressure, osteoporosis, mental illness, developmental disorders, digestive diseases, viruses, bacterial infections, fungus infections, or urinary and reproductive system infections.

Exemplary medical tests include, but are not limited to, a blood test, a biopsy test, an electrocardiogram endoscopy, a pap test, a computed tomography, a bone marrow examination, a molecular test, a pulmonary function test, a physical examination, a lipid biopsy, a cardiac stress test, an esophageal motility test, a throat culture, an imaging scan or test, and so on.

Specific examples of laboratory tests include, but are not limited to, an A1C test, a complete blood count, a prothrombin time, a basic molecular or metabolic panel, a comprehensive molecular or metabolic panel, a lipid panel, a liver panel, a thyroid stimulating hormone test, a hemoglobin A1C, a urinalysis, a culture, etc. Specific examples of laboratory tests include those listed in the World Health Organization Model List of Essential in Vitro Diagnostics (1$^{st}$ ed. 2018), which list thereof is incorporated by reference.

Specific examples of laboratory tests also include laboratory tests that may be specific to a disease state. For instance, in the field of cancer, laboratory tests include comprehensive genomic profiling, hotspot panels, IHC stains, analyte analysis and algorithmic analysis thereof, etc.

In some examples, the method may include subjecting a subject to a medical test; receiving the raw result of the medical test; associating the raw result of the medical test to a clinomic profile of the subject; comparing the associated data with a data set of health information; adjusting the raw result of the medical test based on the comparison of associated data with a data set of health information; and returning the adjusted raw result of the medical test to the subject's physician.

The "data set of health information" may take various forms and include various types of data. In one example, the data set of health information may be a data set of the health information of other subjects. That health information, for instance, may be "associated data". For each subject in the data set, "associated data" means the subject's raw results of a medical test combined with at least a portion of the clinomic profile of the subject.

In another example, the data set of health information may be a data set of heuristics relating to health information. For example, where the method includes subjecting a subject to an A1C test, and the clinomic profile may include the subject's race, gender, age, and genomic profiling of the G6PD gene, the heuristics may provide for increasing the raw result of the A1C test by 0.81% when the subject is an African-American male adult with a G6PD variant.

In another example, the test result may be compared against one or more sets of data reflective of health information of the subject, individuals medically similar to the subject, other individuals, or other data sets. For example, comparison information may include other phenotypic characteristics of that subject (other diseases they have, prior conditions, etc.) that might alter the result of the test performed. Comparison information may include molecular data for that subject (i.e. genomic profiling done in the past), used to create a new cohort in combination with the test result and the molecular insight to contextualize the result in a manner that is specific for the subject. Comparison information may include morphologic data collected for the subject (such as pathology slides, radiology scans, etc.) that might alter how test results should be interpreted. Comparison information may include information of other subjects, like the subject who was tested, that have had similar results for whom outcome and response data has been collected in order to provide insights into which therapies or trials might be best for the subject, or how likely the disease is to occur, progress, etc.

As an example, the test result may be compared against one or more sets of data reflective of the subject's history of similar test results. The comparison may be performed, for instance, to develop a pattern unique to that subject. Test results may be processed by identifying personalized subject "diagnostic result" thresholds or scaling coefficients for each subject that compensates for the subject's deviation from normal expected results due to a characteristic unique to that subject. In one example, characteristics unique to the subject may be derived from referencing the subject's history of test results to develop a pattern unique to that subject. These test results may be of the same tests taken repeatedly over a period of time or may be results from similar tests. Similar tests may include tests which are similarly affected by underlying conditions, such as a series of unrelated blood tests, each returning elevated readings, which may represent a pattern unique to the subject. For example, if a subject becomes ill, their blood tests may begin rendering different results than expected. In another example, unique characteristics may be based upon a subject's phenotype, including diseases they currently or previously contracted, prior conditions, family medical history, or so on that might alter the result of the test performed. In another example, unique characteristics may be derived from molecular data associated with a subject, such as genomic profiling. The prior molecular data may be referenced to create a cohort of subjects who have similar molecular characteristics to the subject. Analytics may be performed on the cohort of subjects' history of medical results to generate predictions and expectations of the test results that the subject may experience as well as normalization factors that may be applied to the subject's results as a personalized subject diagnostic results threshold to utilize a combination of the test result and the molecular insights that contextualize the lab results in a manner that is personalized for the subject. In another example, unique characteristics may be derived from morphologic data collected associated with a subject such as pathology slides, radiology scans, other imaging results, and so on that suggest the subject's test results should be interpreted according to a personalized scale based on the subject diagnostic results threshold rather than established normal levels. Each of these unique characteristics may be taken into account alone or in combination to determine the best personalized diagnostic result thresholds or adjustment coefficients.

In some examples, a system is provided for storing and analyzing health information to provide a more accurate result to a physician based on the subject's health information, including a first data repository for storing a subject's clinomic profile, a second data repository for storing a raw test result of the subject, a third data repository for storing associated data, in the form of raw test results and clinomic data, for each of a plurality of prior subjects, a plurality of result adjustment engines, one for each test, a user interface for inputting a raw test result to the raw adjustment engine, a display interface for viewing the output of the result adjustment engine, each result adjustment engine may analyze a raw test result for a particular test in light of a data set of health information, such as a plurality of clinomic data/raw test results or heuristics. In some examples the result adjustment engine is a machine learning engine trained on a plurality of clinomic data/raw test results or heuristics.

In some examples, the system may return a risk adjustment analysis specific to the raw test result and the clinomic profile of the subject. The systems and methods described here may be further used to identify a treatment or other therapy for the subject based on the output of the result adjustment engine. In some examples, the system will be longitudinal, meaning that it receives multiple raw lab results and a subject's updated clinomic profile over a period of time. As the system receives a second, third, fourth, etc. lab result (such as a second, third, fourth, etc. A1C result), the system can analyze changes to the raw lab results over time in coordination with changes in the subject's clinomic profile over time. In this way, the effects of the subject's therapy regime may be examined to see if it is improving the subject's health, making the subject's health worse, or not having a measurable effect on the subject's health. In some examples, the results returned back to the physician identify the factors associated with the output of the result adjustment engine.

In each case, static tests that are not "aware" of who the subject truly is, but are simply aware of the singular result that is the foundation of the test that was ordered, are enhanced and made "smarter" by virtue of connecting a singular, static result that is often agnostic as to the subject at hand, with other data sets that allow a physician to contextualize the result in a manner that is personal to the subject, and rely on that more personalized and contextualized result to more precisely choose the optimal therapeutic path.

The disclosure additionally relates to a connected platform and corresponding software and algorithmic product set that allows a "dumb" test to become "smart."

Diagnostic testing in the laboratory, imaging center, and other testing facilities have conformed to the most generalizable procedures available. While conformity is practical for the purposes of standardizing testing results across facilities, the current practice is imperfect. Labs across the country follow internal procedures which are unique to the lab and these deviations are affecting testing results. Even further, the generalized procedures that are being followed for each diagnostic test are not optimized to the subject themselves. Every subject has a unique genome, family history, medical history, diet, and daily routine which affects their testing results and interpretations. Under generalized procedures and standardized result interpretations, none of these subject specific considerations or laboratory variations are factored into interpreting the diagnostic testing results. This lack of awareness from generalized result interpretation frequently leaves physicians and subjects with uncertainty as to the diagnosis and treatment for a subject. With the rise of precision medicine, diagnostic testing is in need of personalization that allows a precision medicine approach to be realized for subject aware diagnostic testing. Enhancing diagnostic testing to advance to smart, subject aware diagnostics by connecting the singular, static result that is often agnostic as to the subject at hand, with other data sets to allow a physician to contextualize the result in a manner that is personalized to the subject. The physician and by extension, the subject, may rely on that more personalized and contextualized result to more precisely choose the optimal therapeutic path.

In an exemplary system, unique characteristics may be compiled for all subjects so that when a subject receives any testing, a cohort of similar subjects may be identified based upon the unique characteristics of the current subject. The identified cohort may then be processed to identify results which may be expected for the subject, outcomes for therapies which may be suggested to the subject, and a personalized subject diagnostic results threshold may be generated. The cohort of subjects may include subjects that have had similar results for whom outcome and response data has been collected in order to provide insights into which therapies or trials might be best for the subject, or how likely the disease is to occur, progress, etc. In addition to the personalized results, analytics associated with the cohort of similar subjects may be provided for the subject informing the subject's physician of therapy insights which may not have otherwise been apparent.

BRIEF DESCRIPTION OF THE SEVERAL
VIEWS OF THE DRAWINGS

The figures described below depict various aspects of the system and methods disclosed herein. It should be understood that each figure depicts an example of aspects of the present system and methods.

Figure 9:
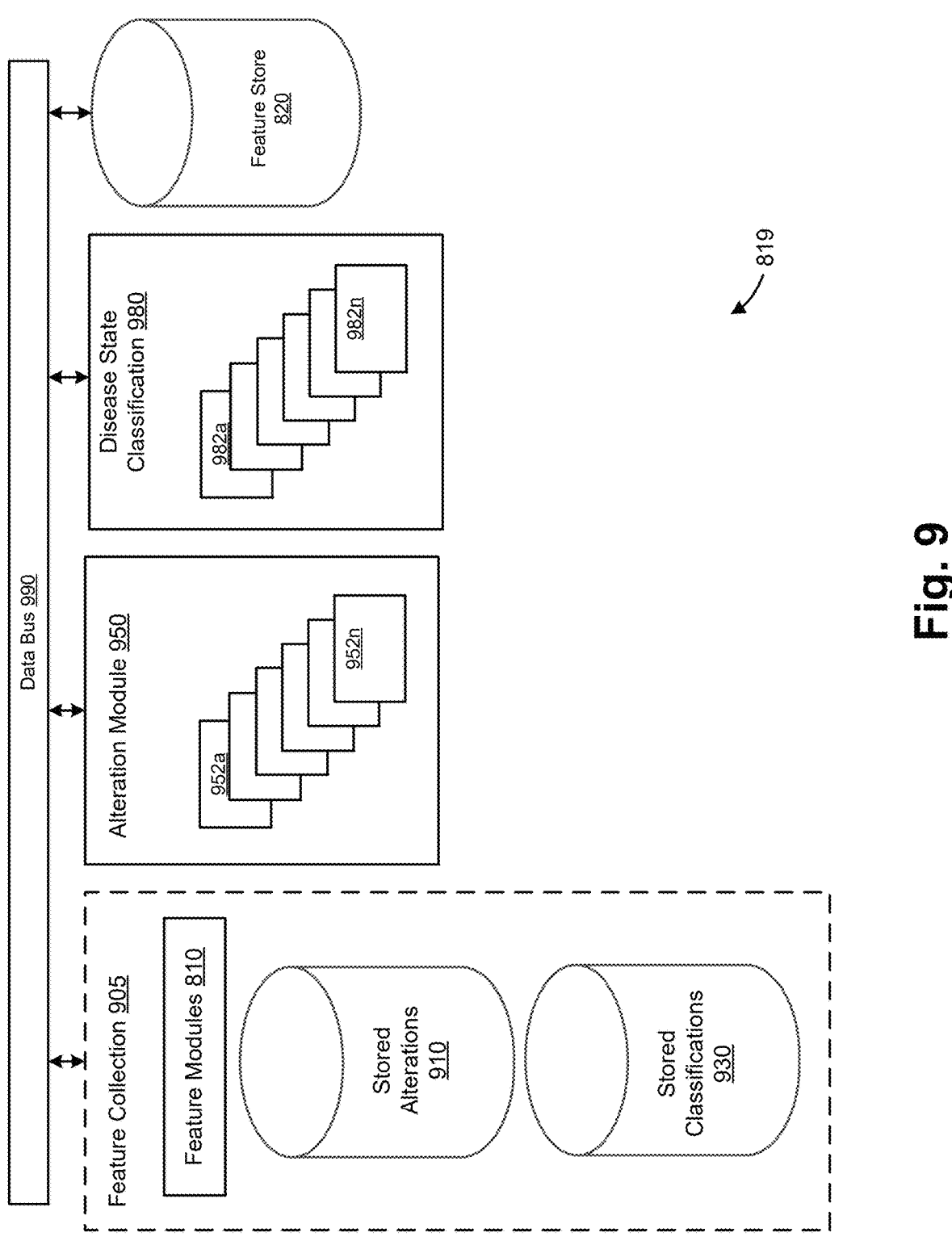
Figure 10:
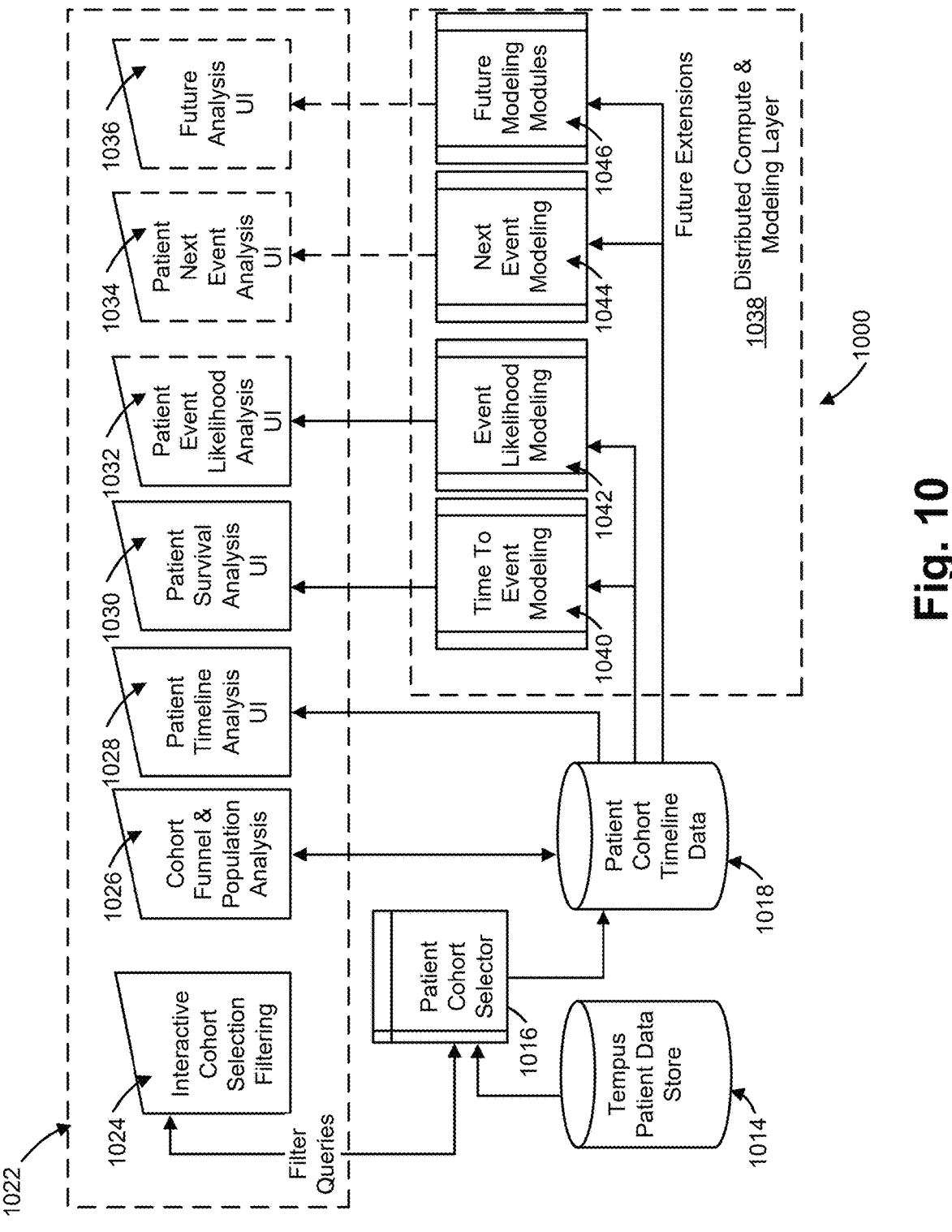

FIG. 9 is an illustration of a block diagram illustrating a system for performing selection, alteration, and calculation of additional features from the patient features, in accordance with some embodiments of the present disclosure; and FIG. 10 is an illustration of an exemplary system diagram of back end and front end components for predicting and analyzing patient cohort response, progression, and survival, that is consistent with at least some aspects of the present disclosure.

DETAILED DESCRIPTION OF THE
DISCLOSURE

The various aspects of the subject disclosure are now described with reference to the drawings, wherein like reference numerals correspond to similar elements throughout the several views. It should be understood, however, that the drawings and detailed description hereafter relating thereto are not intended to limit the claimed subject matter to the particular form disclosed. Rather, the intention is to cover all modifications, equivalents, and alternatives falling within the spirit and scope of the claimed subject matter.

In the following detailed description, reference is made to the accompanying drawings which form a part hereof, and in which is shown by way of illustration, specific embodiments in which the disclosure may be practiced. These embodiments are described in sufficient detail to enable those of ordinary skill in the art to practice the disclosure. It should be understood, however, that the detailed description and the specific examples, while indicating examples of embodiments of the disclosure, are given by way of illustration only and not by way of limitation. From this disclosure, various substitutions, modifications, additions rearrangements, or combinations thereof within the scope of the disclosure may be made and will become apparent to those of ordinary skill in the art.

In accordance with common practice, the various features illustrated in the drawings may not be drawn to scale. The illustrations presented herein are not meant to be actual views of any particular method, device, or system, but are merely idealized representations that are employed to describe various embodiments of the disclosure. Accordingly, the dimensions of the various features may be arbitrarily expanded or reduced for clarity. In addition, some of the drawings may be simplified for clarity. Thus, the drawings may not depict all of the components of a given apparatus (e.g., device) or method. In addition, like reference numerals may be used to denote like features throughout the specification and figures.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof. Some drawings may illustrate signals as a single signal for clarity of presentation and description. It will be understood by a person of ordinary skill in the art that the signal may represent a bus of signals, wherein the bus may have a variety of bit widths and the disclosure may be implemented on any number of data signals including a single data signal.

The various illustrative logical blocks, modules, circuits, and algorithm acts described in connection with embodiments disclosed herein may be implemented as electronic hardware, computer software, or combinations of both. To clearly illustrate this interchangeability of hardware and software, various illustrative components, blocks, modules, circuits, and acts are described generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the embodiments of the disclosure described herein.

In addition, it is noted that the embodiments may be described in terms of a process that is depicted as a flowchart, a flow diagram, a structure diagram, or a block diagram. Although a flowchart may describe operational acts as a sequential process, many of these acts can be performed in another sequence, in parallel, or substantially concurrently. In addition, the order of the acts may be re-arranged. A process may correspond to a method, a function, a procedure, a subroutine, a subprogram, etc. Furthermore, the methods disclosed herein may be implemented in hardware, software, or both. If implemented in software, the functions may be stored or transmitted as one or more instructions or code on a computer-readable medium. Computer-readable media includes both computer storage media and communication media including any medium that facilitates transfer of a computer program from one place to another.

It should be understood that any reference to an element herein using a designation such as "first," "second," and so forth does not limit the quantity or order of those elements, unless such limitation is explicitly stated. Rather, these designations may be used herein as a convenient method of distinguishing between two or more elements or instances of an element. Thus, a reference to first and second elements does not mean that only two elements may be employed there or that the first element must precede the second element in some manner. Also, unless stated otherwise a set of elements may comprise one or more elements.

As used herein, the terms "component," "system" and the like are intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a computer and the computer can be a component. One or more components may reside within a process and/or thread of execution and a component may be localized on one computer and/or distributed between two or more computers or processors.

The word "exemplary" is used herein to mean serving as an example, instance, or illustration. Any aspect or design described herein as "exemplary" is not necessarily to be construed as preferred or advantageous over other aspects or designs.

Furthermore, the disclosed subject matter may be implemented as a system, method, apparatus, or article of manufacture using standard programming and/or engineering techniques to produce software, firmware, hardware, or any combination thereof to control a computer or processor based device to implement aspects detailed herein. The term "article of manufacture" (or alternatively, "computer program product") as used herein is intended to encompass a computer program accessible from any computer-readable device, carrier, or media. For example, computer readable media can include but are not limited to magnetic storage devices (e.g., hard disk, floppy disk, magnetic strips . . . ), optical disks (e.g., compact disk (CD), digital versatile disk (DVD) . . . ), smart cards, and flash memory devices (e.g., card, stick). Additionally it should be appreciated that a carrier wave can be employed to carry computer-readable electronic data such as those used in transmitting and receiving electronic mail or in accessing a network such as the Internet or a local area network (LAN). Of course, those skilled in the art will recognize many modifications may be made to this configuration without departing from the scope or spirit of the claimed subject matter.

Definitions

"Disease state" means a state of disease, such as cancer, cardiology, depression, mental health, diabetes, infectious disease, epilepsy, dermatology, autoimmune diseases, or other diseases. A disease state may reflect the presence or absence of disease in a subject, and when present may further reflect the severity of the disease.

System Overview

Figure 1:
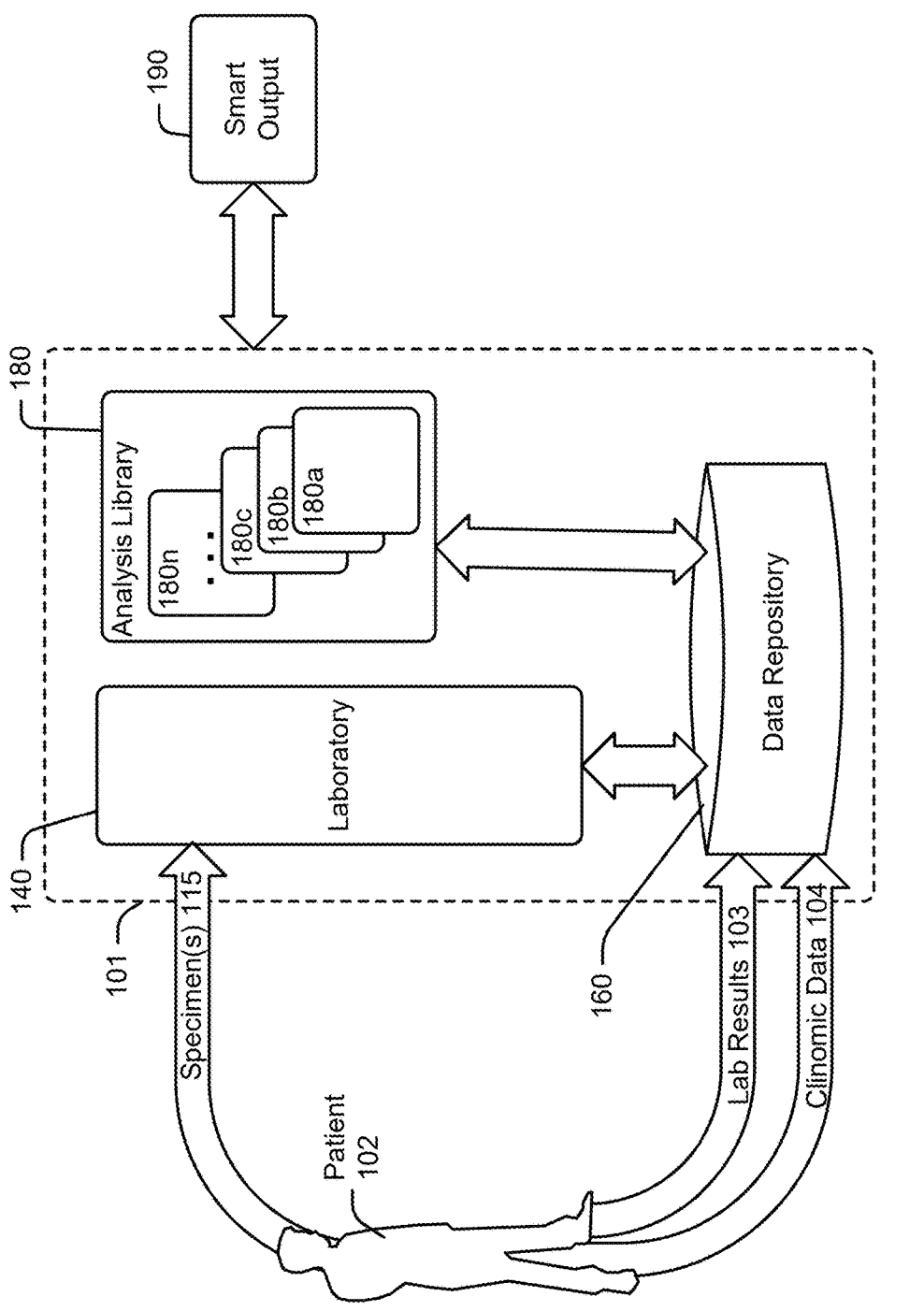
FIG. 1 is an illustration of an exemplary system 101 for use in the analysis of laboratory tests that is consistent with at least some aspects of the present disclosure.

Referring now to the drawings wherein like reference numerals correspond to similar elements throughout the several views and, more specifically, referring to FIG. 1, the present disclosure will be described in the context of an exemplary system. FIG. 1 illustrates an exemplary system 101 for use in the analysis of laboratory tests. The system 101 may comprise a laboratory 140, a data repository 160, and an analysis library 180. The data repository 160 is in operative communication with the laboratory 140 and the analysis library 180, such that the results from the laboratory 140 may be stored in the data repository 160 and the data repository 160 may provide various sets of information to one or more analysis modules 180a-n in the analysis library 180. The laboratory 140 may also be in operative communication with the analysis library 180, such that laboratory test results may be provided to the analysis library 180 upon completion of the laboratory results. Each analysis module 180i may have at least one input to receive the results from the laboratory 140 or other information and at least one output The system 101 may receive a lab result 103 of a subject as well as a clinomic dataset 104 of the subject. Optionally the system 101 may receive one or more specimens 115 of the subject for analysis in the laboratory 140 in addition to lab result 103 and clinomic dataset 104.

Clinomic Profile

A clinomic profile, as used herein, may be generated for each subject from a diverse set of clinical information available within subject health records. Clinical information may be based upon fields which have been entered into an electronic medical record (EMR) or an electronic health record (EHR) by a physician, nurse, or other medical professional.

A clinomic profile may include information about a subject across a variety of disease states. Molecular clinical information may also be part of a subject's clinomic profile. Molecular clinical information may be curated from genetic sequencing results. Sequencing may include next-generation sequencing (NGS) and may be long-read, short-read, or other forms of sequencing a subject's genome. Clinical information may also combine a variety of features together across varying fields of medicine, including: diagnosis, response to treatment regimens, genetic profiles, clinical and phenotypic characteristics, and/or other medical, geographic, demographic, clinical, molecular, or genetic features. For example, clinical information in the area of cancer may include demographics (such as Year of Birth, Gender, Race/Ethnicity, Relevant Comorbidities, Smoking History), diagnosis (Site (Tissue of Origin), Initial Diagnosis Date, Initial Diagnosis, Histology, Histologic Grade, Metastatic Diagnosis, Metastatic Diagnosis Date, Site(s) of Metastasis, Stage (e.g., TNM, ISS, DSS, FAB, RAI, Binet)), assessments, labs & molecular pathology (e.g. Type of Lab (e.g. CBS, CMP, PSA, CEA), Lab Results and Units, Lab Event Date, Performance Status (e.g. ECOG, Karnofsky), Performance Status Score, Performance Status Date, Molecular Pathology Test Event*, Gene/Biomarker/Assay, Gene/Biomarker/Assay Result (e.g. Positive, Negative, Equivocal, Mutated, Wild Type, Molecular Pathology Method (e.g., IHC, FISH, NGS), Molecular Pathology Provider), Treatment (e.g. Drug Name, Drug Start Date, Drug End Date, Dosage and Units, Drug Number of Cycles, Surgical Procedure Type, Surgical Procedure Date, Radiation Site, Radiation Modality Radiation Start Date, Radiation End Date, Radiation Total Dose Delivered, Radiation Total Fractions Delivered), outcomes (e.g. Response to Therapy (e.g. CR, PR, SD, PD), RECIST measurement, Outcome/Observation Date, Progression Date, Recurrence Date, Adverse Event to Therapy, Adverse Event Date of Presentation, Adverse Event Grade. Death Date, Last Follow-up Date, and Disease Status at Last Follow Up). Genetic profiles may be derived from RNA or DNA sequencing. Features derived from DNA and RNA sequencing may include genetic variants which are present in the sequenced specimen.

Further analysis of the genetic variants may include additional steps such as identifying single or multiple nucleotide polymorphisms, identifying whether a variation is an insertion or deletion event, identifying loss or gain of function, identifying fusions, calculating copy number variation, calculating microsatellite instability, or identifying other structural variations within DNA and RNA. Clinical information may include imaging features identified through review of stained H&E or IHC slides, review of x-ray scans, CT scans, or MRI scans. Analysis of slides for H&E staining or IHC staining may reveal features such as tumor infiltration, programmed death-ligand 1 (PD-L1) status, human leukocyte antigen (HLA) status, or other immunology features. Still other clinical information may include features derived from structured, curated, or electronic medical or health records. These derived features including diagnosis, symptoms, therapies, outcomes; subject demographics such as subject name, date of birth, gender, ethnicity, date of death, address, smoking status; diagnosis dates for the present malady, such as cancer, illness, disease, diabetes, depression, Alzheimer's, or other physical or mental maladies; personal medical history, family medical history, clinical history such as date of initial diagnosis, treatments and outcomes, medications prescribed or taken, surgeries, radiotherapy, imaging, adverse effects, associated outcomes, genetic testing and laboratory information such as performance scores, lab tests, prognostic indicators, date of genetic testing, testing provider used, testing method used, such as genetic sequencing method or gene panel, gene results, such as included genes, variants, expression levels/statuses, or corresponding dates to any of the above.

Clinical information may also include features derived from additional medical or research based 'omics including proteome, transcriptome, epigenome, metabolome, microbiome, and other multi-omic fields. Proteome features may comprise features associated with information derived from the proteins produced in the subject. These features may include protein composition, structure, and activity; when and where proteins are expressed; rates of protein production, degradation, and steady-state abundance; how proteins are modified, for example, post-translational modifications such as phosphorylation; the movement of proteins between subcellular compartments; the involvement of proteins in metabolic pathways; how proteins interact with one another; or modifications to the protein after translation from the RNA such as phosphorylation, ubiquitination, methylation, acetylation, glycosylation, oxidation, or nitrosylation.

Other-omic features may be derived from: cognitive genomics, a collection of features relating to the changes in cognitive processes associated with genetic profiles; comparative genomics, a collection of features relating to the relationship of genome structure and function across different biological species or strains; functional genomics, a collection of features relating to gene and protein functions and interactions including transcriptomics; interactomics, a collection of features comprising the study relating to large-scale analyses of gene-gene, protein-protein, or protein-ligand interactions; metagenomics, a collection of features relating to metagenomes such as genetic material recovered directly from environmental samples; neurogenomics, a collection of features relating to genetic influences on the development and function of the nervous system; pangenomics, a collection of features relating to the entire collection of gene families found within a given species; personal genomics, a collection of features relating to genomics concerned with the sequencing and analysis of the genome of an individual such that once the genotypes are known, the individual's genotype can be compared with the published literature to determine likelihood of trait expression and disease risk to enhance personalized medicine suggestions; epigenomics, a collection of features relating to supporting the structure of genome, including protein and RNA binders, alternative DNA structures, and chemical modifications on DNA; nucleomics, a collection of features relating to the complete set of genomic components which form the cell nucleus as a complex, dynamic biological system; lipidomics, a collection of features relating to cellular lipids, including the modifications made to any particular set of lipids produced by a subject; proteomics, a collection of features relating to proteins, including the modifications made to any particular set of proteins produced by a subject; immunoproteomics, a collection of features relating to large sets of proteins involved in the immune response; nutriproteomics, a collection of features relating to identifying molecular targets of nutritive and non-nutritive components of the diet including the use of proteomics mass spectrometry data for protein expression studies; proteogenomics, a collection of features relating to biological research at the intersection of proteomics and genomics including data which identifies gene annotations; structural genomics, a collection of features relating to 3-dimensional structure of every protein encoded by a given genome using a combination of modeling approaches; glycomics, a collection of features relating to sugars and carbohydrates and their effects in the subject; foodomics, a collection of features relating to the intersection between the food and nutrition domains through the application and integration of technologies to improve consumer's well-being, health, and knowledge; transcriptomics, a collection of features relating to RNA molecules, including mRNA, rRNA, tRNA, and other non-coding RNA, produced in cells; metabolomics, a collection of features relating to chemical processes involving metabolites, or unique chemical fingerprints that specific cellular processes leave behind, and their small-molecule metabolite profiles; metabonomics, a collection of features relating to the quantitative measurement of the dynamic multiparametric metabolic response of cells to pathophysiological stimuli or genetic modification; nutrigenetics, a collection of features relating to genetic variations on the interaction between diet and health with implications to susceptible subgroups; cognitive genomics, a collection of features relating to the changes in cognitive processes associated with genetic profiles; pharmacogenomics, a collection of features relating to the effect of the sum of variations within the human genome on drugs; pharmacomicrobiomics, a collection of features relating to the effect of variations within the human microbiome on drugs; toxicogenomics, a collection of features relating to gene and protein activity within particular cell or tissue of an organism in response to toxic substances; mitointeractome, a collection of features relating to the process by which the mitochondria proteins interact; psychogenomics, a collection of features relating to the process of applying the powerful tools of genomics and proteomics to achieve a better understanding of the biological substrates of normal behavior and of diseases of the brain that manifest themselves as behavioral abnormalities, including applying psychogenomics to the study of drug addiction to develop more effective treatments for these disorders as well as objective diagnostic tools, preventive measures, and cures; stem cell genomics, a collection of features relating to stem cell biology to establish stem cells as a model system for understanding human biology and disease states; connectomics, a collection of features relating to the neural connections in the brain; microbiomics, a collection of features relating to the genomes of the communities of microorganisms that live in the digestive tract; cellomics, a collection of features relating to the quantitative cell analysis and study using bioimaging methods and bioinformatics; and tomomics, a collection of features relating to tomography and omics methods to understand tissue or cell biochemistry at high spatial resolution from imaging mass spectrometry data.

Laboratory

The laboratory 140 may include one or more analytical, quality, biosafety, clinical, public health, medical, incubator, production, or research & development capabilities or technologies. The laboratory 140 may conduct analysis in support of one or more disease states. The laboratory 140 may have organ or disease-oriented panels, drug testing, therapeutic drug assays, clinical pathology capabilities, urinalysis, molecular pathology, chemistry, hematology and coagulation, immunology, transfusion medicine capabilities, microbiology, anatomic pathology, cytogenetic capabilities, transcutaneous analysis capabilities, metabolomic capabilities, stool analysis capabilities, and reproductive medicine capabilities. Laboratory 140 may process specimens in support of analysis of a subject's clinomic profile. The laboratory, for example, may support analysis of a subject's condition relating to a disease state. The laboratory 140 may be a laboratory for processing specimens 115, such as saliva, blood, urine, stool, hair, tumor tissue, healthy tissue, or other collections of cells or fluids from a subject 102. A laboratory 140 may include an order reception and subject order creation process to receive a request from a physician to process a specimen 115 for testing, a specimen intake process to receive a specimen 115 and associate the order with the subject 102, a specimen testing process to generate laboratory results of the order for the specimen 115, an order satisfaction process to record the order as completed, and a laboratory reporting process to report out the laboratory results of subject 102. See Appendix A for exemplary tests that the laboratory 140 may perform.

The laboratory 140 may also include systems and methods for several different laboratory equipment and setups as described below.

General Equipment/Setup

The laboratory 140 may include equipment for preparation of subjects, collection of specimens, processing specimens, and storing and/or transporting specimens. General equipment may include slides, microscopes, scales, glassware, plasticware, forceps, scalpels, clot tubes, vacuum tubes, boxes, plastic specimen bags, frozen gel packs, ovens, burners, temperature controlled storage, and similar equipment. General equipment may also include analytical equipment, such as mass spectrometers, chromatographs, titraters, spectrometers, particle size analyzers, rheometers, elemental analyzers, and connected computing devices for performing mathematical analysis.

Next-Generation Sequencing (NGS) Equipment/Setup

The laboratory 140 may include equipment for storing specimens, preparation of specimens for sequencing, isolation, amplification, and sequencing. Equipment may include freezers, slicers, slides, microscopes, slide scanners, staining kits, slide scrapers, centrifuges, vortexes, water baths, rotating mixers, pipettes, PCR equipment, thermal cyclers, PCR reagents and kits, sequencers, automated liquid handlers, sonicators, automation workstations, plate readers, plate imagers, automated isolation and purification systems, nucleic acid quantitators, nucleic acid analyzers, ultrasonicator, hybridization oven, and other nucleic acid sequencing equipment.

Enzyme-Linked ImmunoSorbent Assay (ELISA) Equipment/Setup

The laboratory 140 may include equipment, materials, and supplies for detecting substances that have antigenic properties such as proteins, hormones, bacterial antigens and antibodies. ELISA equipment may include washers, centrifuges, microplate readers, cold storage equipment, pipettes and tips, dispensers, incubator/shakers, and microplates. Equipment may also include photometers, spectrophotometers, microplate readers, microplate washers, reagents, reagent dispensers, data analysis software, spike-ins, washing equipment, and the like. The laboratory may offer ELISA tests as a laboratory developed test or as a test kit.

Cholesterol and Low-Density Lipoproteins (LDL) Equipment/Setup

The laboratory 140 may include equipment, materials, and supplies for conducting blood testing for cholesterol or LDL levels. For instance, the laboratory may include blood cholesterol measuring devices/meters, test strips, sterile swaps, cotton balls, a disposable container, syringes, collection tubes, vials, reagents, deep freezer, boxes, cold freeze bags, or other lab equipment.

Imaging Equipment/Setup

The laboratory 140 may include equipment for the imaging of varying specimens. Imaging may include radiological scanning such as radiography, fluoroscopy, projectional radiograph, magnetic resonance imaging, nuclear medicine, scintigraphy, ultrasound, elastography, tactile imaging, strain imagine, impulse imaging, photoacoustic imaging, tomography, x-ray, computed tomography, single-photon emission computerized tomography (SPECT), positron emission tomography, echocardiography, functional near-infrared spectroscopy, fusion imaging, magnetic particle imaging, pathology and other imaging equipment.

The laboratory 140 may include radiography equipment to perform the above listed imaging scans such as subject gowns, resting beds, radiation protection equipment, lead shields, ultrasonography machines, x-ray generator, array detectors, thin-film transistors, x-ray detector, photographic plates, photographic film, image plates, flat panel detectors, image intensifiers, vacuum tubes, electron lenses, ionization chambers, Geiger counters, dosimeters, x-ray contrast media, contrast agents, Bucky-Potter grid, echocardiography machines, cardiac sonographers, ultrasound transducer, ultrasound probe, computer axial tomography machines, MRI machines, magnets, radio wave generator, cross sectional imaging software, NMR machines, NMR tube, NMR probe, spectrometer, super-conducting magnet, magnetic shielding, magnetic shimming, shim coils, gradient coils, resonant coils, volume coils, betatrons, linear accelerators, vacuum changers, vacuum pumps, cathode, synchrotrons, fMRI machines, positron emission tomography machines, radiotracers, radio detectors, radio scanners, radio-isotope machines, radiation emitters, radionuclides, radioactive detectors, nuclear scintigraphy machines, SPECT machines, planar camera, SPECT camera, dual head cameras, multi-head cameras, CT imaging systems, attenuation correction system, nuclear medicine processing computer, multi-imager formatter, laser printer, dry film, image storage, dose calibrator, ionization chamber, gas ventilation delivery system and trap, ECG monitor, treadmill, intravenous contrast delivery system brachytherapy machines, magnetostrictive transducers, ultrasonic disintegrator, and respective imaging method specific software.

The laboratory may further include pathology equipment for specimen collection, specimen receipt, specimen storage, specimen slide preparation, slide staining, and specimen sequencing. Equipment for pathology may include the equipment above for NGS and may further include flow cytometers, tissue baths, haemocytometer, tubes, stands, embedding molds, paraffin wax, block holder, microtome, needles, syringes, spirometer, monometers, staining rack, staining container, drying rack, slide tray, reagents, reagent reservoirs, staining kits, temperature regulating containers and storage, microscopes, and other pathology equipment.

Infectious Diseases Equipment/Setup

The laboratory 140 may include equipment for conducting infectious disease testing from fluid, tissue, and aerosolized specimens to detect bacteria, viruses, parasites, or other infectious agents. Infectious disease testing may also include serologic diagnosis. Equipment may include sterile specimen containers, saline, specimen freezers, syringes, needles, scalpels, swaps, petri dishes, incubators, refrigerators, culture media, centrifuges, intravascular catheter, continuous monitoring blood culture system, pour plates, agar plates, endoluminal brush, biofilm, microscope, microbiology kits, shunts, drains, gram stains, microscope, molecular diagnosis tests, rapid tests, lateral flow assays, chemistry analyzer, coagulation analyzer, glucose analyzers, urinalysis analyzer, testing strips, PCR machines, thermal cyclers, and PCR analysis software, CRISPR kits, and other infectious disease detection equipment.

The laboratory may include equipment for conducting infectious disease testing, such as the testing described in Broughton et al, CRISPR—Cas12-based detection of SARS-COV-2, Nature Biotechnology (April 2020), the contents of which are incorporated by reference in their entirety.

Organoid Laboratory

The laboratory may include organoid equipment for specimen collection, specimen receipt, specimen storage, cell culturing, cell monitoring, treatment testing, gene therapy, and gene editing as described above for other laboratories, including syringes, needles, scalpels, freezers, incubators, petri dishes, bio-growth media, deep freezers, microscopes, medical treatments and drugs, centrifuges, culture mediums, freezing media, and other equipment.

The laboratory may include equipment for conducting organoid isolation, culturing, and modeling, such as the setup described in Wesselschmidt et al, *The Stem Cell Laboratory: Design, Equipment, and Oversight*, Methods Mol. Biol. (June 2013), the contents of which are incorporated by reference in their entirety.

Analysis Library

The analysis library 180 may comprise analysis modules 180a-n. Each analysis module 180a-n may process a set of data from the data repository 160 in combination with one or more of the subject's lab result 103 and/or a set of data from the subject's clinomic data 104 to generate a smart output 190. Optionally each analysis module 180a-n may process a set of laboratory result data of one or more specimen 115 from the laboratory 140 alone or in addition to one or more of lab result 103 of a subject or clinomic data 104 to generate a smart output 190.

Smart Output

Figure 2:
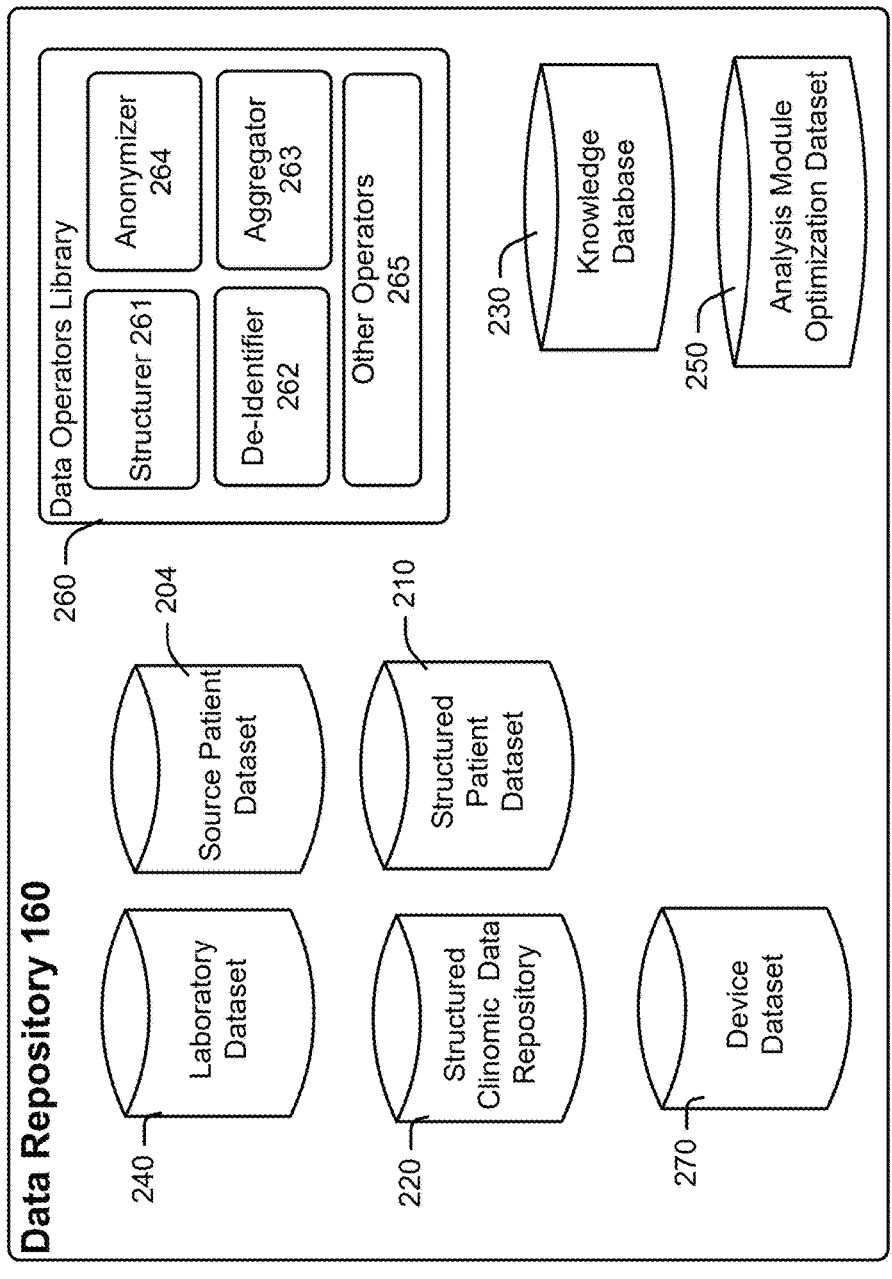
FIG. 2 is an illustration of exemplary datasets which may be stored alongside or within a data repository, that is consistent with at least some aspects of the present disclosure.

Smart output 190 may comprise one or more of a personalized test result specific to the subject 102; a personalized threshold of evaluation specific to the subject 102; a representation of data, such as clinomic profiles, from a cohort of subjects similar to the subject 102, including features or associations/insights within such data cohort; an association of the test result 102 with a knowledge database, such as a database of drug-gene interactions, a database of promising treatments based on scientific evidence, and the like; or an association of a prior test result with testing from the laboratory 140. The smart output 190 may take the form of a diagnosis and/or treatment report, a research use only report, or a presentation for further review by a molecular board. Smart output 190 may further comprise a graphical user interface for viewing any of the representations of personalized or precision medicine based laboratory results, evaluation thresholds, associations, insights, or the like. Test results may include results of biological, microbiological, serological, chemical, immunohematological, radioimmunological, hematological, biophysical, cytological, pathological, toxicological or other examination of materials derived from the human body for the purposes of providing information for the diagnosis, prevention or treatment of any disease or impairment of, or the assessment of, the health of humans including determining drug use by humans Source Subject Dataset FIG. 2 illustrates exemplary datasets which may be stored alongside or within data repository 160. A source subject dataset (sometimes referred to herein as a source patient dataset) 204 may store the lab result 103 and the clinomic data 104 of the subject 102 in source form. Source form, or source format, may include written health record reports, such as progress notes, genomic test reports, other lab reports, medication lists, imaging files, and any other records that are found in a subject's health record. Source form may include an image of a physical written health record report or an image of a copy, such as a scan, email, or fax of the original document. In some instances, a source form may include an electronic record of the source form, such as a document which has been processed via an optical character recognition service, software, or algorithm or an original representation of the subject's electronic health record as created by the subject's medical provider. The records stored in the source subject dataset 204 may come from one or more doctors, medical providers or institutions, or health care systems that have provided care to the subject 102.

Structured Subject Dataset

A structured subject dataset (sometimes referred to herein as a structured patient dataset) may store the health information from a source subject dataset, but in structured form. For instance, the structured subject dataset 210 (sometimes referred to herein as a structured patient dataset) may store the health information such that each data element stored in the dataset is associated with a label or descriptor for that information element. The health information in the structured subject dataset 210 may be stored in the form of tables or a relational dataset as well as in other formats permitting the storage of native medical records, such as image files, variant call files, binary files, and so forth.

For example, structured subject dataset 210 may include therapies information including molecularly-guided neoadjuvant and/or adjuvant therapies, immunotherapies, molecular therapies, CAR-T cell therapy, CRISPR therapies, checkpoint inhibitors, and/or personalized vaccines when a subject 102 is a cancer subject. In another example, source subject dataset 204 may include general subject data such as date of birth, gender, occupation, blood type, Rh, addresses, or telephone numbers; home monitoring data such as blood glucose monitoring, blood pressure monitoring, weight, body mass index, waist circumference, or height; laboratory data such as glycated hemoglobin, total cholesterol, triglyceride, high-density lipoprotein, low-density lipoprotein, thyroid stimulator hormone, microalbuminuria, urine glucose, proteinuria, or creatinine blood test results; examination data such as foot examination, eye examination, dental examination, pulse, or sensation test results; vaccination data such as influenza vaccination, pneumococcal vaccination, or hepatitis B vaccination statuses; subject education data such as smoking cessation, self-care, or lifestyle pamphlets; and drug data such as drug names, medication prescription notes, dosage, times taking medication, prescription date, date of stopping, reasons for stopping, duration of taking, and other instructions provided to the subject associated with the medication when a subject 102 is a diabetes subject. A structured subject dataset may store data using valuesets such as SNOMED, where numerical identifiers are used to reflect specific health information of the subject.

Structured Clinomic Data Repository

A structured clinomic data repository 220 may store the health information from a plurality of subjects whose health information has been ingested into the system 101. The structured clinomic data repository may take the same or a similar form to the structured subject dataset 210. The number of subjects whose health information are stored in the structured clinomic data repository 220 may be in the thousands, tens of thousands, hundreds of thousands, millions, tens of millions, hundreds of millions, or beyond. In one example, the structured clinomic data repository 220 may be arranged to permit the identification of each data element stored in the dataset with the person with whom the data element relates. In another example, the structured clinomic data repository 220 may be de-identified, so that it does not reasonably permit the identification of each data element with the person to whom the data element relates. A structured clinomic data repository may store data using valuesets such as SNOMED, where numerical identifiers are used to reflect specific health information of the subject.

The table below reflects a simplified representation of a data dictionary in a structured clinomic data repository focused in oncology.

TABLE 1

| Data Field Type | Structured Data Fields |
| --- | --- |
| Demographics | Age/DOB |
| | Gender |
| | Race/Ethnicity |
| | Smoking History |
| Diagnosis | Site |
| | Date of Diagnosis |
| | Date of Metastatic Diagnosis |
| | Metastatic Site |
| | Stage |
| | Stage - Tumor |
| | Stage - Node |
| | Stage - Metastasis |
| | Grade |
| | Histology |
| Assessments & Labs | Performance Status (ECOG or Karnofsky) |
| | Date of Performance Status |
| Molecular Pathology | Type of Genetic Test |
| | Date of Genetic Test |
| | Genetic Test Result |
| | Genetic Testing Provider |
| | Molecular Variant |
| Treatments | Surgical Procedure |
| | Date of Surgical Procedure |
| | Cancer Medication |
| | Cancer Medication Start Date |
| | Cancer Medication End Date |
| | Cancer Medication Dosage |
| | Radiation Site |
| | Radiation Start Date |
| | Radiation End Date |
| Outcomes | Tumor Response (PD, SD, PR, CR) |
| | Date of Tumor Response |
| | Adverse Events |
| | Date of Adverse Event Presentation |
| | Date of Death |

The table below reflects a simplified representation of a data dictionary in a structured clinomic data repository focused in mental health conditions.

TABLE 2

| Data Field Type | Structured Data Fields |
| --- | --- |
| Demographics | Age/DOB |
| | Sex |
| | Gender |

TABLE 2-continued

| Data Field Type | Structured Data Fields |
| --- | --- |
| | Race/Ethnicity |
| | Employment Status |
| | Smoking History |
| | Substance Abuse History |
| | Family History of Mental Illness |
| | Comorbidities |
| Diagnosis | Date of Diagnosis |
| | Date of Relapses/Recurrences/Remissions |
| | Diagnostic Method(s) |
| | Clinical Evaluations & Results |
| | Symptoms |
| | Symptom Severity |
| Assessments & Labs | CBC, CRP, Cytokine Panels, etc. (all blood testing) |
| | Urinalysis |
| | Clinician Interview/Questionnaire Dates |
| | Observations & Results from Clinician Interviews/ Questionnaires |
| | Psychotherapy/CBT Session Dates |
| | Observations & Results from Psychotherapy/ CBT Session Dates |
| | Non-subject & Non-physician progress reports (i.e. family member report of progress) |
| | Date of Physician Appointments |
| | Reason for Missed Appointment |
| Pharmacogenetic Testing | Date of Genetic Test |
| | Genotype Test Results |
| | Metabolic Phenotype Test Results |
| | Genetic Testing Provider |
| | Medication Classifications Reported |
| Treatments | Medication |
| | Medication Start Date |
| | Medication End Date |
| | Medication Dosage |
| | Non-medication Intervention (i.e. lifestyle changes) |
| | Non-medication Intervention Start Date |
| | Non-medication Intervention End Date |
| Outcomes | Disease Response |
| | Date of Disease Response |
| | Symptom Response |
| | Date of Symptom Response |
| | Adverse Events |
| | Date of Adverse Event |
| | Suicide Ideation Report Type |
| | Date of Suicide Ideation Report |
| | Suicide Attempt |
| | Date of Suicide Attempt |
| | Date of Death |
| | Cause of Death |

A knowledge database 230 may store information from various fields of learning relating to laboratory testing and a human medical condition. For example, the knowledge database 230 may store information from learned journals that associate a first set of factors with a second set of factors. The knowledge database 230 may store information that represents facts about the world and an inference engine that can reason about those facts and use rules and other forms of logic to preserve published findings, deduce new facts, or highlight inconsistencies. For example, the knowledge database 230 may store facts about the interaction between laboratory test results and the human medical condition based on clinomic analysis.

Laboratory Dataset

A laboratory dataset 240 may store information generated from operations in the laboratory 140. For example, the dataset 240 may store information generated from operations on organoids, animals, cell lines, blood, tissue, saliva, stool, similar human solid, fluid, or cellular specimens, or other specimens. The dataset 240 may store information generated from procedures such as genomic profiling, such as through the use of next-generation sequencing, as well as information generated from other laboratory procedures such as those listed in the List of Essential In Vitro Diagnostics (EDL) in the World Health Organization Model List of Essential in Vitro Diagnostics (1st ed. 2018), such list incorporated herein by reference for all purposes (the "IVD List"). As another example, when the subject 102 is a cancer subject, the laboratory dataset 240 may store information generated from operations in the laboratory 140 that include comprehensive genomic profiling, IHC staining, cell-free DNA Analysis, liquid biopsy, circulating tumor cell testing, integrated recurrence confirmation, organoid testing, and/or pathway analysis. The laboratory 140 may, in some examples, include a bioinformatics pipeline for processing raw sequencing information and a variant pipeline for calling and characterizing variants from the processed sequencing information. In other examples, the laboratory may include lab screening such as cholesterol, blood glucose, complete blood count, prothrombin time, basic or comprehensive metabolic panel, lipid panel, or liver panel testing. Further testing may include laboratory tests from the IVD List and those disclosed below from the listing of types of laboratory tests.

Analysis Module Optimization Dataset

An analysis module optimization dataset 250 may store data elements used to optimize one or more analysis modules 180*a-n*. The data elements in the dataset 250 may be used to optimize the operation of the analysis modules 180*a-n* in various use cases. Optimizations may include hypertuning parameters or other inputs associated with the AI, machine learning models, or neural networks which improve the performance of the respective module for the subject results being processed at the time of operation. The "AI" component of each analysis module 180*a-n* may be gradient boosting models, random forest models, neural networks (NN), regression models, Naive Bayes models, or machine learning algorithms (MLA). A MLA or a NN may be trained from a training data set. In an exemplary analysis module, a training data set may include imaging, pathology, clinical, and/or molecular reports and details of a subject, such as those curated from an EHR or genetic sequencing reports. The training data may be based upon features of the subject from the subject's clinomic profile. MLAs include supervised algorithms (such as algorithms where the features/classifications in the data set are annotated) using linear regression, logistic regression, decision trees, classification and regression trees, Naïve Bayes, nearest neighbor clustering; unsupervised algorithms (such as algorithms where no features/classification in the data set are annotated) using Apriori, means clustering, principal component analysis, random forest, adaptive boosting; and semi-supervised algorithms (such as algorithms where an incomplete number of features/classifications in the data set are annotated) using generative approach (such as a mixture of Gaussian distributions, mixture of multinomial distributions, hidden Markov models), low density separation, graph-based approaches (such as mincut, harmonic function, manifold regularization), heuristic approaches, or support vector machines. NNs include conditional random fields, convolutional neural networks, attention based neural networks, deep learning, long short term memory networks, or other neural models where the training data set includes subject clinomic profile features, a plurality of laboratory diagnostic test results, a plurality of specimen samples, DNA and/or RNA expression data for each specimen, and/or pathology reports covering imaging data for each specimen. While MLA and neural networks identify distinct approaches to machine learning, the terms may be used interchangeably herein. Thus, a mention of MLA may include a corresponding NN or a mention of NN may include a corresponding MLA unless explicitly stated otherwise. Training may include providing optimized datasets, labeling these traits as they occur in subject records, and training the MLA to predict smart outputs. Artificial NNs are efficient computing models which have shown their strengths in solving hard problems in artificial intelligence. They have also been shown to be universal approximators (can represent a wide variety of functions when given appropriate parameters). Some MLA may identify features of importance and identify a coefficient, or weight, to them. The coefficient may be multiplied with the occurrence frequency of the feature to generate a score, and once the scores of one or more features exceed a threshold, certain classifications may be predicted by the MLA. A coefficient schema may be combined with a rule based schema to generate more complicated predictions, such as predictions based upon multiple features. For example, ten key features may be identified across different classifications. A list of coefficients may exist for the key features, and a rule set may exist for the classification. A rule set may be based upon the number of occurrences of the feature, the scaled weights of the features, or other qualitative and quantitative assessments of features encoded in logic known to those of ordinary skill in the art. In other MLA, features may be organized in a binary tree structure. For example, key features which distinguish between the most classifications may exist as the root of the binary tree and each subsequent branch in the tree until a classification may be awarded based upon reaching a terminal node of the tree. For example, a binary tree may have a root node which tests for a first feature. The occurrence or non-occurrence of this feature must exist (the binary decision), and the logic may traverse the branch which is true for the item being classified. Additional rules may be based upon thresholds, ranges, or other qualitative and quantitative tests. While supervised methods are useful when the training dataset has many known values or annotations, the nature of EMR/EHR documents is that there may not be many annotations provided. When exploring large amounts of unlabeled data, unsupervised methods are useful for binning/bucketing instances in the data set. A single instance of the above models, or two or more such instances in combination, may constitute a model for the purposes of models within analysis module 180*a-n*.

Device Dataset

A device dataset 270 may store data elements generated from one or more devices utilized by or otherwise associated with the subject. For example, a diabetes subject may utilize various insulin delivery methods such as digital syringes, digital pens, digital insulin pumps, blood glucose meters, continuous glucose monitors, automated insulin delivery devices such as the artificial pancreas, and so forth. A subject with a cardiovascular condition may utilize a digital blood pressure machine, a heart monitor, and so forth. A subject with a stroke condition, for example, may utilize an orthotic, prosthetic, or other assistive device with digital monitoring features enabled. A subject who requires obesity care may enter information through a smartphone app, for instance, in order to track food and water intake, exercise, and weight-loss medication administration. Each device may be in operative communication with one or more aspects of the system 101 in order to transmit information from the device into the system for processing and storage into the device dataset 270. Device dataset 270 may further include communication processes, application interfaces, and/or conversion parameters for receipt of the subject information from the devices included within the dataset autonomously. Such communication processes may include communication over the World Wide Web, Wi-Fi, Bluetooth, internet of things, or other communication mediums. Application interfaces may include the APIs and libraries needed to access the communication processes. Conversion parameters may include data formats of which the devices provide subject information and processes for converting the device subject information to the structured format of structured databases 210 and 220.

Data Operators Library

The data operators library 260 may include one or more instances of operators that may be used to perform operations on the data, whether or not stored in the data repository 160. Exemplary operators may include a structurer 261, a de-identifier 262, an aggregator 263, an anonymizer 264, and other operators 265. Instances of operators may include one or more operators 261-265 alone or in combination for conversion of a first one or more data types or a second one or more data types. For example, a structurer 261 may ingest source subject data from the dataset 204 and produce structured subject data for storage in the dataset 210. As another example, a de-identifier 262 may de-identify health information stored in the data repository 160 so that the resulting health information is in a form that is considered de-identified in accordance with laws, industry guidelines, and/or market norms. As another example, an aggregator 263 may aggregate a first set of data with a second set of data, either from within or outside of the data repository 160. As another example, an anonymizer 264 may anonymize a first set of data from the data repository 160 so that the resulting health information is in a form that is considered anonymized in accordance with laws, industry guidelines, and/or market norms. Other exemplary operators may include operators for extracting and cleansing health information. Other exemplary operators may include operators for image analysis, such as artificial-intelligence image analysis, to extract features of interest from one or more medical images. Each instance of operators may contain a plurality of operations 261-265 that may differ depending on the data ingested by the data operator. For example, a structurer 261 may have a first set of structuring operations to structure genomic profile data, a second set of structuring operations to structure medical records such as progress notes or medication lists, a third set of structuring operations to structure native images, a fourth set of structuring operations to structure metabolomic information, and so forth. Each operator may be automated, may rely on a combination of automation and human interaction, or may rely on human interaction. An operator that relies on human interaction may utilize a user interface through a display screen to permit human interaction. For example, the structurer 261 may include a software platform that permits human users to review source medical records of the subject 102 and extract structured data from those source medical records for inclusion into the structured subject dataset 210. As a very simple illustrative example, a source record that reads "Patient was administered 85 mg of docetaxel on Jun. 3, 2010" may be structured as follows: "action"="administration"; "therapy"="docetaxel"; "dosage"=85; "dosage_units"="mg"; action_date: "Jun. 3, 2010". In another example, an instance of operators 260*i* may include a structurer 261, aggregator 262, and de-identifier 263 together in instance 260. Structurer 261 may receive unstructured subject information from laboratory result 103, source subject data 204, and clinomic data 104. Structurer 261 may convert the format of each unstructured subject information to a structured format of the system 101, such as the structure format associated with databases 210 or 220.

Once structured, the structured data may be passed to aggregator 262 to combine the data from multiple sources into a single dataset. A final processing may occur at de-identifier 263 to remove PHI from the de-identified and structured data. In this and similar manners, instances of operators may process data between each of the input lab results 103, clinomic data 104, results from laboratory 140, and any data sources 204, 210, 220, 230, 240, 250, 260, 270 for further storage or processing at analysis library 180.

Orchestration Module

Figure 4:
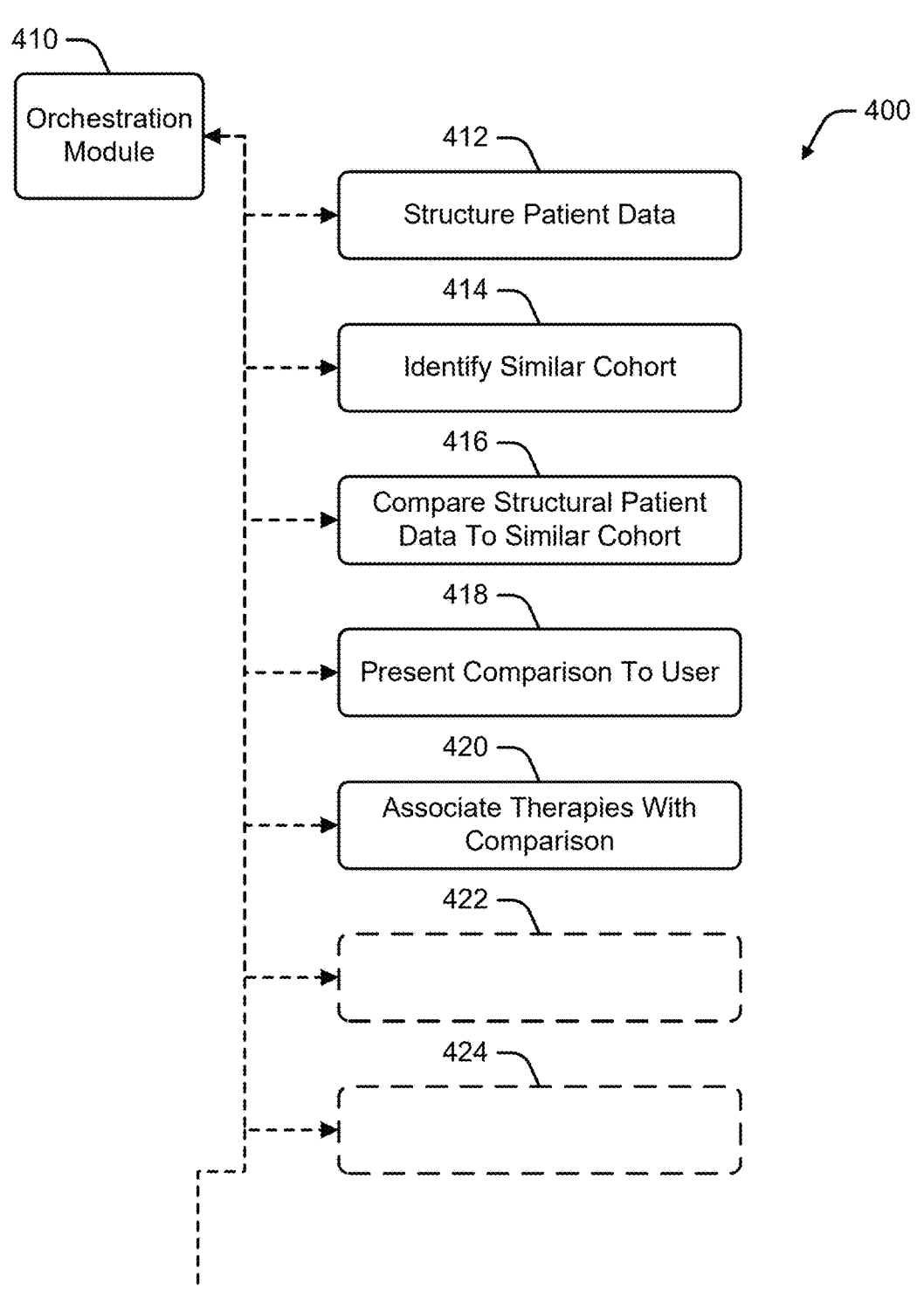
FIG. 4 is a flow chart that shows an exemplary method that is consistent with at least some aspects of the present disclosure.

FIG. 4 includes a flow chart illustrating an exemplary method 400 that may be performed by the FIG. 1 system, 101 that is consistent with at least some aspects of the present disclosure. In FIG. 4, method 400 is orchestrated by an orchestration module 410 and begins with a process 412 for structuring received subject data for a specific subject, such as subject data received at data repository 160, including lab result 103 and clinomic data 104. Next, the method includes a process 414 to examine the structured subject data and identify features from which to build a cohort of similar subjects based upon data associated with other subjects who have features in common with a specific subject for which a test has been performed. Then, the method includes a process 416 to compare structured subject data to the cohort such that a personalized smart output is derived for the specific subject. The method includes a process 418 to present the smart output (e.g., results of the comparison) to a user (e.g., a physician) in the form of a report or an interactive software interface. Finally, the method includes process 420 for associating therapies with results of the comparison at 418. In this way, any therapies which may improve or hinder the prognosis of the subject are visible to the treating physician and may be considered in generating a treatment plan for the subject. Blocks 422 and 424 represent other processes that may, for example, be added to the end of the method shown in FIG. 4.

Sequencing from a laboratory may take many forms. A specific panel of genes may be targeted through a combination of probes which selectively target informative genes for each disease state or a whole genome sequencing may be performed from which specific genes may be referenced for each test the laboratory offers as part of its sequencing portfolio. In one example, plurality of panels may exist, a panel for informative genes targeting oncological diseases, a panel for mental health diseases, one panel for diabetic diseases, a panel for blood tests, a panel for cardiological diseases, a panel for infectious diseases, a panel for epileptic diseases, a panel for dermatological diseases, a panel for autoimmune diseases, or one or more panels for other diseases. In another example, a whole genome panel may exist and one or more tests may be performed from the whole genome sequencing results. In yet another example, a plurality of targeted panels may exist in conjunction with the whole genome sequencing panel. Aspects of panel selection and probe design are discussed in more detail with respect to the methods set forth in FastPCR Software for PCR Primer and Probe Design and Repeat Search (Kalendar et al., 2009 Genes, Genomes, and Genomics, 3 (Special Issue 1), pp. 1-14) which is incorporated by reference herein.

Wet Lab Process

The laboratory 140 may prepare slides from a specimen using slide preparation techniques such as freezing the specimen and slicing layers, embedding the specimen in paraffin wax and slicing layers, smearing the specimen on a slide, or other slide preparation methods. For purposes of the following disclosure, a slide and a slice may be used interchangeably. A slide stores a slice of tissue from the specimen and receives a label identifying the specimen from which the slice was extracted and the sequence number of the slice from the specimen. In some embodiments, two or more samples, slices, and/or slides are obtained from a specimen—for example, two or more tissue slices can be taken that are adjacent or substantially adjacent to each other. In some cases, the tissue slices are obtained such that some of the pathology slides prepared from the respective slices are stained (for example, histopathology slides, hematoxylin and eosin stained slides, immunohistochemistry stained slides, etc.), whereas some of the pathology slides are used for obtaining sequencing information. Staining the specimen may reveal cellular characteristics such as cell nuclei, lymphocytes, stroma, epithelium, biological markers, immunological characteristics, or other cellular characteristics.

A stained slide may be reviewed by a pathologist for identification of a diagnosis and any cellular features, such as a diagnosis of cancer or other disease state and the quantity of cells and their differences from the normal cells of that or similar type. In some embodiments, the review may be performed by an artificial intelligence engine. Aspects of diagnosis classification are discussed in more detail with respect to U.S. patent application Ser. No. 15/930,234, filed May 12, 2020, titled "Systems And Methods For Multi-Label Cancer Classification," incorporated by reference herein in its entirety. Aspects of cellular characteristic classification are discussed in more detail with respect to U.S. patent application Ser. No. 16/830,186, filed Mar. 25, 2020, titled "Determining Biomarkers From Histopathology Slide Images," incorporated by reference herein in its entirety.

Unstained slides may be scrapped to remove the sliced specimen. When the specimen includes a slice of paraffin embedded specimen, the paraffin may first be removed with a xylene wash. Then, RNA or DNA may be isolated from the specimen using one or more reagents such as proteinase K to generate a liquid solution of DNA or guanidinium thiocyanate-phenol-chloroform extraction to generate a liquid solution of RNA. Each solution of isolated molecules may be subjected to a quality control protocol to determine the concentration and/or quantity of the molecules in the solution, which may include the use of a fluorescent dye and a fluorescence microplate reader, standard spectrofluorometer, or filter fluorometer. Then the isolated molecules may be mechanically sheared to an average length using an ultrasonicator and analyzed to determine their fragment size via gel electrophoresis techniques.

RNA or DNA from the isolated molecules may be amplified and purified using reagents and/or polymerase chain reaction (PCR) techniques, which are distinct from quantitative or reverse transcription quantitative PCR (qPCR or RT-qPCR). Then the concentration and/or quantity of the amplified molecules may be quantified using a fluorescent dye and a fluorescence microplate reader, standard spectrofluorometer, or filter fluorometer. The molecule amplification may be performed on a device, for example, an Illumina C-Bot2, and the resulting flow cell containing amplified target-captured DNA or RNA libraries may be sequenced on a next generation sequencer, for example, an Illumina HiSeq 4000 or an Illumina NovaSeq 6000 to a unique on-target depth selected by the user, for example, 300×, 400×, 500×, 10,000×, etc. Samples may be further assessed for uniformity with each sample required to have 95% of all targeted bp sequenced to a minimum depth selected by the user, for example, 300×. The next generation sequencer may generate a FASTQ, BCL, or other file for each flow cell or each subject sample.

A BCL file may include raw image data of one or more subject specimens which are sequenced. BCL image data is an image of the flow cell across each cycle during sequencing. A cycle may be implemented by illuminating a subject specimen with a specific wavelength of electromagnetic radiation, generating a plurality of images which may be processed into base calls via BCL to FASTQ processing algorithms which identify which base pairs are present at each cycle. The resulting FASTQ may then comprise the entirety of reads for each subject specimen paired with a quality metric in a range from 0 to 64 where a 64 is the best quality and a 0 is the worst quality. In an oncological disease state, a tumor specimen and a normal specimen from the same subject may be matched after sequencing such that a tumor-normal analysis may be performed. Each FASTQ file contains reads that may be paired-end or single reads, and may be short-reads or long-reads, where each read represents one detected sequence of nucleotides in a molecule that was isolated from the specimen.

The resulting FASTQ file may then be provided for additional processing including variant calling and bioinformatics analysis.

Variant Calling

The FASTQ file compiles all of the sequencing reads, the sequences of nucleic acids detected during sequencing of the specimen, without knowledge of the location from the genome where each corresponding sequencing read lines up, or aligns, to identify the genome of the specimen. An alignment process may be performed which aligns each sequencing read with the genome of the specimen, including genomes of humans, animals, bacteria, virus, or other entities.

In some embodiments, preprocessing steps may be performed, e.g., filtering sequence reads based on a desired quality, e.g., size and/or quality of the base calling. In some embodiments, quality control checks are performed to ensure the data is sufficient for variant calling. For instance, entire reads, individual nucleotides, or multiple nucleotides that are likely to have errors may be discarded based on the quality rating associated with the read in the FASTQ file, the known error rate of the sequencer, and/or a comparison between each nucleotide in the read and one or more nucleotides in other reads that has been aligned to the same location in the reference genome. Filtering may be done in part or in its entirety by various software tools, for example, a software tool such as Skewer. See, Jiang, H. et al., BMC Bioinformatics 15(182): 1-12 (2014). FASTQ files may be analyzed for rapid assessment of quality control and reads, for example, by a sequencing data QC software such as AfterQC, Kraken, RNA-SeQC, FastQC, or another similar software program. For paired-end reads, reads may be merged.

In some embodiments, when a subject with cancer is sequenced having both a germline specimen and a normal tissue specimen, two FASTQ output files are generated, one for the germline specimen and one for the somatic specimen. A 'matched' (e.g., panel-specific) workflow is run to jointly analyze the matched FASTQ files. When a matched germline sample is not available from the subject, FASTQ files from the somatic specimen are analyzed in the 'tumor-only' mode.

In various embodiments, FASTQ data from each isolate may be filtered. Such filtering may include correcting or masking sequencer errors and removing (trimming) low quality sequences or bases, adapter sequences, contaminations, chimeric reads, overrepresented sequences, biases caused by library preparation, amplification, or capture, and other errors.

Similarly, in some embodiments, sequencing may be performed on a pool of nucleic acid sequencing libraries prepared from different biological samples, e.g., from the same or different subjects. Accordingly, in some embodiments, the system demultiplexes the data (e.g., using a demultiplexing algorithm) to separate sequence reads into separate files for each sequencing library included in the sequencing pool, e.g., based on UMI or subject identifier sequences added to the nucleic acid fragments during sequencing library preparation, as described above. In some embodiments, the demultiplexing algorithm is part of the same software package as one or more pre-processing algorithms. For instance, the bcl2fastq or bcl2fastq2 conversion software (Illumina®) include instructions for both converting the native file format output from the sequencer and demultiplexing sequence reads output from the reaction.

The sequence reads are then aligned, e.g., using an alignment algorithm, to a reference sequence construct, e.g., a reference genome, reference exome, or other reference construct prepared for a particular targeted-panel sequencing reaction. For example, in some embodiments, individual sequence reads, in electronic form (e.g., in FASTQ files), are aligned against a reference sequence construct for the species of the subject (e.g., a reference human genome) by identifying a sequence in a region of the reference sequence construct that best matches the sequence of nucleotides in the sequence read. In some embodiments, individualized sequencing reads are aligned against a plurality of reference sequence constructs including a reference human genome, a reference microbiology genome, a reference virology genome, and other reference genomes. In some embodiments, the sequence reads are aligned to a reference exome or reference genome using known methods in the art to determine alignment position information. The alignment position information may indicate a beginning position and an end position of a region in the reference genome that corresponds to a beginning nucleotide base and end nucleotide base of a given sequence read. Alignment position information may also include sequence read length, which can be determined from the beginning position and end position. A region in the reference genome may be associated with a gene or a segment of a gene. Any of a variety of alignment tools can be used for this task.

For instance, local sequence alignment algorithms compare subsequences of different lengths in the query sequence (e.g., sequence read) to subsequences in the subject sequence (e.g., reference construct) to create the best alignment for each portion of the query sequence. In contrast, global sequence alignment algorithms align the entirety of the sequences, e.g., end to end. Examples of local sequence alignment algorithms include the Smith-Waterman algorithm (see, for example, Smith and Waterman, J Mol. Biol., 147(1):195-97 (1981), which is incorporated herein by reference), Lalign (see, for example, Huang and Miller, Adv. Appl. Math, 12:337-57 (1991), which is incorporated by reference herein), and PatternHunter (see, for example, Ma B. et al., Bioinformatics, 18(3):440-45 (2002), which is incorporated by reference herein).

In some embodiments, the read mapping process starts by building an index of either the reference genome or the reads, which is then used to retrieve the set of positions in the reference sequence where the reads are more likely to align. Once this subset of possible mapping locations has been identified, alignment is performed in these candidate regions with slower and more sensitive algorithms. See, for example, Hatem et al., 2013, "Benchmarking short sequence mapping tools," BMC Bioinformatics 14: p. 184; and Flicek and Birney, 2009, "Sense from sequence reads: methods for alignment and assembly," Nat Methods 6(Suppl. 11), S6-S12, each of which is hereby incorporated by reference. In some embodiments, the mapping tools methodology makes use of a hash table or a Burrows-Wheeler transform (BWT). See, for example, Li and Homer, 2010, "A survey of sequence alignment algorithms for next-generation sequencing," Brief Bioinformatics 11, pp. 473-483, which is hereby incorporated by reference.

Other software programs designed to align reads include, for example, Novoalign (Novocraft, Inc.), Bowtie, Burrows Wheeler Aligner (BWA), and/or programs that use a Smith-Waterman algorithm. Candidate reference genomes include, for example, hg19, GRCh38, hg38, GRCh37, and/or other reference genomes developed by the Genome Reference Consortium. In some embodiments, the alignment generates a SAM file, which stores the locations of the start and end of each read according to coordinates in the reference genome and the coverage (number of reads) for each nucleotide in the reference sequencing.

For example, in some embodiments, each read of a FASTQ file is aligned to a location in the human genome having a sequence that best matches the sequence of nucleotides in the read. There are many software programs designed to align reads, for example, Novoalign (Novocraft, Inc.), Bowtie, Burrows Wheeler Aligner (BWA), programs that use a Smith-Waterman algorithm, etc. Alignment may be directed using a reference genome (for example, hg19, GRCh38, hg38, GRCh37, other reference genomes developed by the Genome Reference Consortium, etc.) by comparing the nucleotide sequences in each read with portions of the nucleotide sequence in the reference genome to determine the portion of the reference genome sequence that is most likely to correspond to the sequence in the read. In some embodiments, one or more SAM files are generated for the alignment, which store the locations of the start and end of each read according to coordinates in the reference genome and the coverage (number of reads) for each nucleotide in the reference genome. The SAM files may be converted to BAM files. In some embodiments, the BAM files are sorted and duplicate reads are marked for deletion, resulting in de-duplicated BAM files.

In some embodiments, the sequencing data is normalized, e.g., to account for pull-down, amplification, and/or sequencing bias (e.g., mappability, GC bias etc.). See, for example, Schwartz et al., PLOS ONE 6(1):e16685 (2011) and Benjamini and Speed, Nucleic Acids Research 40(10): e72 (2012), the contents of which are hereby incorporated by reference, in their entireties, for all purposes.

In some embodiments, SAM files generated after alignment are converted to BAM files. Thus, after preprocessing sequencing data generated for a pooled sequencing reaction, BAM files are generated for each of the sequencing libraries present in the master sequencing pools. In some embodiments, BAM files are sorted, and duplicate reads are marked for deletion, resulting in de-duplicated BAM files. For example, tools like SamBAMBA mark and filter duplicate alignments in the sorted BAM files.

In some embodiments algorithms may be applied to identify variants unique to the disease state informed genome and variants existing in the subject may be identified. In one example, oncology informed variants are identified and classified as either germline or somatic, e.g., based on sequencing data, population data, or a combination thereof. In another example, variants are classified as germline variants, and/or non-actionable variants, when they are represented in the population above a threshold level, e.g., as determined using a population database such as ExAC or gnomAD. For instance, in some embodiments, variants that are represented in at least 1% of the alleles in a population are annotated as germline and/or non-actionable. In other embodiments, variants that are represented in at least 2%, at least 3%, at least 4%, at least 5%, at least 7.5%, at least 10%, or more of the alleles in a population are annotated as germline and/or non-actionable. In some embodiments, sequencing data from a matched sample from the subject, e.g., a normal tissue sample, is used to annotate variants identified in a cancerous sample from the subject. That is, variants that are present in both the cancerous sample and the normal sample represent those variants that were in the germline prior to the subject developing cancer, and can be annotated as germline variants.

In various aspects, the detected genetic variants and genetic features are analyzed as a form of quality control. For example, a pattern of detected genetic variants or features may indicate an issue related to the sample, sequencing procedure, and/or bioinformatics pipeline (e.g., example, contamination of the sample, mislabeling of the sample, a change in reagents, a change in the sequencing procedure and/or bioinformatics pipeline, etc.).

In some embodiments, variant analysis of aligned sequence reads, e.g., in SAM or BAM format, includes identification of single nucleotide variants (SNVs), multiple nucleotide variants (MNVs), indels (e.g., nucleotide additions and deletions), and/or genomic rearrangements (e.g., inversions, translocations, and gene fusions). Essentially, identification first identifies a difference between the sequence of an aligned sequence read and the reference sequence to which the sequence read is aligned and makes a record of the variant, e.g., in a variant call format (VCF) file. For instance, software packages such as freebayes and pindel are used to call variants using sorted BAM files and reference BED files as the input. For a review of variant calling packages see, for example, Cameron, D. L. et al., Nat. Commun., 10(3240):1-11 (2019). A raw VCF file is output, showing the locations where the nucleotide base in the sample is not the same as the nucleotide base in that position in the reference sequence construct.

In some embodiments, raw VCF data is then normalized, e.g., by parsimony and left alignment. For example, software packages such as vcfbreakmulti and vt are used to normalize multi-nucleotide polymorphic variants in the raw VCF file and a variant normalized VCF file is output. See, for example, E. Garrison, "Vcflib: A C++ library for parsing and manipulating VCF files, GitHub github.com/ekg/vcflib (2012), the content of which is hereby incorporated by reference, in its entirety, for all purposes. In some embodiments, a normalization algorithm is included within the architecture of a broader variant identification software package.

An algorithm is then used to annotate the variants in the (e.g., normalized) VCF file, e.g., determines the source of the variation, e.g., in oncology, whether the variant is from the germline of the subject (e.g., a germline variant), a cancerous tissue (e.g., a somatic variant), a sequencing error, or of an indeterminable source. In some embodiments, an annotation algorithm is included within the architecture of a broader variant identification software package. However, in some embodiments, an external annotation algorithm is applied to (e.g., normalized) VCF data obtained from a conventional variant identification software package. The choice to use a particular annotation algorithm is well within the purview of the skilled artisan, and in some embodiments is based upon the data being annotated.

For example, in some embodiments, where both a somatic sample and a normal tissue sample of the subject are analyzed, variants identified in the normal tissue sample inform annotation of the variants in the somatic sample. In some embodiments, where a particular variant is identified in the normal tissue sample, that variant is annotated as a germline variant in the somatic sample. Similarly, in some embodiments, where a particular variant identified in the somatic sample is not identified in the normal tissue sample, the variant is annotated as a somatic variant when the variant otherwise satisfies any additional criteria placed on somatic variant calling, e.g., a threshold variant allele frequency (VAF) in the sample.

By contrast, in some embodiments, where only a somatic sample is being analyzed, the annotation algorithm relies on other characteristics of the variant in order to annotate the origin of the variant. For instance, in some embodiments, the annotation algorithm evaluates the VAF of the variant in the sample, e.g., alone or in combination with additional characteristics of the sample, e.g., tumor fraction. Accordingly, in some embodiments, where the VAF is within a first range encompassing a value that corresponds to a 1:1 distribution of variant and reference alleles in the sample, the algorithm annotates the variant as a germline variant, because it is presumably represented in cfDNA originating from both normal and cancer tissues. Similarly, in some embodiments, where the VAF is below a baseline variant threshold, the algorithm annotates the variant as undeterminable, because there is not sufficient evidence to distinguish between the possibility that the variant arose as a result of an amplification or sequencing error and the possibility that the variant originated from a cancerous tissue. Similarly, in some embodiments, where the VAF falls between the first range and the baseline variant threshold, the algorithm annotates the variant as a somatic variant.

In some embodiments, the baseline variant threshold is a value from 0.01% VAF to 0.5% VAF. In some embodiments, the baseline variant threshold is a value from 0.05% VAF to 0.35% VAF. In some embodiments, the baseline variant threshold is a value from 0.1% VAF to 0.25% VAF. In some embodiments, the baseline variant threshold is about 0.01% VAF, 0.015% VAF, 0.02% VAF, 0.025% VAF, 0.03% VAF, 0.035% VAF, 0.04% VAF, 0.045% VAF, 0.05% VAF, 0.06% VAF, 0.07% VAF, 0.075% VAF, 0.08% VAF, 0.09% VAF, 0.1% VAF, 0.15% VAF, 0.2% VAF, 0.25% VAF, 0.3% VAF, 0.35% VAF, 0.4% VAF, 0.45% VAF, 0.5% VAF, or greater. In some embodiments, the baseline variant threshold is different for variants located in a first region, e.g., a region identified as a mutational hotspot and/or having high genomic complexity, than for variants located in a second region, e.g., a region that is not identified as a mutational hotspot and/or having average genomic complexity. For example, in some embodiments, the baseline variant threshold is a value from 0.01% to 0.25% for variants located in the first region and is a value from 0.1% to 0.5% for variants located in the second region. In some embodiments, a baseline variant threshold is influenced by the sequencing depth of the reaction, e.g., a locus-specific sequencing depth and/or an average sequencing depth (e.g., across a targeted panel and/or complete reference sequence construct). In some embodiments, the baseline variant threshold is dependent upon the type of variant being detected. For example, in some embodiments, different baseline variant thresholds are set for SNPs/MNVs than for indels and/or genomic rearrangements. For instance, while an apparent SNP may be introduced by amplification and/or sequencing errors, it is much less likely that a genomic rearrangement is introduced this way and, thus, a lower baseline variant threshold may be appropriate for genomic rearrangements than for SNPs/MNVs.

In some embodiments, one or more additional criteria are required to be satisfied before a variant can be annotated as a somatic variant. For instance, in some embodiments, a threshold number of unique sequence reads encompassing the variant must be present to annotate the variant as somatic. In some embodiments, the threshold number of unique sequence reads is only applied when certain conditions are met, e.g., when the variant allele is located in a region of average genomic complexity. In some embodiments, a threshold sequencing coverage, e.g., a locus-specific and/or an average sequencing depth (e.g., across a targeted panel and/or complete reference sequence construct) must be satisfied to annotate the variant as somatic. In some embodiments, bases contributing to the variant must satisfy a threshold mapping quality to annotate the variant as somatic. In some embodiments, alignments contributing to the variant must satisfy a threshold alignment quality to annotate the variant as somatic. In some embodiments, one or more genomic regions is blacklisted, preventing somatic variant annotation for variants falling within the region. In various embodiments, any combination of the additional criteria, as well as additional criteria not listed above, may be applied to the variant calling process. Again, in some embodiments, different criteria are applied to the annotation of different types of variants.

In some embodiments, genomic rearrangements (e.g., inversions, translocations, and gene fusions) are detected following de-multiplexing by aligning tumor FASTQ files against a human reference genome using a local alignment algorithm, such as BWA. In some embodiments, DNA reads are sorted and duplicates may be marked with a software, for example, SAMBlaster. Discordant and split reads may be further identified and separated. These data may be read into a software, for example, LUMPY, for structural variant detection. In some embodiments, structural alterations are grouped by type, recurrence, and presence and stored within a database and displayed through a fusion viewer software tool. The fusion viewer software tool may reference a database, for example, Ensembl, to determine the gene and proximal exons surrounding the breakpoint for any possible transcript generated across the breakpoint. The fusion viewer tool may then place the breakpoint 5' or 3' to the subsequent exon in the direction of transcription. For inversions, this orientation may be reversed for the inverted gene. After positioning of the breakpoint, the translated amino acid sequences may be generated for both genes in the chimeric protein, and a plot may be generated containing the remaining functional domains for each protein, as returned from a database, for example, Uniprot.

Once variants have been identified, characterization and subsequent testing and/or analysis of the variants may be performed via a bioinformatics pipeline to identify the meaningfulness of each variant which has been called.

Although the above description of variant calling focuses on variant calling in the context of a cancer test, it should be understood that additional and alternate techniques for variant calling in cancer as well as other disease states are known in the art.

Bioinformatics Pipeline

Alignment files prepared as described above may then be passed to a bioinformatics pipeline, where the sequences are analyzed to identify genomic alterations (e.g., SNVs/MNVs, indels, genomic rearrangements, fusions, copy number variations, etc.) and/or determine various characteristics of the subject's cancer (e.g., MSI status, TMB, tumor ploidy, HRD status, tumor fraction, tumor purity, methylation patterns, etc.). Many software packages for identifying genomic alterations are known in the art, for example, freebayes, PolyBayse, samtools, GATK, pindel, SAMtools, Breakdancer, Cortex, Crest, Delly, Gridss, Hydra, Lumpy, Manta, and Socrates. For a review of many of these variant calling packages see, for example, Cameron, D. L. et al., Nat. Commun., 10(3240):1-11 (2019), the content of which is hereby incorporated by reference, in its entirety, for all purposes. Generally, these software packages identify variants in sorted SAM or BAM files, relative to one or more reference sequence constructs 158. The software packages then output a file e.g., a raw VCF (variant call format), listing the variants (e.g., genomic features) called and identifying their location relevant to the reference sequence construct (e.g., where the sequence of the sample nucleic acids differ from the corresponding sequence in the reference construct). In some embodiments, system digests the contents of the native output file to populate feature data in test subject data store. In other embodiments, the native output file serves as the record of these genomic features in test subject data store.

Generally, the systems described herein can employ any combination of available variant calling software packages and internally developed variant identification algorithm. In some embodiments, the output of a particular algorithm of a variant calling software is further evaluated, e.g., to improve variant identification. Accordingly, in some embodiments, system employs an available variant calling software package to perform some of all of the functionality of one or more of the algorithms shown in feature extraction module.

Variant Characterization

A bioinformatics pipeline may implement variant characterization via processes including a variant characterization DNA process and a variant characterization RNA process. Exemplary characterization subprocesses of the DNA process and RNA process includes S/M (NP) processes to identify single and multiple nucleotide polymorphisms (e.g., variations), an InDels process to detect insertions in and deletions from the genome, a CNV process to detect copy number variations, a fusions process to detect gene fusions, a TMB process to calculate tumor mutational burden, an MSI process to calculate microsatellite instability, and an IHC process. Once variants are characterized, each variant is then classified by the characterization item as benign, likely benign, pathogenic, likely pathogenic or VUS (e.g., variant of unknown significance) and then stored as characterized variants along with the classifications at which point the variant classification process is complete.

A structural variant characterization, such as insertion/deletion (InDel), single nucleotide variant/polymorphism (SNV), or multiple nucleotide variant/polymorphism (MNP) process may include receiving the plurality of variants from the VCF data, analyzing each variant with characterization information, weighting the evidence generated from the analysis, and assigning a characterization to each variant.

Analysis with characterization information may be performed automatically. In some examples, an analysis engine may crawl the world wide web and publication portals for articles, clinical trials, publications, and other available resources to digest and collate information regarding the pathogenicity of variants based on their occurrence in the general population, occurrence in a disease state positive population, in-silico predictors, laboratory reviews, protein effects, genetic effects, functional studies or assays, and a myriad of other criteria selected based on the evidence pertinent to the field of the disease state being informed by the sequencing. Other criteria may include internally curated evidence or indicia of pathogenicity based on subjects with the identified variant and their survival and/or responses to treatments of the disease state.

A copy number variant (CNV) characterization process may include receiving the plurality of variants from the VCF data, analyzing each variant against a threshold, and identifying any copy number gains or copy number losses from the comparison.

A gene rearrangement characterization process may include receiving the VCF data, referencing a database, determining the gene and proximal exons surrounding the breakpoint for any possible transcript generated across the breakpoint, identifying a breakpoint 5' or 3' to the subsequent exon in the direction of transcription. Orientation may be reversed for an inverted gene. After positioning of the breakpoint, the translated amino acid sequences may be generated for both genes in the chimeric protein, and a plot may be generated containing the remaining functional domains for each protein. A fusions characterization process may further include a process similar to that of the structural variant characterization process. Any identified fusions may include reviewing published and internally curated evidence or indicia of pathogenicity.

A B-allele frequency characterization process may include receiving the VCF and identifying heterozygous variants for loss of heterozygosity. These variants may be mined from the somatic and germline variant calls made using freebayes and pindel. B-allele frequency (BAF) deviations from the expected normal values are calculated for each heterozygous SNP, and also represented as the BAF log-odds ratio. If a variant is normal germline, the BAF deviation from normal should be close to 0. For a variant that shows LOH, BAF deviates significantly from 0. Evidence of pathogenicity based from an identified LOH or BAF deviation may be generated and reviewed in a method similar to structural variants above.

A tumor purity characterization process may be performed for oncology related disease states and may include receiving the VCF and BAF calculations to generate tumor purity estimates from somatic variants and germline B-allele frequencies, which was then refined by evaluating the likelihood of the tumor purity given the tumor-normal coverage log-ratio and B-allele frequency deviations from a normal expectation. The algorithm may iterates through a range of tumor-purities surrounding the initial estimate to return the tumor purity with the maximum likelihood.

A microsatellite instability status (MSI) characterization process may include receiving a VCF, counting the number of variants identified that are within microsatellite regions (for example, approximately 40, 50, 60, 100, 1,000 regions), and comparing that value to one or more threshold percentages. Characterization may include classifying tumors into three categories: microsatellite instability-high (MSI-H), microsatellite stable (MSS), or microsatellite equivocal (MSE). MSI testing for paired tumor-normal subjects may use reads mapped to the microsatellite loci with at least five, ten, fifteen, etc. bp flanking the microsatellite region. A minimum read threshold may be used. For example, the identification of at least 10, 20, 30, etc. mapping reads in both tumor and normal samples may be required for the locus to be included in the analysis. A minimum coverage threshold may be used. For example, At least 10, 15, 20, etc. of the total microsatellites on the panel may be required to reach the minimum coverage. Each locus may be individually tested for instability, as measured by changes in the number of nucleotide base repeats in tumor data compared to normal data, for example, using the Kolmogorov-Smirnov test. If $p \leq 0.05$, the locus may be considered unstable. The proportion of unstable microsatellite loci may be fed into a logistic regression classifier trained on samples from various cancer types, especially cancer types which have clinically determined MSI statuses, for example, colorectal and endometrial cohorts. For MSI testing in tumor-only mode, the mean and variance for the number of repeats may be calculated for each microsatellite locus. Thresholds may be set at a percentage of the normal values. For examples, MSI-H may be greater than 70%, MSE may be less than 30%, and MSS may be the values between. In another example, a vector containing the mean and variance data may be put into a support vector machine classification algorithm for artificial intelligence assisted classification. Both algorithms may return the probability of the subject being MSI-H as an output or a characterization as MSI-H, MSS, or MSE.

A Tumor mutational burden (TMB) characterization process may be receiving a VCF, identifying the number of non-synonymous mutations, and comparing the file by the megabase size of the panel (in one example, the megabase size of the sequencing panel may be 2.4 MB). In one example, non-silent somatic coding mutations, including missense, indel, and stop-loss variants, with coverage >100× and an allelic fraction >5% may be counted as non-synonymous mutations. A TMB>9 mutations per million bp of DNA may be considered "high". This threshold may be established by hypergeometric testing for the enrichment of tumors with orthogonally defined hypermutation (MSI-H) in a clinical database.

Clinical Trial & Therapy Matching

After identification and characterization of variants, a subject's sequencing results may be utilized to identify suitable clinical trials or therapies which may be relevant to the subject. Clinical trial databases and systems can be web-based resources that provide subjects, providers, physicians, researchers, and the general public with access to information on publicly and privately supported clinical studies. Often, there are a large number of clinical trials being conducted at any given time, and typically the clinical trials relate to a wide range of diseases and conditions. In some instances, clinical trials are performed at multiple sites, such as hospitals, laboratories, and universities. Each site that participates in a given clinical trial must have the proper equipment, protocols, and staff expertise, among other things. In general, each clinical trial, presents summary information about a study protocol which can include the disease or condition, the proposed intervention (e.g., the medical product, behavior, or procedure being studied, title, description, and design of the trial, requirements for participation (eligibility criteria), locations where the trial is being conducted (sites), and/or contact information for the sites.

An exemplary system for matching may curate and store the clinical trial information using structured data. The structure and organization of data (e.g., clinical trial data) improves processing efficiency and computer function. The system is capable of efficiently capturing all relevant clinical trial and subject data, including disease/condition data, trial eligibility criteria, trial site features and constraints, and/or clinical trial status (recruiting, active, closed, etc.). Once a subject's sequencing results are generated, matching and returning those trials or therapies which most closely match the subject's unique profile may be performed.

Therapies and trials matching processes may include DNA related therapy matching, clinical trial matching, and RNA related therapy matching. The therapy matching may track completion of DNA and RNA based therapy recommendations in which detected variants are matched with therapies that specifically treat those variants. Trials matching may analyze upstream variant characterization and store recommendations of clinical trials that may benefit a subject. Trial matching involves matching detected variants to clinical trials that have inclusion criteria for the specific variants.

Report Generation

An exemplary report manager process may include generating a final report, checking the quality of the report, facilitating a signout process for the report, and delivering the report to an ordering physician. More specifically, the report manager process brings together the results from each testing/characterization "branch" (e.g., DNA, RNA, IHC, each having variant detections from SNV, MNP, InDels, Fusions, TMB, MSI, etc.) and causes references from one branch to the other where appropriate to generate data needed to develop a final report. Report manager process may then facilitate data error checking to ensure that all needed report branches exist and have passed quality control. The manager process may create an unpopulated shell report based on order objectives or test types performed and populate information from the report based on the results of a bioinformatics pipeline, for example, the order processing pipeline, below.

Normalization Platform

The system may include a normalization platform to normalize laboratory data to a data standard. The laboratory data may be data from the laboratory 140, from other laboratories, or from other system. The data standard may be a standard established by the operator of the system, by a regulatory organization, or by another party. The data standard may be defined with reference to one or more laboratory features. For instance, the data standard may be defined with reference to filters, cut-offs, thresholds, or other design features. The design features may be targeted towards specific subject populations, specific conditions, specific diseases, or the like.

In one example, the normalization platform permits normalization of data between different runs of the laboratory.

In another example, the normalization platform permits normalization of data between data from the laboratory 140 and an external laboratory's data.

In another example, the normalization platform permits normalization of data from the laboratory 140 with an external data standard.

In another example, the normalization platform permits normalization of data from an external laboratory with regulatory design specifications. For instance, the system may receive FASTQ/BAM molecular pathology files from an external laboratory. The system may provide those files to the normalization platform. Where the normalization platform is further provided with a first set of regulatory design specifications and a second set of design filters (such as cut-off, filter, threshold, or other design features) of the external laboratory, the normalization system may be able to adjust the FASTQ/BAM file results using such design features in order to generate revised file results that are consistent with the regulatory design specifications.

In addition to normalization of data from a laboratory, the normalization platform may also provide for normalization of data from a bioinformatics pipeline or other component.

Deconvolution Platform

Deconvoluting sequencing results, laboratory testing results, and other results may include receiving wet lab results from the above types of laboratories and sending them to PCR, artificial intelligence engines implementing one or more machine learning models and/or neural networks, regressing sequencing profiles from the combined sequencing results, and other methods known to those skilled in the art. A platform for performing this may include processing a single deconvolution alone, processing a plurality of deconvolutions in parallel, and comparing deconvoluted results with a stacked model. Deconvolution may be performed as a clean-up step to generating raw sequencing results, a normalization method prior to providing sequencing results to a bioinformatics pipeline, or as an analysis step during the completion of a sequencing result analysis for generating a report on the genomic portfolio if a specimen. Deconvolution methods are discussed extensively in U.S. patent application Ser. No. 16/732,229, titled "Transcriptome Deconvolution Of Metastatic Tissue Samples" and filed Dec. 31, 2019, which is incorporated by reference in its entirety for all purposes.

Order processing Pipeline

Next generation sequencing, such as the wet lab process, variant calling, variant characterization, clinical trial and therapies matching, and report generation may be performed for one or more disease states as a part of sequencing the genome of a subject. In one embodiment, next generation sequencing may be performed for subjects having a disease state of cancer, such as an oncological subject order processing pipeline.

Figure 7:
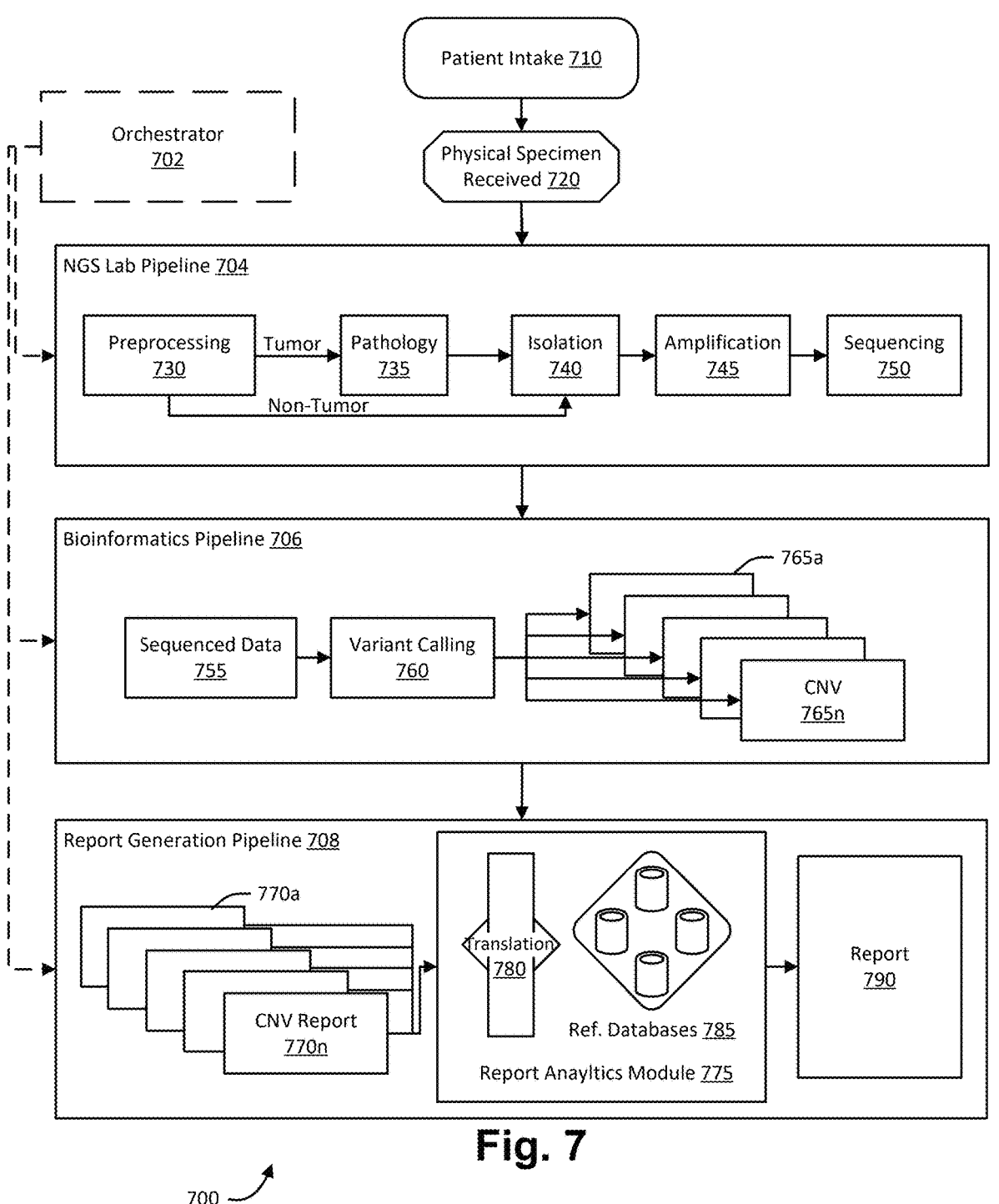
FIG. 7 is a block diagram illustration of a patient order processing pipeline in which embodiments of the present invention may operate.

FIG. 7 is a block diagram illustrating an oncological subject order processing pipeline 700 in which embodiments of the present invention may operate. The subject order processing pipeline 700 may provide the processing flow for a subject order from inception, NGS, variant calling, report processing, and generation, through reporting the results of NGS to the ordering physician. An orchestration module or software such as orchestrator 702 may guide the processing of each of the blocks and elements contained in the pipeline 700 to ensure efficient processing with little downtime in between stages and no missed steps by providing signals to each of NGS lab pipeline 704, bioinformatics pipeline 706, and report generation pipeline 708 directing current states and processing in each.

A subject may be received, such as from a sequencing order received from a physician, and sent to subject Intake 710, where the subject's clinical data may be entered and information detailing the type of sequencing and reporting that the physician is requesting may be stored in a system. The order as entered into the system may provide the orchestrator 702 with a series of steps which are to be performed during the processing of the subject sequencing order.

The process from which this may be performed may then rely on establishing a sample of the subjects DNA. Herein, a sample may be sent to block 720 when the sample is received at the laboratory performing the sequencing.

For cancer treatment, this may be a cancer sample, such as a sample of tumor tissue, and a sample of the subject's saliva or blood. For treatments of other diseases, this may be a sample of saliva or blood only. For cancer treatments, a sample of a tumor may originate from a biopsy (such as a needle aspiration or physical site extraction). Biopsies are inherently messy affairs where a biopsy may generally acquire an indeterminate proportion of cells, such as healthy cells and tumor cells which are sequenced together.

An NGS Lab Pipeline 704 may receive the samples and process the samples for sequencing. A pre-processing stage 730 may include the laboratory identifying each and every sample received for a particular specimen, generating a label for the samples, the slides of those samples, and other accessioning tasks to enable the tracking of the samples through the pipeline 700.

During preprocessing, some samples may be identified as tumor samples, a pathology stage 735 may be activated to identify the type of cells in the sample and a proportion of these types of cells to each other. During the pathology stage 735, a pathologist may review slides of cells extracted from the sample. In another embodiment, a machine learning algorithm which has been trained on the pathology results from similar types of slides may be applied to new slides to either aid the pathologist in making a determination or to replace the pathologist and provide a determination without the oversight of the pathologist. In alternative embodiments, the samples received at stage 720 may include slides acquired and prepared by the ordering physician.

When preprocessing identifies other samples as non-tumor samples such as a blood or saliva sample for germline sequencing, the pathology stage 735 may be bypassed all together as the steps of identifying the type of cells and the proportion of those cells on the slide are not necessary. An assumption that non-tumor cells samples are "pure" non-tumor may be made.

An isolation stage 740 may receive a sample of cells from either the tumor or non-tumor sample and isolate either the DNA or the RNA from the sample. DNA may be isolated by destroying any RNA present in the sample and, similarly, RNA may be isolated by destroying any DNA present in the sample.

An amplification stage 745 may receive the isolated DNA or RNA and amplify the respective sample such that the provide RNA or DNA is copied over and over to improve the potential read results that may be made by the sequencer. Polymerase chain reaction (PCR) is a method may be employed to make many copies of a specific DNA/RNA segment. Using PCR, a single copy (or more) of a DNA sequence is linearly or exponentially amplified to generate thousands to millions of more copies of that particular DNA segment.

Sequencing may be performed on the amplified samples at the sequencing stage 750, a NGS sequencing, such as illumina's iSeq, MiniSeq, MiSeq, or NextSeq Systems; Ion PGM, Proton, or GeneStudio Systems; or comparable NGS systems from Pacific Biosciences, Roche 454, or SOLID may be used. The sequencing stage may output sequencing data containing reads from probes such as in a raw data FASTQ format, raw data FASTA format, a Binary Alignment Map format (BAM), Sequence Alignment Map format (SAM) or other raw or aligned file formats. In one example, the SAM or BAM files may list all genetic sequences identified in a sample, the count for each sequence, and the location of each sequence read with respect the complete genome. In one example, a second set of SAM or BAM files may be included for listing all genetic sequences identified in a normal, non-cancer sample collected from the same subject as the cancer sample. The sequencing stage may further output an index file for each SAM or BAM file, indicating the file location of each read within the SAM or BAM file. In one example, an index file for a BAM file contains a table or list of all reads found in the BAM file and the file location of each read within the BAM file. In one example in the index file, each read may be labeled by a read ID (for example, read A, read B, etc. or read 1, read 2, etc.), by the sequence of the read, or by the chromosome and/or nucleotide position within the chromosome of the sequence of the read. The file location of the read may be listed as a line number within the BAM file.

A bioinformatics pipeline 706 may receive the sequencing results generated from sequencing stage 750 or results translated from a raw to an aligned format at sequenced data stage 755. In another embodiment, sequenced data stage 755 may receive sequencing results in a raw format and perform filtering and/or alignment to generate an aligned format. Filtering may include detecting spurious or incorrect reads and removing them from the dataset. The bioinformatics pipeline 706 may access resource files such as one or more pool files containing reads from one or many normal samples. Resource files may include a published reference genome such as human reference genome 19 (hg19) or human reference genome 38 (hg38), etc. Resource files may further include a blacklist file containing a list of blacklist regions and/or genes in the genome for which CNV calculation is less likely to be accurate or a whitelist file containing a list of whitelist regions and/or genes in the genome which should be incorporated into the CNV analysis. Any decreased accuracy of CNV calculation for blacklisted regions may be due to the genetic analysis technique used to identify genetic sequences in a sample. For example, if the genetic analysis technique requires genetic probes to bind to nucleic acid molecules isolated and/or copied from a sample, the probes binding to a blacklist region may bind in an inconsistent manner. A blacklist region may bind to probes less frequently than a typical region or may be saturated with bound probes. Another reference file may include a target file for enumerating the list of target genes, variants, or regions. The bioinformatics pipeline 706 may incorporate the enumerated list of targets and implement the pipeline staged for one or more targets in the list of targets.

A variant calling stage 760 may identify variants in the sequencing data of 755 by identifying reads for each variant based upon variant location, length, and/or depth. Variants may be portions of genetic sequences in the cancer sample which do not exist in the normal sample, and/or which do not exist in a reference genome or database of normal sequences. Variant information for each variant may include the variant's location, the normal nucleotide sequence seen in the reference genome at that position, and the variant nucleotide sequence seen in the sample. The variant location may include a chromosome number and a nucleotide position number to differentiate nucleotide positions that are located in the same chromosome. Reads may be compared to a reference genome to identify normal reads and/or variants. The number of reads for each variant may be counted, and the aggregate count for all identified variants may be stored in a Variant Call Format (VCF) or comma-separated values (CSV) that specifies the format of a text file used in bioinformatics for storing gene sequence variations. By storing the variant calls in VCF only the variations need to be stored and a reference genome may be utilized to identify each variant of the VCF.

A VCF or comparable variant calling output may be provided to one or more stages 765a-n. Stages 765a-n may provide specialized testing for one or more of tumor mutational burden (TMB), microsatellite instability (MSI), gene fusions, single nucleotide variants (SNV) and somatic/indel mutations, and CNV 765n detections. Each of these stages may receive a VCF file and perform analytics of the variants therein to identify the respective TMB, MSI, gene fusion, SNV, Indel, or CNV states and generate output files for report parsing, interpretation, and generation.

Validation may be performed at stage 767, validation may be manual review by a variant scientist, or similarly educated and trained personnel or be handled in an automatic fashion. Automation may be performed using a rule set or a machine learning algorithm such that variants may be passed through the pipeline upon satisfaction of one or more constraints imposed by the rule set or machine learning algorithm.

A report generation pipeline 708 may receive the output files from each of stages 765a-n at report stages 770a-n. Reports 770a-n may then be provided to report analytics module 775 for generating analysis of the respective reports against databases of pharmacogenomic and cohort effects. For example, a cohort of subjects may be maintained comprising the clinical and molecular medical information of all subjects whose DNA or RNA have been sequenced. This cohort may be filtered according to common features with the instant subject (such as demographic, clinical, or molecular features) and trends within the cohort may be analyzed to generate predictions for the instant subject's pharmacogenomic response to medications/treatments or type of cancer or disease state determination. These predictions may be summarized for inclusion in a report, such as report 790. Furthermore, for each of the reports 770a-n, additional databases 785 may be referenced to identify insights that may be ascertained from the subject's TMB, MSI, gene fusion, SNV, MNV, InDel, CNV, or other characterization states. These additional references databases 785 may be stored in many different formats depending on the institution that curated the database. It may be necessary to maintain a translation process 780 which may recognize key terms from each of reports 770a-n and translate these key terms to a format which may be recognized in one or more of the reference databases 785. A CNV in report 770n, may be referenced according to a table of variants. There are several resources for common gene and variant identifiers, such as the Human Genome Organisation (HUGO) Gene Nomenclature Committee (HGNC) or the National Center for Biotechnology Information (NCBI) with the Entrez list. The HGNC approves a unique and meaningful name for every known human gene. Such a table may include, for each CNV: an identifier to an Entrez Gene or an HGNC Gene or in which the variant was detected; the gene symbol of the gene in which the variant was detected; a copy state indicator of a copy number gain, copy number loss, or conflict; an message-digest checksum (such as MD5) of the values for a string, such as <entrezId><state> or <hgncId><state>, to serve as the primary key of the table; copy number region aggregations that determined the copy state; one or more indicators of a loss of function (LOF), gain of function (GOF), amplification (AMP), or gene fusion (FUS); a flag indicating whether the variant is therapeutically actionable based on known references; an overall reportability classification determined for the CNV such as "Reportable", "Not Reportable", or "Conflicting Evidence"; a unique identifier of the scientist who confirmed the classification of the CNV; a timestamp of when the scientist made the confirmation; and the classification of relevance for the CNV as being in a gene of therapeutic relevance such as "True", "False", or "Indeterminate." Similar steps may be performed for each of the variant characterizations, above.

An Entrez Gene Id (GeneID) is a representation of gene-specific information at the National Center for Biotechnology Information (NCBI). The information conveyed by establishing the relationship between sequence and a GeneID is used by many NCBI resources. For example, the names associated with GeneIDs are used in resource/reference databases HomoloGene, UniGene and RefSeqs. These relationships may further the capabilities of translation 780 by providing additional reference points between these and other external databases. A loss of function mutation (LOF above), also called inactivating mutations, is the result in the gene product having less or no function whereas the GOF is the opposite result where function is gained due to the gene mutation. A classification of a CNV as "Reportable" means that the CNV has been identified in one or more reference databases as influencing the tumor cancer characterization, disease state, or pharmacogenomics, "Not Reportable" means that the CNV has not been identified as such, and "Conflicting Evidence" means that the CNV has both evidence suggesting "Reportable" and "Not Reportable." Furthermore, a classification of therapeutic relevance is similarly ascertained from any reference datasets mention of a therapy which may be impacted by the detection (or non-detection) of the CNV. Similar classification steps may be performed for each of the variant characterizations, above.

For example, a variant may be identified in a CNV report as having a count twenty times that of normal. However, a database in the reference database may not recognize the variant as encoded in the CNV report 770n and the translation process 780 may translate the variant representation from that of the report to one which is recognized by the database to link the report with meaningful analytic information from the database. Report analytics module 775 may process each of the identified variant calls, TMB, MSI, gene fusion, SNV, InDel, CNV, or other states through the reference databases 785 to ascertain report indicia worth reporting to the ordering physician and summarize the report indicia in report 790 which is to be provided to the ordering physician.

An orchestrator 702 may coordinate the timing for each of the above identified steps. For example, NGS pipeline 704 may not be initiated until subject intake 710 has been successfully completed, bioinformatics pipeline 706 may not be initiated until sequencing 750 has successfully completed, and each of the report analytics for reports 770a-n may be started in turn as specialized testing stages 765a-n each complete. In addition, a notification to the ordering physician that report 790 is available for view may not be generated until all of reports 770a-n have each been successfully analyzed against the reference databases 785 and the report is completely generated.

In one embodiment, aspects of the variant characterization and generation of predictions from subject data may be performed by an artificial intelligence engine, such as a system for generating and modeling predictions of subject objectives.

Figure 8:
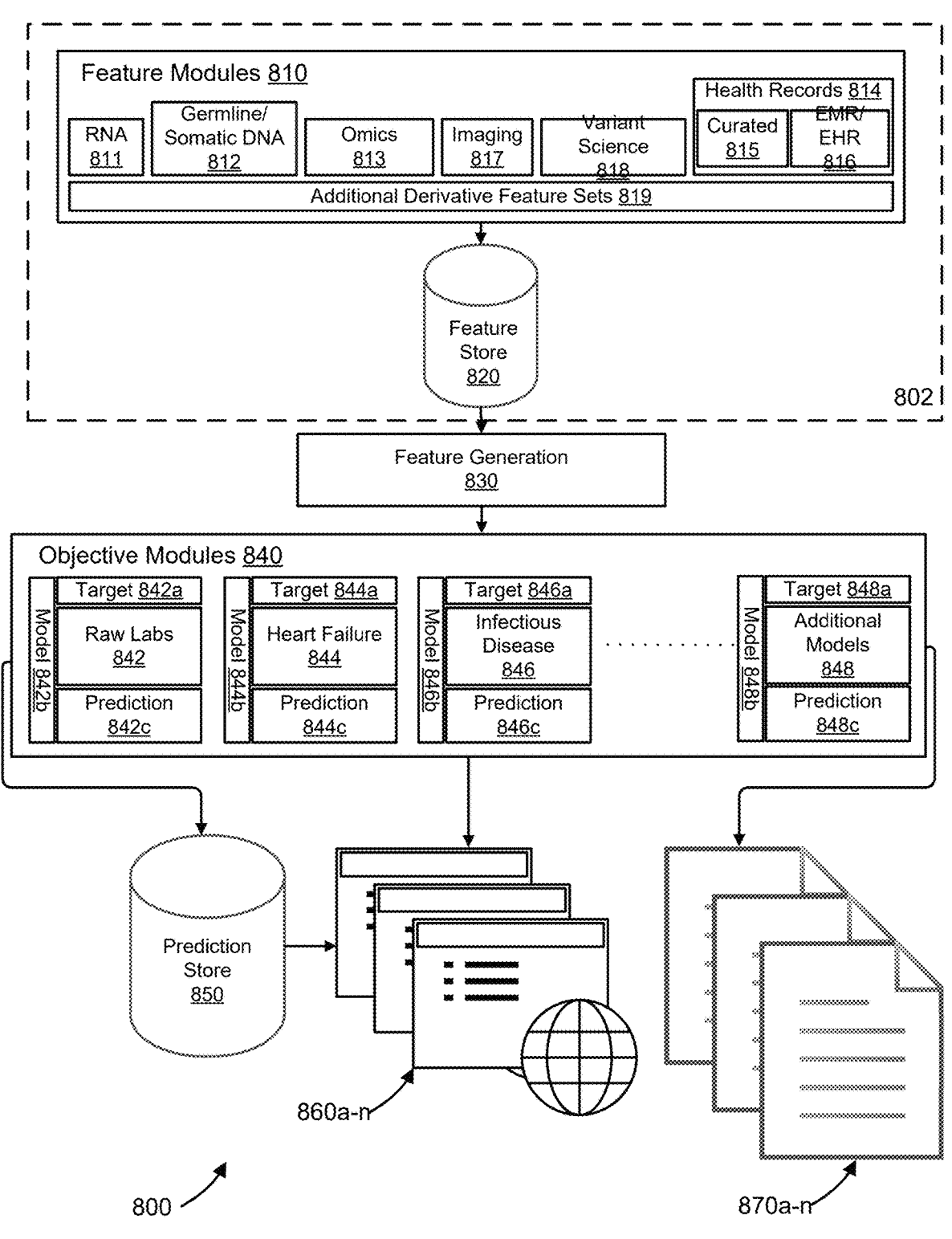
FIG. 8 is an illustration of a block diagram illustrating a system for generating predictions of an objective from a plurality of patient features, in accordance with some embodiments of the present disclosure.

FIG. 8 illustrates an embodiment of a computer-implemented system 800 for generating and modeling predictions of subject objectives, such as the incorporation of patient specific parameters into the generation of a report for a patient lab result. Predictions may be generated from subject information represented by feature modules 810 implemented by the system architecture 802. The system 800 can be a content server (also referred to as a prediction engine), which is hardware or a combination of both hardware and software. A user, such as a health care provider or subject, is given remote access through the GUI to view, update, and analyze information about a subject's medical condition using the user's own local device (e.g., a personal computer or wireless handheld device). A user can interact with the system to instruct it to generate electronic records, update the electronic records, and perform other actions. The content server is configured to receive various information in different formats and it converts the information into the standardized format that is suitable for processing by modules operation on or in conjunction with the content server. Thus, information acquired from subjects' electronic medical records (EMR), unstructured text, genetic sequencing, imaging, and various other information can be converted into features that are used for training a plurality of machine-learning models.

The information acquired, processed, and generated by the content server 800 is stored on one or more of the network-based storage devices. The user can interact with the content server to access the information stored in the network-based storage devices, and the content server can receive user-supplied information, apply the one or more models stored in the network-based storage to the information, and to provide, in an electronic form, results of the model application to the user on a graphical user interface of the user device. The electronic information is transmitted in a standardized format over the computer network to the users that have access to the information. In this way, the users can readily adapt their medical diagnostic and treatment strategy in accordance with the system's predictions which can be automatically generated. Moreover, the system generates recommendations to users regarding subject diagnosis and treatment.

In some embodiments, the described systems and methods are implemented as part of a digital and laboratory health care platform. The platform may automatically generate a molecular report as part of a targeted medical care precision medicine treatment. In some embodiments, the system in accordance with embodiments of the present disclosure operates on one or more micro-services, which can be micro-services of an order management system. In some embodiments, the system is implemented in conjunction with one or more micro-services of a cell-type profiling service.

The feature modules 810 may store a collection of features, or status characteristics, generated for some or all subjects whose information is present in the system 800. These features may be used to generate and model predictions using the system 800. While feature scope across all subjects is informationally dense, a subject's feature set may be sparsely populated across the entirety of the collective feature scope of all features across all subjects. For example, the feature scope across all subjects may expand into the tens of thousands of features, while a subject's unique feature set may include a subset of hundreds or thousands of the collective feature scope based upon the records available for that subject.

A plurality of features present in the feature modules 810 may include a diverse set of fields available within subject health records 814, including information contained in the source subject, structured subject, structured clinomic data repository, and laboratory datasets, above. Clinical information may be based upon fields which have been entered into an electronic medical record (EMR) or an electronic health record (EHR) 816, which can be done automatically or manually, e.g., by a physician, nurse, or other medical professional or representative. Other clinical information may be curated information (815) obtained from other sources, such as, for example, genetic sequencing reports (e.g., from molecular fields). Sequencing may include next-generation sequencing (NGS) and may be long-read, short-read, or other forms of sequencing a subject's somatic and/or normal genome. A comprehensive collection of features in additional feature modules may combine a variety of features together across varying fields of medicine which may include diagnoses, responses to treatment regimens, genetic profiles, clinical and phenotypic characteristics, and/or other medical, geographic, demographic, clinical, molecular, or genetic features. For example, as shown in FIG. 8, a subset of features may comprise molecular data features, such as features derived from an RNA feature module 811 or a DNA feature module 812 sequencing.

As further shown in FIG. 8, another subset of features, imaging features from imaging feature module 817, may comprise features identified through review of a specimen by pathologist, such as, e.g., a review of stained H&E or IHC slides. As another example, features may include echocardiogram (ECG) testing results having a plurality of leads and voltage information corresponding to reads from a patient's ECG, corresponding diagnosis, treatments, and outcomes. As another example, a subset of features may comprise derivative features obtained from the analysis of the individual and combined results of such feature sets. Features derived from DNA and RNA sequencing may include genetic variants from variant science module 818, which can be identified in a sequenced sample. Further analysis of the genetic variants present in variant science module 818 may include steps such as identifying single or multiple nucleotide polymorphisms, identifying whether a variation is an insertion or deletion event, identifying loss or gain of function, identifying fusions, calculating copy number variation, calculating microsatellite instability, calculating tumor mutational burden, or other structural variations within the DNA and RNA. Analysis of slides for H&E staining or IHC staining may reveal features such as tumor infiltration, programmed death-ligand 1 (PD-L1) status, human leukocyte antigen (HLA) status, or other immunology-related features.

Features derived from structured, curated, and/or electronic medical or health records 814 may include clinical features such as diagnosis, symptoms, therapies, outcomes, subject demographics such as subject name, date of birth, gender, ethnicity, date of death, address, smoking status, diagnosis dates for cancer, illness, disease, diabetes, depression, other physical or mental maladies, personal medical history, family medical history, clinical diagnoses such as date of initial diagnosis, date of metastatic diagnosis, cancer staging, tumor characterization, tissue of origin, treatments and outcomes such as line of therapy, therapy groups, clinical trials, medications prescribed or taken, surgeries, radiotherapy, imaging, adverse effects, associated outcomes, genetic testing and laboratory information such as performance scores, lab tests, pathology results, prognostic indicators, date of genetic testing, testing provider used, testing method used, such as genetic sequencing method or gene panel, gene results, such as included genes, variants, expression levels/statuses, or corresponding dates associated with any of the above.

As shown in FIG. 8, features 813 may be derived from information from additional medical or research based Omics fields including proteome, transcriptome, epigenome, metabolome, microbiome, and other multi-omic fields. Features derived from an organoid modeling lab may include the DNA and RNA sequencing information germane to each organoid and results from treatments applied to those organoids. Features 817 derived from imaging data may further include reports associated with a stained slide, size of tumor, tumor size differentials over time including treatments during the period of change, as well as machine learning approaches for classifying PDL1 status, HLA status, or other characteristics from imaging data. Other features may include additional derivative features sets 819 derived using other machine learning approaches based at least in part on combinations of any new features and/or those listed above. For example, imaging results may need to be combined with MSI calculations derived from RNA expressions to determine additional further imaging features. As another example, a machine learning model may generate a likelihood that a subject's cancer will metastasize to a particular organ or a subject's future probability of metastasis to yet another organ in the body. Additional derivative feature sets are discussed in more detail below with respect to FIG. 9. Other features that may be extracted from medical information may also be used. There are many thousands of features, and the above-described types of features are merely representative and should not be construed as a complete listing of features.

In addition to the above features and enumerated modules, the feature modules 810 may further include one or more of the modules that are described below and that can be included within respective modules of the Feature modules 810, as a sub-module or as a standalone module.

Continuing with FIG. 8, a germline/somatic DNA feature module 812 may comprise a feature collection associated with the DNA-derived information of a subject and/or a subject's tumor. These features may include raw sequencing results, such as those stored in FASTQ, BAM, VCF, or other sequencing file types known in the art; genes; mutations; variant calls; and variant characterizations. Genomic information from a subject's normal sample may be stored as germline and genomic information from a subject's tumor sample may be stored as somatic.

An RNA feature module 811 may comprise a feature collection associated with the RNA-derived information of a subject, such as transcriptome information. These features may include, for example, raw sequencing results, transcriptome expressions, genes, mutations, variant calls, and variant characterizations. Features may also include normalized sequencing results, such as those normalized by TMP.

The feature modules 810 can comprise various other modules. For example, a metadata module (not shown) may comprise a feature collection associated with the human genome, protein structures and their effects, such as changes in energy stability based on a protein structure.

A clinical module (not shown) may comprise a feature collection associated with information derived from clinical records of a subject, which can include records from family members of the subject. These may be abstracted from unstructured clinical documents, EMR, EHR, or other sources of subject history. Information may include subject symptoms, diagnosis, treatments, medications, therapies, hospice, responses to treatments, laboratory testing results, medical history, geographic locations of each, demographics, or other features of the subject which may be found in the subject's medical record. Information about treatments, medications, therapies, and the like may be ingested as a recommendation or prescription and/or as a confirmation that such treatments, medications, therapies, and the like were administered or taken.

An imaging module, such as, e.g., the imaging module 817, may comprise a feature collection associated with information derived from imaging records of a subject. Imaging records may include H&E slides, IHC slides, radiology images, and other medical imaging information, as well as related information from pathology and radiology reports, which may be ordered by a physician during the course of diagnosis and treatment of various illnesses and diseases. These features may include TMB, ploidy, purity, nuclear-cytoplasmic ratio, large nuclei, cell state alterations, biological pathway activations, hormone receptor alterations, immune cell infiltration, immune biomarkers of MMR, MSI, PDL1, CD3, FOXP3, HRD, PTEN, PIK3CA; collagen or stroma composition, appearance, density, or characteristics; tumor budding, size, aggressiveness, metastasis, immune state, chromatin morphology; and other characteristics of cells, tissues, or tumors for prognostic predictions.

An epigenome module, such as, e.g., an epigenome module from Omics module 813, may comprise a feature collection associated with information derived from DNA modifications which are not changes to the DNA sequence and regulate the gene expression. These modifications can be a result of environmental factors based on what the subject may breathe, eat, or drink. These features may include DNA methylation, histone modification, or other factors which deactivate a gene or cause alterations to gene function without altering the sequence of nucleotides in the gene.

A microbiome module, such as, e.g., a microbiome module from Omics module 813, may comprise a feature collection associated with information derived from the viruses and bacteria of a subject. These features may include viral infections which may affect treatment and diagnosis of certain illnesses as well as the bacteria present in the subject's gastrointestinal tract which may affect the efficacy of medicines ingested by the subject.

A proteome module, such as, e.g., a proteome module from Omics module 813, may comprise a feature collection associated with information derived from the proteins produced in the subject. These features may include protein composition, structure, and activity; when and where proteins are expressed; rates of protein production, degradation, and steady-state abundance; how proteins are modified, for example, post-translational modifications such as phosphorylation; the movement of proteins between subcellular compartments; the involvement of proteins in metabolic pathways; how proteins interact with one another; or modifications to the protein after translation from the RNA such as phosphorylation, ubiquitination, methylation, acetylation, glycosylation, oxidation, or nitrosylation.

Additional Omics module(s) (not shown) may also be included in Omics module 813, such as a feature collection associated with all the different field of omics, including: cognitive genomics, a collection of features relating to the changes in cognitive processes associated with genetic profiles; comparative genomics, a collection of features relating to the relationship of genome structure and function across different biological species or strains; functional genomics, a collection of features relating to gene and protein functions and interactions including transcriptomics; interactomics, a collection of features comprising the study relating to large-scale analyses of gene-gene, protein-protein, or protein-ligand interactions; metagenomics, a collection of features relating to metagenomes such as genetic material recovered directly from environmental samples; neurogenomics, a collection of features relating to genetic influences on the development and function of the nervous system; pangenomics, a collection of features relating to the entire collection of gene families found within a given species; personal genomics, a collection of features relating to genomics concerned with the sequencing and analysis of the genome of an individual such that once the genotypes are known, the individual's genotype can be compared with the published literature to determine likelihood of trait expression and disease risk to enhance personalized medicine suggestions; epigenomics, a collection of features relating to supporting the structure of genome, including protein and RNA binders, alternative DNA structures, and chemical modifications on DNA; nucleomics, a collection of features relating to the complete set of genomic components which form the cell nucleus as a complex, dynamic biological system; lipidomics, a collection of features relating to cellular lipids, including the modifications made to any particular set of lipids produced by a subject; proteomics, a collection of features relating to proteins, including the modifications made to any particular set of proteins produced by a subject; immunoproteomics, a collection of features relating to large sets of proteins involved in the immune response; nutriproteomics, a collection of features relating to identifying molecular targets of nutritive and non-nutritive components of the diet including the use of proteomics mass spectrometry data for protein expression studies; proteogenomics, a collection of features relating to biological research at the intersection of proteomics and genomics including data which identifies gene annotations; structural genomics, a collection of features relating to 3-dimensional structure of every protein encoded by a given genome using a combination of modeling approaches; glycomics, a collection of features relating to sugars and carbohydrates and their effects in the subject; foodomics, a collection of features relating to the intersection between the food and nutrition domains through the application and integration of technologies to improve consumer's well-being, health, and knowledge; transcriptomics, a collection of features relating to RNA molecules, including mRNA, rRNA, tRNA, and other non-coding RNA, produced in cells; metabolomics, a collection of features relating to chemical processes involving metabolites, or unique chemical fingerprints that specific cellular processes leave behind, and their small-molecule metabolite profiles; metabonomics, a collection of features relating to the quantitative measurement of the dynamic multiparametric metabolic response of cells to pathophysiological stimuli or genetic modification; nutrigenetics, a collection of features relating to genetic variations on the interaction between diet and health with implications to susceptible subgroups; cognitive genomics, a collection of features relating to the changes in cognitive processes associated with genetic profiles; pharmacogenomics, a collection of features relating to the effect of the sum of variations within the human genome on drugs; pharmacomicrobiomics, a collection of features relating to the effect of variations within the human microbiome on drugs; toxicogenomics, a collection of features relating to gene and protein activity within particular cell or tissue of an organism in response to toxic substances; mitointeractome, a collection of features relating to the process by which the mitochondria proteins interact; psychogenomics, a collection of features relating to the process of applying the powerful tools of genomics and proteomics to achieve a better understanding of the biological substrates of normal behavior and of diseases of the brain that manifest themselves as behavioral abnormalities, including applying psychogenomics to the study of drug addiction to develop more effective treatments for these disorders as well as objective diagnostic tools, preventive measures, and cures; stem cell genomics, a collection of features relating to stem cell biology to establish stem cells as a model system for understanding human biology and disease states; connectomics, a collection of features relating to the neural connections in the brain; microbiomics, a collection of features relating to the genomes of the communities of microorganisms that live in the digestive tract; cellomics, a collection of features relating to the quantitative cell analysis and study using bioimaging methods and bioinformatics; tomomics, a collection of features relating to tomography and omics methods to understand tissue or cell biochemistry at high spatial resolution from imaging mass spectrometry data; ethomics, a collection of features relating to high-throughput machine measurement of subject behavior; and videomics, a collection of features relating to a video analysis paradigm inspired by genomics principles, where a continuous digital image sequence, or a video, can be interpreted as the capture of a single image evolving through time of mutations revealing subject insights.

In some embodiments, a robust collection of features may include all of the features disclosed above. However, predictions based on the available features may include models which are optimized and trained from a selection of fewer features than in an exhaustive feature set. Such a constrained feature set may include, in some embodiments, from tens to hundreds of features. For example, a prediction may include predicting the likelihood a subject's acceptable base A1C is higher than normal estimates. A model's constrained feature set may include the genomic results of a sequencing of the subject's specimen such as saliva, blood, stool, or tissue, derivative features based upon the genomic results, the subject's past A1C testing results, the subject's age, gender, and race, and symptoms that the subject brought to their physicians attention during a routine checkup. While the prediction was illustrated with A1C, all of the laboratory testing outlined herein may be substituted to generate predictions of the subject's personal laboratory testing metrics.

The feature store 820 may enhance a subject's feature set through the application of machine learning and/or an artificial intelligence engine and analytics by selecting from any features, alterations, or calculated output derived from the subject's features or alterations to those features. One method for enhancing a subject's feature set may include dimensionality reduction, such as collapsing a feature set from tens of thousands of features to a handful of features. Performing dimensionality reduction without losing information may be approached in an unsupervised manner or a supervised manner. Unsupervised methods may include RNA Variational Auto-encoders, SVD, PCA, KernelPCA, SparsePCA, DictionaryLearning, Isomap, NMF, UMAP, Feature agglomeration, subject correlation clustering, KMeans, Gaussian Mixture, or Spherical KMeans. Performing dimensionality reduction in a supervised manner may include Linear Discriminant Analysis, Neighborhood Component Analysis, MLP transfer learning, or tree based supervised embedding.

In one embodiment, a grid search may be performed across a variety of encoding, such as the supervised and unsupervised approaches above, where each encoding is evaluated across a variety of hypertuning parameters to identify the encoding and hyperparameter set which generates the highest dimensionality reduction while retaining or improving accuracy.

In one embodiment, a grid search may identify a dimensionality reduction implemented with tree-based supervised embedding on RNA TPM feature sets for all subjects. RNA TPM feature sets may be fit to a forest of decision trees, Such as a forest of decision trees generated from hyperparameters of minimum samples per leaf using a minimum number of 2, 4, 8, 16, 24, 100, or other selected number, a maximum feature set using a percentage of the features which should be used in each tree, the number of trees to be used in the forest, and the number of clusters which may be identified from the reduced dimensionality data set. Each tree in the forest may randomly select up to the threshold percentage of features and with each selected feature identify the largest split between subjects who have metastasis and do not have metastasis. When the feature set includes RNA TPM features, a random selection of genes may include identifying which genes are the most divisive of the random set of selected features, starting the branching from the most divisive gene and successively iterating down the gene list until either the minimum samples per leaf are not met or the maximum features are met. The leaf nodes for each tree include subjects who meet the criteria at each branch and are correlated based upon their likelihood to metastasize. Subject membership of each leaf may be evaluated using one-hot KMeans cluster membership counts or a distance of each subject to each of the KMeans centroids/clusters. In an example, the leafs of each tree are compared to identify which leaves include the same branches or equivalent branches, such as branches that result in the same subjects because the genes, while different, are equivalent to each other. Equivalency may be determined when information related to the expression level of a gene may be correlated with, or predicted from, the expression level data associated with one or more other genes. When a gene may be correlated with, or predicted from, one or more other genes, the one or more other genes are defined as proxy genes. The terms proxy genes and equivalent genes may be used interchangeably herein. Identifying the number of same branches, or equivalent branches, for each leaf allows generation of membership for each leaf as it occurs within the individual trees of the forest. Similarly, when KMeans clusters are generated from the collection of leafs, a distance for each subject may be calculated for each subject. An array may be generated having the normalized inverse of each distance for each subject to each KMeans centroid. The array, at this point, may be stored as a reduced dimensionality feature set of RNA TPM features for the set of subjects, and the features of reduced dimensionality may be used in any of the predictive methods described herein. In other words, the methods for identifying a prediction of a target/objective pair may be performed having the array of distances for each subject as an input into the artificial intelligence engine described below; including, for example, performing logistic regression to generate a predictive model for a target/objective pair.

The feature store 820 may generate new features from the original features found in feature module 810 or may identify and store insights or analysis derived using the features. The selections of features may be based upon an alteration or calculation to be generated, and may include the calculation of single or multiple nucleotide polymorphisms, insertion or deletions of the genome, a tumor mutational burden, a microsatellite instability, a copy number variation, a fusion, or other such calculations. In an example, an output of an alteration module which may inform future alterations or calculations may include a finding that subjects having hypertrophic cardiomyopathy (HCM) express variants in MYH7 more commonly than subjects without HCM. An exemplary approach may include the enrichment of variants and their respective classifications to identify a region in MYH7 that is associated with HCM. Any novel variants detected from subject's sequencing localized to this region would increase the subject's risk for HCM. Therefore, features which may be utilized in such an alteration detection include the structure of MYH7, the normal genome for MYH7, and classification of variants therein as impacting a subject's chances of having HCM. A model which focuses on enrichment may isolate such variants. Other variants may be isolated with respect to other illness, diseases, or diagnosis through an enrichment alteration module. The feature store selection, alteration, and calculations is discussed below in more detail with respect to FIG. 9.

The feature generation 830 may process features from the feature store 820 by selecting or receiving features from the feature store 820. The features may be selected based on a subject by subject basis, a target/objective by subject basis, or a target/objective by all subject basis, or a target/objective by cohort basis. In the subject by subject basis, features which occur a specified subject's timeline of medical history may be processed. In the target/objective by subject basis, features which occur in a specified subject's timeline which inform an identified target/objective prediction may be processed. In some examples, a model may be selected which optimizes the prediction based upon the features available to the prediction engine at the time of processing/generating a prediction for the subject or a prediction for all of the subjects. Targets/objectives may include a combination of an objective and a horizon, or time period, such as personalizing diagnostic testing results at the instant testing period, predicting the effect of smoking on the testing results in the next 6 months, predicting the impact a clinical feature (age, ethnicity, DNA mutations, loss of kidney or liver, current medication, CT/MRI/x-ray imaging results, etc.) has on the instant testing results. Some horizons may extend over future tests too, such as testing within 1 week to one year. The above listing of targets/objectives is not exhaustive, other objectives and horizons may be used based upon the predictions requested from the system. In one example, the prediction may be represented as P(Y(t)|X), where P is the probability of developing a metastasis in organ Y at time t given the subject's current medical state and history X. Where the P includes a target/objective, the X includes the subject features in the system. In the target/objective by all-subject basis, features which occur in each subject's timeline which inform an identified target/objective prediction may be processed for each subject until all subjects have been processed. In the target/objective by cohort basis, features which occur in each subject's timeline which inform an identified target prediction may be processed for each subject until all subjects of a cohort have been processed. A cohort may include a subset of subjects having attributes in common with each other. For example, a cohort may be a collection of subjects which share a common institution (such as a hospital or clinic), a common diagnosis (such as cancer, depression, heart failure, or other illness such as disease states identified herein), a common treatment (such as a medication or therapy), or common molecular characteristics (such as a genetic variation or alteration). Cohorts may be derived from any feature or characteristic included in the feature modules 810 or feature store 820. Feature generation may provide a prior feature set and/or a forward feature set to a respective objective module corresponding to the target/objective and/or prediction to be generated.

Objective Modules 840 may comprise a plurality of modules: Raw Labs 842, Heart Failure 844, Infectious Disease 846, and further additional models 848 which may include modules to predict personalized testing results for testing as described herein, or other predictive models. Each module 842, 844, 846, and 848 may be associated with one or more targets 842a, 844a, 846a, and 848a. For example, Raw Labs module 842 may be associated with targets 842a having the objective 'raw results, evaluation thresholds' and time periods 'instant test, tests within 1 week, tests within 1 year.' Heart Failure module 844 may be associated with targets 844a having the objective 'imaging features; diagnostics: stroke, atrial fibrillation, arrhythmia' and time periods 'instant scan, instant test, tests/scans within 1 week, 6, 12, 24, and 60 months.' Infectious Disease module 846 may be associated with targets 846a having the objective 'molecule, pathogen, virus, bacteria, raw sequencing, sequencing thresholds' and time periods 'instant test, tests within 3/6/9/12/24 months.' Additional models 848, such as modules to predict personalized testing results for testing as described herein may be associated with targets 848a having an objective 'raw results, reporting thresholds' and time periods 'instant test, 7, 14, 21, and 28 days; 1/3/6/9/12/24/60 months'. Each module 842, 844, 846, and 848 may be further associated with models 842b, 844b, 846b, and 848b. Models 842b, 844b, 846b, and 848b may be gradient boosting models, random forest models, neural networks (NN), regression models, Naive Bayes models, or machine learning algorithms (MLA). A MLA or a NN may be trained from a training data set such as a plurality of matrices having a feature vector for each subject or images and features. In an exemplary prediction profile, a training data set may include imaging, pathology, clinical, laboratory testing, and/or molecular reports and details of a subject, such as those curated from an EHR or genetic sequencing reports. The training data may be based upon features such as the objective specific sets. MLAs include supervised algorithms (such as algorithms where the features/classifications in the data set are annotated) using linear regression, logistic regression, decision trees, classification and regression trees, Naïve Bayes, nearest neighbor clustering; unsupervised algorithms (such as algorithms where no features/classification in the data set are annotated) using Apriori, means clustering, principal component analysis, random forest, adaptive boosting; and semi-supervised algorithms (such as algorithms where an incomplete number of features/classifications in the data set are annotated) using generative approach (such as a mixture of Gaussian distributions, mixture of multinomial distributions, hidden Markov models), low density separation, graph-based approaches (such as mincut, harmonic function, manifold regularization), heuristic approaches, or support vector machines. NNs include conditional random fields, convolutional neural networks, attention based neural networks, deep learning, long short term memory networks, or other neural models where the training data set includes a plurality of tumor samples, RNA expression data for each sample, and pathology reports covering imaging data for each sample. While MLA and neural networks identify distinct approaches to machine learning, the terms may be used interchangeably herein. Thus, a mention of MLA may include a corresponding NN or a mention of NN may include a corresponding MLA unless explicitly stated otherwise.

Training may include providing optimized datasets as a matrix of feature vectors for each subject, labeling these traits as they occur in subject records as supervisory signals, and training the MLA to predict an objective/target pairing. Artificial NNs are powerful computing models which have shown their strengths in solving hard problems in artificial intelligence. They have also been shown to be universal approximators (can represent a wide variety of functions when given appropriate parameters). Some MLA may identify features of importance and identify a coefficient, or weight, to them. The coefficient may be multiplied with the occurrence frequency of the feature to generate a score, and once the scores of one or more features exceed a threshold, certain classifications may be predicted by the MLA. A coefficient schema may be combined with a rule based schema to generate more complicated predictions, such as predictions based upon multiple features. For example, ten key features may be identified across different classifications. A list of coefficients may exist for the key features, and a rule set may exist for the classification. A rule set may be based upon the number of occurrences of the feature, the scaled weights of the features, or other qualitative and quantitative assessments of features encoded in logic known to those of ordinary skill in the art. In other MLA, features may be organized in a binary tree structure. For example, key features which distinguish between the most classifications may exist as the root of the binary tree and each subsequent branch in the tree until a classification may be awarded based upon reaching a terminal node of the tree. For example, a binary tree may have a root node which tests for a first feature. The occurrence or non-occurrence of this feature must exist (the binary decision), and the logic may traverse the branch which is true for the item being classified. Additional rules may be based upon thresholds, ranges, or other qualitative and quantitative tests. While supervised methods are useful when the training dataset has many known values or annotations, the nature of EMR/EHR documents is that there may not be many annotations provided. When exploring large amounts of unlabeled data, unsupervised methods are useful for binning/bucketing instances in the data set. A single instance of the above models, or two or more such instances in combination, may constitute a model for the purposes of models 842*b*, 844*b*, 846, and 848*b*.

Models may also be duplicated for particular datasets which may be provided independently for each objective module 842, 844, 846, and 848. For example, the Infectious Disease objective module 846 may receive a DNA feature set, an RNA feature set, a combined RNA and DNA feature set, and observational feature set, or a complete dataset comprising all features for each subject. As another example, the Infectious Disease objective module 846 may receive imaging features extracted from various digital images acquired from analysis of a subject's sample, clinical reports, or the instant lab results. A model 846*b* may be generated for each of the potential feature sets or targets 846*a*. Each module 842, 844, 846, and 848 may be further associated with Predictions 842*c*, 844*c*, 846*c*, and 848*c*. A prediction may be a binary representation, such as a "Yes-Target predicted to occur" or "No-Target not predicted to occur." Predictions may be a likelihood representation such as "target predicted to occur with 83% probability/likelihood." Predictions may be a raw adjustment score such as by a value from which the original report may be adjusted or a raw threshold adjustment score such as by a value from which the original threshold may be adjusted. Predictions may be performed on subject data sets having known outcomes to identify insights and trends which are unexpected. For example, a cohort of subjects may be generated for subjects with a common non-diabetic diagnosis who have experienced traditionally higher A1C laboratory results. A prediction model may be associated with an objective for stroke and a target of within 2 years. The model may identify every event in each subject's history and generate a prediction of whether the subject will be stroke free within 2 years of that event. The cohort of subjects may generate, for each event in a subject's medical file, the probability that the subject will remain stroke free within the next two years and compare that prediction with whether the subject actually was stroke free within two years of the event.

For example, a prediction that a subject may be stroke free with a 74% likelihood but in-fact experiences a stroke within two years may inform the prediction model that intervening events before the stroke are worth reviewing or prompt further review of the subject record that lead the prediction to identify characteristics which may further inform a future prediction. An actual occurrence of a target is weighted to 1 and the non-occurrence of the event is weighted to 0, such that an event which is likely to occur but does not may be represented by the difference (0-0.73), an event which is not likely to occur but does may be represented by the difference (0.22-1), to provide a substantial difference in values in comparison to events which are closely predicted (0-0.12 or 1-0.89) having a minimal difference. For determining a prediction, each module 842, 844, 846, and 848 may be associated with a unique set of prior features, forward features, or a combination of prior features and forward features which may be received from feature generation 830.

Prediction store 850 may receive predictions for targets/objectives generated from objective modules 840 and store them for use in the system 800. Predictions may be stored in a structured format for retrieval by a user interface such as, for example, a webform-based interactive user interface which, in some embodiments, may include webforms 860*a-n*. Webforms may support GUIs that can be displayed by a computer to a user of the computer system for performing a plurality of analytical functions, including initiating or viewing the instant predictions from objective modules 840 or initiating or adjusting the cohort of subjects from which the objective modules 840 may perform analytics from. Electronic reports 870*a-n* may be generated and provided to the user via the graphical user interface (GUI) 865. It should be appreciated that the GUI 865 may be presented on a user device which is connected to the content server/prediction engine 800 via a network.

The reports 870 can be provided to the user as part of a network-based subject management system that collects, converts and consolidates subject information from various physicians and health-care providers (including labs) into a standardized format, stores it in network-based storage devices, and generates messages comprising electronic reports once the reports are generated in accordance with embodiments of the present disclosure. In this way, a user (e.g., a physician, oncologist, or any other health care provider, or a subject, receives computer-generated predictions related to a likelihood of a subject's tumor metastasizing, a predicted location of the metastasis, and/or an associated timeline.

In some embodiments, the electronic report may include a recommendation to a physician to treat the subject using a treatment that correlates with a magnitude of a determined degree of risk of the metastasis, a recommendation to a physician to de-escalate when the subject is low risk to reduce adverse events, save cost and improve health response, or a recommendation to a physician to elect a treatment which provides adjustments to the typical monitoring such as scanning, imaging, blood testing. Additionally or alternatively, the electronic report may include a recommendation for accelerated screening of the subject, a recommendation for consideration of additional monitoring. In some embodiments, an electronic report indicating that a subject may experience diabetes, stroke, infectious disease, etc., results in researchers planning a clinical trial by predicting which groups of subjects are most likely to respond to therapy that targets preventions of each respective outcome. In some embodiments, a clinical trial may be performed by selecting subjects who are predicted to be more likely or less likely to test high while not experiencing the associated disease state outcome for one or more laboratory diagnostic tests, using systems and methods in accordance with the present disclosure.

FIG. 9 illustrates the generation of additional derivative feature sets 819 of FIG. 8 and the feature store 820 using alteration modules, including modules for variant characterization above. A feature collection 905 may comprise the modules of feature modules 810, stored alterations 910 from the alteration module 950 and stored classifications 930 from the structural variant classification 980. An alteration module 950 may be one or more microservices, servers, scripts, or other executable algorithms 952a-n which generate alteration features associated with de-identified subject features from the feature collection. Exemplary alterations modules may include one or more of the following alterations as a collection of alteration modules 952a-n. An SNP (single-nucleotide polymorphism) module may identify a substitution of a single nucleotide that occurs at a specific position in the genome, where each variation is present to some appreciable degree within a population (e.g. >1%). For example, at a specific base position, or loci, in the human genome, the C nucleotide may appear in most individuals, but in a minority of individuals, the position is occupied by an A. This means that there is a SNP at this specific position and the two possible nucleotide variations, C or A, are said to be alleles for this position. SNPs underline differences in susceptibility to a wide range of diseases (e.g.—sickle-cell anemia, β-thalassemia and cystic fibrosis result from SNPs).

The severity of illness and the way the body responds to treatments are also manifestations of genetic variations. For example, a single-base mutation in the APOE (apolipoprotein E) gene is associated with a lower risk for Alzheimer's disease. A single-nucleotide variant (SNV) is a variation in a single nucleotide without any limitations of frequency and may arise in somatic cells. A somatic single-nucleotide variation (e.g., caused by cancer) may also be called a single-nucleotide alteration. An MNP (Multiple-nucleotide polymorphisms) module may identify the substitution of consecutive nucleotides at a specific position in the genome. An InDels module may identify an insertion or deletion of bases in the genome of an organism classified among small genetic variations. While usually measuring from 1 to 10,000 base pairs in length, a microindel is defined as an indel that results in a net change of 1 to 50 nucleotides. Indels can be contrasted with a SNP or point mutation. An indel inserts and deletes nucleotides from a sequence, while a point mutation is a form of substitution that replaces one of the nucleotides without changing the overall number in the DNA. Indels, being either insertions, or deletions, can be used as genetic markers in natural populations, especially in phylogenetic studies. Indel frequency tends to be markedly lower than that of single nucleotide polymorphisms (SNP), except near highly repetitive regions, including homopolymers and microsatellites. An MSI (microsatellite instability) module may identify genetic hypermutability (predisposition to mutation) that results from impaired DNA mismatch repair (MMR). The presence of MSI represents phenotypic evidence that MMR is not functioning normally. MMR corrects errors that spontaneously occur during DNA replication, such as single base mismatches or short insertions and deletions. The proteins involved in MMR correct polymerase errors by forming a complex that binds to the mismatched section of DNA, excises the error, and inserts the correct sequence in its place. Cells with abnormally functioning MMR are unable to correct errors that occur during DNA replication and consequently accumulate errors. This causes the creation of novel microsatellite fragments. Polymerase chain reaction-based assays can reveal these novel microsatellites and provide evidence for the presence of MSI. Microsatellites are repeated sequences of DNA. These sequences can be made of repeating units of one to six base pairs in length. Although the length of these microsatellites is highly variable from person to person and contributes to the individual DNA "fingerprint", each individual has microsatellites of a set length. The most common microsatellite in humans is a dinucleotide repeat of the nucleotides C and A, which occurs tens of thousands of times across the genome. Microsatellites are also known as simple sequence repeats (SSRs). A TMB (tumor mutational burden) module may identify a measurement of mutations carried by tumor cells and is a predictive biomarker being studied to evaluate its association with response to Immuno-Oncology (I-O) therapy. Tumor cells with high TMB may have more neoantigens, with an associated increase in cancer-fighting T cells in the tumor microenvironment and periphery. These neoantigens can be recognized by T cells, inciting an anti-tumor response. TMB has emerged more recently as a quantitative marker that can help predict potential responses to immunotherapies across different cancers, including melanoma, lung cancer and bladder cancer. TMB is defined as the total number of mutations per coding area of a tumor genome. Importantly, TMB is consistently reproducible. It provides a quantitative measure that can be used to better inform treatment decisions, such as selection of targeted or immunotherapies or enrollment in clinical trials. A CNV (copy number variation) module may identify deviations from the normal genome and any subsequent implications from analyzing genes, variants, alleles, or sequences of nucleotides. CNV are the phenomenon in which structural variations may occur in sections of nucleotides, or base pairs, which include repetitions, deletions, or inversions.

A Fusions module may identify hybrid genes formed from two previously separate genes. It can occur as a result of: translocation, interstitial deletion, or chromosomal inversion. Gene fusion plays an important role in tumorgenesis. Fusion genes can contribute to tumor formation because fusion genes can produce much more active abnormal protein than non-fusion genes. Often, fusion genes are oncogenes that cause cancer; these include BCR-ABL, TEL-AML1 (ALL with t(12; 21)), AML1-ETO (M2 AML with t(8; 21)), and TMPRSS2-ERG with an interstitial deletion on chromosome 21, often occurring in prostate cancer. In the case of TMPRSS2-ERG, by disrupting androgen receptor (AR) signaling and inhibiting AR expression by oncogenic ETS transcription factor, the fusion product regulates the prostate cancer. Most fusion genes are found from hematological cancers, sarcomas, and prostate cancer. BCAM-AKT2 is a fusion gene that is specific and unique to high-grade serous ovarian cancer. Oncogenic fusion genes may lead to a gene product with a new or different function from the two fusion partners. Alternatively, a proto-oncogene is fused to a strong promoter, and thereby the oncogenic function is set to function by an upregulation caused by the strong promoter of the upstream fusion partner. The latter is common in lymphomas, where oncogenes are juxtaposed to the promoters of the immunoglobulin genes. Oncogenic fusion transcripts may also be caused by trans-splicing or read-through events. Since chromosomal translocations play such a significant role in neoplasia, a specialized database of chromosomal aberrations and gene fusions in cancer has been created. This database is called Mitelman Database of Chromosome Aberrations and Gene Fusions in Cancer. An IHC (Immunohistochemistry) module may identify antigens (proteins) in cells of a tissue section by exploiting the principle of antibodies binding specifically to antigens in biological tissues. IHC staining is widely used in the diagnosis of abnormal cells such as those found in cancerous tumors. Specific molecular markers are characteristic of particular cellular events such as proliferation or cell death (apoptosis). IHC is also widely used in basic research to understand the distribution and localization of biomarkers and differentially expressed proteins in different parts of a biological tissue. Visualizing an antibody-antigen interaction can be accomplished in a number of ways. In the most common instance, an antibody is conjugated to an enzyme, such as peroxidase, that can catalyze a color-producing reaction in immunoperoxidase staining. Alternatively, the antibody can also be tagged to a fluorophore, such as fluorescein or rhodamine in immunofluorescence. Approximations from RNA expression data, H&E slide imaging data, or other data may be generated. For example, in some embodiments, the predictions may include PD-L1 prediction from H&E and/or RNA.

A Therapies module may identify differences in cancer cells (or other cells near them) that help them grow and thrive and drugs that "target" these differences. Treatment with these drugs is called targeted therapy. For example, many targeted drugs go after the cancer cells' inner 'programming' that makes them different from normal, healthy cells, while leaving most healthy cells alone. Targeted drugs may block or turn off chemical signals that tell the cancer cell to grow and divide; change proteins within the cancer cells so the cells die; stop making new blood vessels to feed the cancer cells; trigger your immune system to kill the cancer cells; or carry toxins to the cancer cells to kill them, but not normal cells. Some targeted drugs are more "targeted" than others. Some might target only a single change in cancer cells, while others can affect several different changes. Others boost the way your body fights the cancer cells. This can affect where these drugs work and what side effects they cause.

In some embodiments, matching targeted therapies may include identifying the therapy targets in the subjects and satisfying any other inclusion or exclusion criteria. A VUS (variant of unknown significance) module may identify variants which are called but cannot be classified as pathogenic or benign at the time of calling. VUS may be catalogued from publications regarding a VUS to identify if they may be classified as benign or pathogenic. A Trial module may identify and test hypotheses for treating cancers having specific characteristics by matching features of a subject to clinical trials. These trials have inclusion and exclusion criteria that must be matched to enroll which may be ingested and structured from publications, trial reports, or other documentation. An Amplifications module may identify genes which increase in count disproportionately to other genes. Amplifications may cause a gene having the increased count to go dormant, become overactive, or operate in another unexpected fashion. Amplifications may be detected at a gene level, variant level, RNA transcript or expression level, or even a protein level. Detections may be performed across all the different detection mechanisms or levels and validated against one another. An Isoforms module may identify alternative splicing (AS), the biological process in which more than one mRNA (isoforms) is generated from the transcript of a same gene through different combinations of exons and introns. It is estimated by large-scale genomics studies that 30-60% of mammalian genes are alternatively spliced. The possible patterns of alternative splicing for a gene can be very complicated and the complexity increases rapidly as the number of introns in a gene increases. In silico alternative splicing prediction may find large insertions or deletions within a set of mRNA sharing a large portion of aligned sequences by identifying genomic loci through searches of mRNA sequences against genomic sequences, extracting sequences for genomic loci and extending the sequences at both ends up to 20 kb, searching the genomic sequences (repeat sequences have been masked), extracting splicing pairs (two boundaries of alignment gap with GT-AG consensus or with more than two expressed sequence tags aligned at both ends of the gap), assembling splicing pairs according to their coordinates, determining gene boundaries (splicing pair predictions are generated to this point), generating predicted gene structures by aligning mRNA sequences to genomic templates, and comparing splicing pair predictions and gene structure predictions to find alternative spliced isoforms. A Pathways module may identify defects in DNA repair pathways which enable cancer cells to accumulate genomic alterations that contribute to their aggressive phenotype. Cancerous tumors rely on residual DNA repair capacities to survive the damage induced by genotoxic stress which leads to isolated DNA repair pathways being inactivated in cancer cells. DNA repair pathways are generally thought of as mutually exclusive mechanistic units handling different types of lesions in distinct cell cycle phases. Recent preclinical studies, however, provide strong evidence that multifunctional DNA repair hubs, which are involved in multiple conventional DNA repair pathways, are frequently altered in cancer. Identifying pathways which may be affected may lead to important subject treatment considerations. A Raw Counts module may identify a count of the variants that are detected from the sequencing data. For DNA, this may be the number of reads from sequencing which correspond to a particular variant in a gene. For RNA, this may be the gene expression counts or the transcriptome counts from sequencing.

Structural variant or disease state classification 980 may evaluate features from feature collection 905, alterations from alteration module 950, and other classifications from within itself from one or more classification modules 982a-n. Structural variant classification 980 may provide classifications to stored classifications 930 for storage. An exemplary classification module may include a classification of non-diabetic for a patient with high A1C but similar to other patients classified as nondiabetic, a classification as not myopathic for patients with elevated creatine but similar to asymptomatic patients who are not diagnosed as myopathic, or a classification of a CNV as "Reportable" may mean that the CNV has been identified in one or more reference databases as influencing the tumor cancer characterization, disease state, or pharmacogenomics, "Not Reportable" may mean that the CNV has not been identified as such, and "Conflicting Evidence" may mean that the CNV has both evidence suggesting "Reportable" and "Not Reportable." Furthermore, a classification of therapeutic relevance is similarly ascertained from any reference datasets mention of a therapy which may be impacted by the detection (or non-detection) of the CNV. Other classifications may include applications of machine learning algorithms, neural networks, regression techniques, graphing techniques, inductive reasoning approaches, or other artificial intelligence evaluations within modules 982a-n. A classifier for clinical trials may include evaluation of variants identified from the alteration module 950 which have been identified as significant or reportable, evaluation of all clinical trials available to identify inclusion and exclusion criteria, mapping the subject's variants and other information to the inclusion and exclusion criteria, and classifying clinical trials as applicable to the subject or as not applicable to the subject. Similar classifications may be performed for therapies, loss-of-function, gain-of-function, diagnosis, microsatellite instability, tumor mutational burden, indels, SNP, MNP, fusions, and other alterations which may be classified based upon the results of the alteration modules 952*a-n*.

Each of the feature collection 905, alteration module 950, Structural variant or disease state 980 and feature store 820 may be communicatively coupled to data bus 990 to transfer data between each module for processing and/or storage. In another embodiment, each of the feature collection 905, alteration module 950, Structural variant or disease state 980 and feature store 820 may be communicatively coupled to each other for independent communication without sharing data bus 990.

Features of feature collection and feature store may be utilized herein where any features are received as inputs to a system.

Cohort

Figure 5:
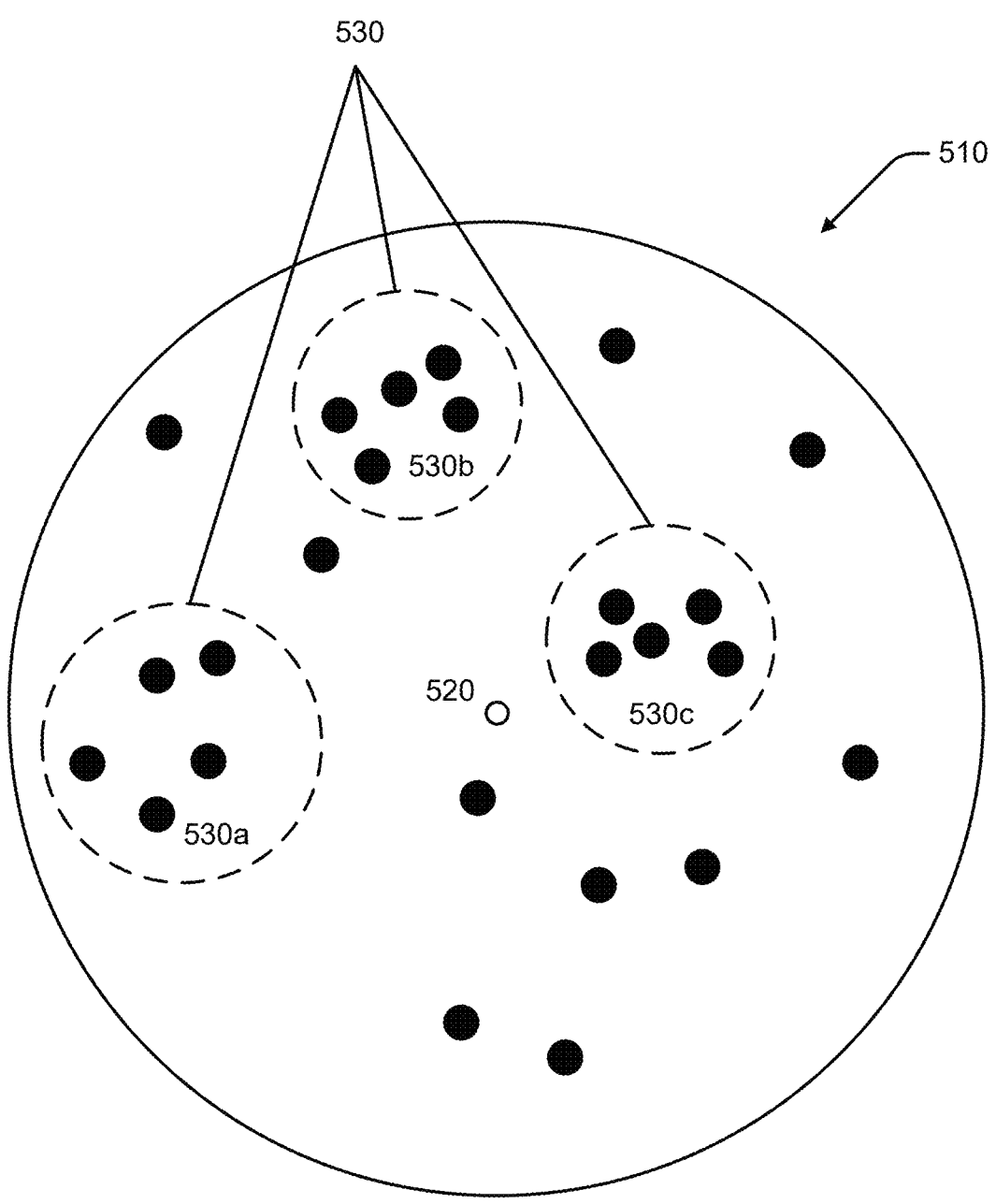
FIG. 5 is an illustration of an interactive cohort software interface, that is consistent with at least some aspects of the present disclosure.

FIG. 5 shows an exemplary interactive cohort software interface with plot 510 for visualizing subject 102 at circle 520 against a cohort of similar subjects. In order to compare a plurality of difference subjects based on one or more analysis module 180 or user defined criteria, the system 101 may reference a subject similarity metric that quantifies a degree to which subjects are similar. Plot 510 represents similarity metrics for each of the similar subjects as solid black dots. subjects (e.g., dots) which appear radially closer to subject 520 are more similar to subject 520 than subjects which appear radially further from subject 520 and subjects which appear closer to other subjects are more similar to the closer subjects than they are to other, further away subjects. Therefore similarities between all subjects to all other subjects of the cohort of similar subjects are visually represented. Subject sub-cohorts 530 may represent clusters of subjects including subjects that are more similar to each other than to other subjects in the larger represented cohort. Sub-cohorts may represent biomarkers amongst the cohort of similar subjects which are shared with the subject 102. A user may select a sub-cohort, such as one of sub-cohorts 530*a-c*, and view the biomarker identified in the sub-cohort, as well as the diagnostic test result considerations associated with that biomarker. In one embodiment, such as an A1C diagnostic test result, a biomarker may include race, such as African descent, and the considerations may include a higher normalized A1C result than the average normal. In another embodiment, such as a creatinine kidney function diagnostic test, a biomarker may include the number of kidneys a subject has, and a consideration of a subject sub-cohort with one kidney may include an increased creatinine level. In yet another embodiment, such as a hemoglobin A1C diagnostic test result, a biomarker may include a detected variant in the G6PD gene and a respective consideration may be presented to the user. In this way, subjects of the cohort of similar subjects to subject 102 may be visually presented along with identification of biomarkers which may influence the personalized, precision-medicine diagnostic results for the subject.

Portal

Embodiments of the systems and methods described herein may be incorporated within a website facing portal accessible via intranet, internet, or any world wide website protocols. Aspects of the portal may include operating as an order management system such as the user's portal to the subject order processing pipeline where a user, such as a physician, researcher, or other subject representatives may initiate an order, request specimen storage and transport units, track order fulfillment, and view results from the laboratory as they are generated. In one embodiment, a subject representative may upload an electronic record, such as a PDF, of laboratory results to generate a report for laboratory results processed by another facility. In one embodiment, the web portal may interface with one or more institution's EMR systems and retrieve results from a subject's records directly.

FIG. 10 details a system 1000 for instantiating an interactive portal according to embodiments herein.

In one example, a portal for oncological disease states may include a system 1000 for predicting and analyzing subject cohort response, progression, and survival may include a back end layer that includes a subject data store 1014 accessible by a subject cohort selector module 1016 in communication with a subject cohort timeline data storage 1018. The subject cohort selector module 1016 interacts with a front end layer that includes an interactive analysis portal 1022 that may be implemented, in one instance, via a web browser to allow for on-demand filtering and analysis of the data store 1014.

The interactive analysis portal 1022 may include a plurality of user interfaces including an interactive cohort selection filtering interface 1024 that, as discussed in greater detail below, permits a user to query and filter elements of the data store 1014. As discussed in greater detail below, the portal 1022 also may include a cohort funnel and population analysis interface 1026, a subject timeline analysis user interface 1028, a subject survival analysis user interface 1030, and a subject event likelihood analysis user interface 1032. The portal 1022 further may include a subject next analysis user interface 1034 and one or more subject future analysis user interfaces 36.

Returning to FIG. 10, the back end layer also may include a distributed computing and modeling layer 1038 that receives data from the subject cohort timeline data storage 1018 to provide inputs to a plurality of modules, including, a time to event modeling module 1040 that powers the subject survival analysis user interface 1030, an event likelihood module 1042 that calculates the likelihood of one or more events received at the subject event likelihood analysis user interface 1032 for subsequent display in that user interface, a next event modeling module 1044 that generates models of one or more next events for subsequent display at the subject next event analysis user interface 1034, and one or more future modeling modules 1046 that generate one or more future models for subsequent display at the one or more subject future analysis user interfaces 1036.

The subject data store 1014 may be a pre-existing dataset that includes subject clinical history, such as demographics, comorbidities, diagnoses and recurrences, medications, surgeries, and other treatments along with their response and adverse effects details. The subject Data Store may also include subject genetic/molecular sequencing and genetic mutation details relating to the subject, as well as organoid modeling results. In one aspect, these datasets may be generated from one or more sources. For example, institutions implementing the system may be able to draw from all of their records; for example, all records from all doctors and/or subjects connected with the institution may be available to the institutions agents, physicians, research, or other authorized members. Similarly, doctors may be able to draw from all of their records; for example, records for all of their subjects. Alternatively, certain system users may be able to buy or license aspect to the datasets, such as when those users do not have immediate access to a sufficiently robust dataset, when those users are looking for even more records, and/or when those users are looking for specific data types, such as data reflecting subjects having certain primary cancers, metastases by origin site and/or diagnosis site, recurrences by origin, metastases, or diagnosis sites, etc.

A subject data store may include one or more feature modules which may comprise a collection of features available for every subject in the system 1000. These features may be used to generate and model the artificial intelligence classifiers in the system 1000. These features may include the features as described above with respect to the order processing pipeline. Including, the plurality of features present in the feature modules comprising features available within subject health records 814, including information contained in the source subject, structured subject, structured clinomic data repository, and laboratory datasets, above, to include comprehensive collection of subject data.

The system may include a data delivery pipeline to transmit clinical and molecular de-identified records in bulk. The system also may include separate storage for de-identified and identified data to maintain data privacy and compliance with applicable laws or guidelines, such as the Health Insurance Portability and Accountability Act.

The raw input data and/or any transformed, normalized, deconvoluted, and/or predictive data may be stored in one or more relational databases for further access by the system in order to carry out one or more comparative or analytical functions, as described in greater detail herein. The data model used to construct the relational database(s) may be used to store, organize, display, and/or interpret a significant amount and variety of data, e.g., dozens of tables that comprise hundreds of different columns. Unlike standard data models such as OMOP or QDM, the data model may generate unique linkages within a table or across tables to directly relate various clinical attributes, thereby making complex clinical attributes easier to ingest, interpret and analyze.

Once the relevant data has been received, transformed, and manipulated, as discussed above, the system may include a plurality of modules in order to generate the desired dynamic user interfaces, as discussed above with regard to the system diagram of FIG. 10.

In various embodiments, one or more statistical models and analyses may be combined to accommodate a particular purpose and, through a variation of the initial analysis, may be used to solve a number of problems. Such a combination of statistical models and analyses may be stored as a notebook in the Interactive Analysis Portal 1022. Notebook is a feature in the Interactive Analysis Portal 1022 which provides an easily accessible framework for building statistical models and analyses. Once the statistical models and analyses have been developed, they may then be shared with different users to analyze and find answers to scientific and business questions other than those for which they were initially developed.

1) The Interactive Analysis Portal 1022 allows input customization through a simple, intuitive point-and-click/drag-and-drop interface to narrow down the cohort for analysis. Cohorts which have been selected, either through the Interactive Analysis Portal 1022, Outliers, Smart Cohorts, or other portals of the Interactive Analysis Portal 1022, may be provided to a notebook for processing.

2) A custom application interface (API) having a library of function calls which interface with the Interactive Analysis Portal 1022, underlying authorized databases, and any supported statistical models, visualizations, arithmetic models, and other provided operations may be provided to the user to integrate a notebook or workbook with the Interactive Analysis Portal 1022 data, function calls, and other resources. Exemplary function calls may include listing authorized sources of data, selecting a datasource, filtering the datasource, listing clinical events of the subjects in the current filtered cohort, identification of fusions from RNA or DNA, identification of genes from RNA or DNA, identifying matching clinical trials, DNA variants, identifying immunohistochemistry (IHC), identifying RNA expressions, identifying therapies in the cohort, identifying potential therapies that are applicable to treat subjects in the cohort, and other cohort or dataset processing.

3) The Interactive Analysis Portal 1022 allows the Notebook generation to perform one or more statistical models, analysis, and visualization or reporting of results to the narrowed down cohort without having the user code anything in the notebook as the selected models, analysis, visualizations, or reports of the notebook itself are configured to accept the cohort from the Interactive Analysis Portal 1022 and provide the analysis on the cohort as is, without user intervention at the code level. Some models may have hyperparameters or tuning parameters which may be selected, or the models themselves may identify the optimal parameters to be applied based on the cohort and/or other models, analysis, visualizations, or reports during run-time.

4) The Interactive Analysis Portal 1022 displays the prepared results to the user based on the selected notebook.

5) An associated user may then select a previously generated notebook which applies selected analysis to the narrowed down cohort without having the user code or recode anything in the notebook as the notebook itself is configured to accept the cohort from the Interactive Analysis Portal 1022 and provide the notebook results without user intervention.

6) Users may track the computation resources used by their notebooks for understanding the costs for cloud computing or hardware resources over the network and may track the popularity of their notebook to judge the effectiveness of the statistical analysis that they provide through the notebook.

In certain embodiments, notebooks provide a benefit to users by allowing the Interactive Analysis Portal 1022 to provide custom templates to their selected data and leverage pre-built healthcare statistical models to provide results to users who are not sophisticated in programming. Internal teams may analyze curated data in order to support new healthcare insights that both help improve subject care and improve life science research. Similarly, external users have easy access to this proprietary real-world data for analysis and access to proprietary statistical models.

A billing model for a user may be provided on a subscription basis or an on-demand basis. For example, a user may subscribe to one or more data sets for a period of time, such as a monthly or yearly subscription, or the user may pay on a per-access basis for data and notebook usage, such as for loading a specific cohort with corresponding notebook and paying a fee to generate the instant results for consumption. Users may desire a benchmarking and optimization portal through which they may view and optimize their storage and computing resources uses.

Generating a notebook may be performed with a GUI for notebook editing. A user may configure a reporting page for a notebook. A reporting page may include text, images, and graphs as selected and populated by the users. Preconfigured elements may be selected from a list, such as a dropdown list or a drag-and-drop menu. Preconfigured elements include statistical analysis modules and machine learning models. For example, a user may wish to perform linear regression on the data with respect to specific features. A user may select linear regression, and a menu with checkboxes may appear with features from their data set which should be supplied to the linear regression model. Once filled out, a template for reporting the linear regression results with respect to the selected features may be added to the reporting page at a location identified by the active cursor or the drop location for a drag-and drop-element. If a user wishes to solve a problem using a machine learning model, it may be added to the sheet. A header may be populated identifying the model, the hypertuning parameters, and the reported results. In some instances, a model that was previously trained may then be applied to the current cohort. In other instances, the model may be trained on the fly, for example by selecting annotated features and associated outcomes for which the model should be trained. In an unsupervised machine learning model, the model may not require selection of annotated features as the features will be identified during training. In some embodiments, if a selected statistical model requires results from a trained model which are not computed in the template, the template may automatically add the trained model to generate the required results prior to inserting the selected statistical model to the notebook.

Statistical analysis models may be predesigned for calculating the arithmetic mean of the cohort with respect to a selected feature, the standard deviation/distribution of the cohort for a selected feature, regression relationships between variables for selected features, sample size determining models for subsetting the cohort into the optimal sub-population for analysis, or t-testing modules for identifying statistically significant features and correlations in the cohort. Other precomputed statistical analysis modules may perform cohort analysis to identify significant correlations and/or features in the cohort, data mining to identify meaningful patterns, or data dredging to match statistical models to the data and report out which models may be applicable and add those models to the notebook.

Machine learning models may apply linear regression algorithms, non-linear regression, logistic regression algorithms, classification models, bootstrap resampling models, subset selection models, dimensionality reduction models, tree-based models (such as bagging, boosting, and random forest), and other supervised or unsupervised models. As each model is selected, a target output may be requested from the user specifying which feature(s) the model should identify, classify, and/or report. For example, a user may select for the model to identify which features most closely correlate to subject survival in the cohort, or which features most closely correlate with a positive treatment outcome in the cohort. The user may also select which classification labels from the classification labels of the model that they wish the model to classify. In an example where the model may classify the cohort according to five labels, the user may specify one or more labels as a binary classification (subject has label, subject does not have label) such as whether a subject with a tumor of unknown origin originated from the breast, lung, or brain. The user may select only breast to identify for any tumors of unknown origin whether the tumor may be classified as coming from the breast or not from the breast.

Systems and methods for instantiating an online web portal in accordance with the above description including additional functionality may be found in U.S. patent application Ser. No. 16/732,168, titled "A Method And Process For Predicting And Analyzing Patient Cohort Response, Progression And Survival" and filed Dec. 31, 2019, incorporated by reference herein in its entirety for all purposes.

The website portal may provide reports to the subject's representatives containing both the testing results for the disease state and additional contextual information surrounding the disease state, its diagnosis, prognosis, treatments, outcomes, predictions, available trials and therapies, and other relevant information identified herein.

Oncology Reports

An exemplary report for a subject undergoing sequencing for a disease state of cancer may include:

A summary of molecular results to highlight somatic and germline genes which influence diagnosis and treatment or are otherwise clinically actionable
A summary of pharmacogenomic results to highlight genes which impact the efficacy of medications
A summary of drug administration, dosing, risks, and contraindications to consider
A summary of available clinical trials and therapies matching the subject's genomic constitution
A cohort summary of potential therapies and their outcome for subjects of similar genetic constitution Mental Health Reports An exemplary report for a subject undergoing sequencing for a disease state of depression may include:

A summary of molecular results to highlight genes which influence diagnosis and treatment
A summary of pharmacogenomic results to highlight genes which impact the efficacy of medications
A summary of drug administration, dosing, risks, and contraindications to consider
A summary of pharmacogenomic effect on medications classified as antidepressants, anticonvulsants, anxiolytics, mood stabilizers, antimanics, hypnotics, VMAT2 inhibitors, ADHD, and other medications
A summary of additional molecular results for consideration in potential disease state risks
A polygenic risk assessment to compare the subject's risk to that of others based on genetic constitution
A cohort summary of potential therapies and their outcome for subjects of similar genetic constitution Lab Test Reports A summary of lab test results to highlight subject's current disease state and any extenuating or mitigating factors that may adjust the threshold of interpretation for each lab test
A summary of the expected extenuation or mitigation provided from clinical information for each factor EKG Reports A summary of electrocardiogram results to highlight predictive expected outcomes from a number of leads
A summary of predictions and the clinical information they are derived from View Cohort

---

A summary of analytic results for a selected cohort of patients
Customizable analytics and graphs

---

Custom Data Orders

---

A summary of analytic results for a selected cohort of patients
A download of the raw data ordered
Customizable analytics and graphs
Cohort analysis tools to identify special genomic constitutions
having unexpected outcomes which may be researched further

---

Mobile App

Mobile devices, such as cellular phones, laptop computers, tablets, and other mobile devices may install an application from the laboratory to implement methods and systems as described herein. A physician may utilize the application to begin an order, request specimen storage and mailing units, print mailing labels, track a subject's progress through the order processing pipeline, and review the reports order upon order fulfillment. Lab personnel may utilize the application to track an order that has been received, periodically update the order status based upon fulfillment of certain conditions during order processing, and sign off on a completed report for release to ordering physician. The application may automatically supply notification to other lab personnel or the ordering physician of those condition fulfillments. Research participants may track a plurality of subjects who have registered with the research during execution of a clinical trial, including order fulfillment of laboratory results.

In one embodiment, a physician may see each of the subject for whom they have ordered laboratory results in the app. Selection of a subject from the listing of available subjects will display to the physician the current order status for their laboratory results as well as a reporting of the results upon completion. The physician may add new subjects to the system and place a new order or upload laboratory results in the form of an image or file to see report results adjusted based upon the subject's clinical history, genomic constitution, and other factors.

An exemplary application may interface with an EMR system storing patient's clinical information or to a third party collection of clinical information to facilitate record review and testing results optimization.

Methods and systems for implementing a mobile application and related functionality may be found in U.S. patent application Ser. No. 16/289,027, titled "Mobile Supplementation, Extraction, And Analysis Of Health Records" and filed Feb. 28, 2019, incorporated by reference herein for all purposes.

Hardware/Cloud Platform

Figure 6:
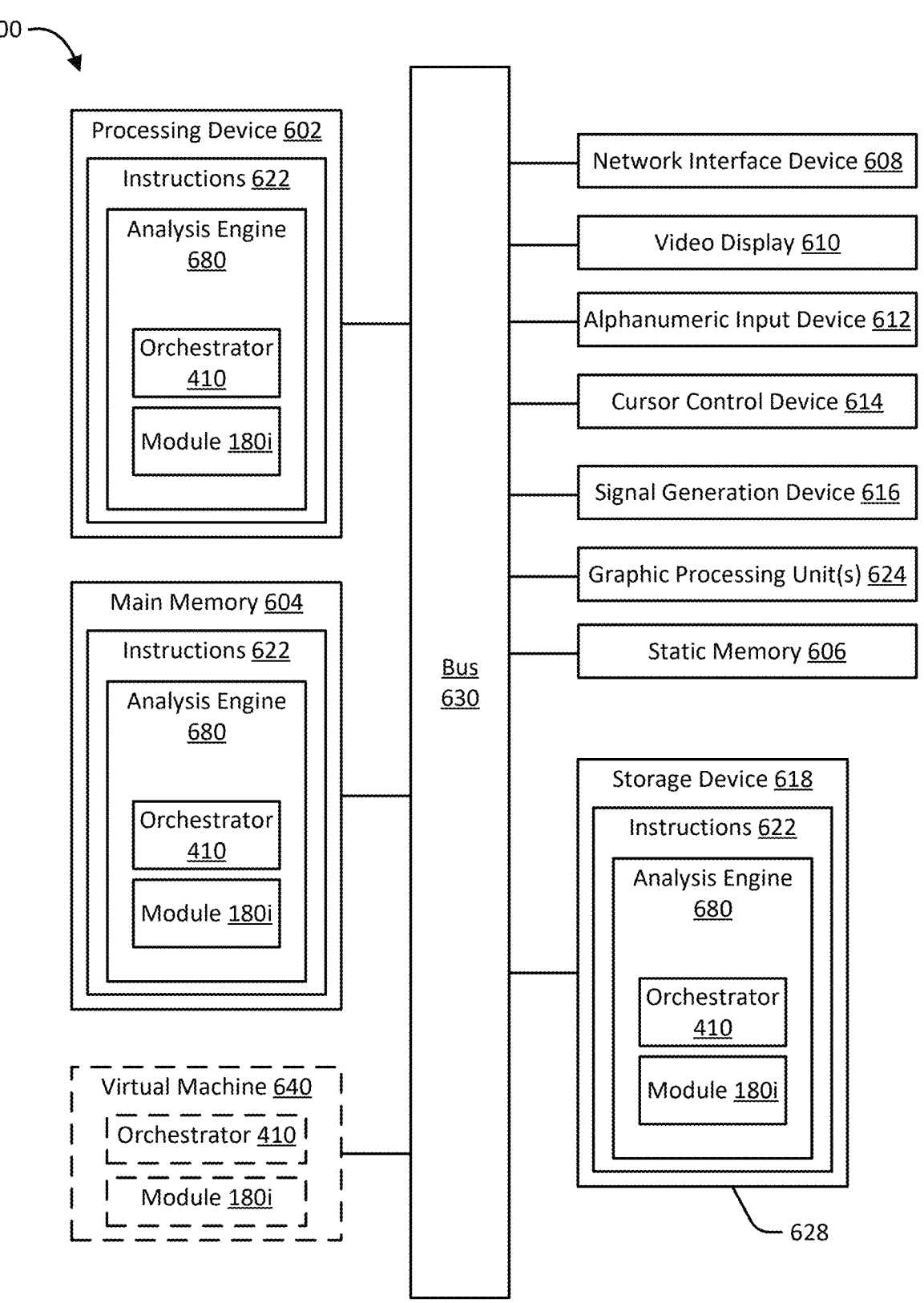
FIG. 6 is an illustration of a computer system that includes components that are consistent with at least some aspects of the present disclosure which performs various processes and methods as described hereafter.

FIG. 6 is an illustration of an example machine or a computer system 600 within which a set of instructions, for causing the machine to perform any one or more of the methodologies discussed herein, may be executed. In alternative implementations, the machine may be connected (such as networked) to other machines in a LAN, an intranet, an extranet, and/or the Internet.

The machine may operate in the capacity of a server or a client machine in client-server network environment, as a peer machine in a peer-to-peer (or distributed) network environment, or as a server or a client machine in a cloud computing infrastructure or environment. The machine may be a personal computer (PC), a tablet PC, a set-top box (STB), a Personal Digital Assistant (PDA), a cellular telephone, a web appliance, a server, a network router, a switch or bridge, or any machine capable of executing a set of instructions (sequential or otherwise) that specify actions to be taken by that machine. Further, while a single machine is illustrated, the term "machine" shall also be taken to include any collection of machines that individually or jointly execute a set (or multiple sets) of instructions to perform any one or more of the methodologies discussed herein.

The example computer system 600 includes a processing device 602, a main memory 604 (such as read-only memory (ROM), flash memory, dynamic random access memory (DRAM) such as synchronous DRAM (SDRAM) or DRAM, etc.), a static memory 606 (such as flash memory, static random access memory (SRAM), etc.), and a data storage device 618, which communicate with each other via a bus 630.

Processing device 602 represents one or more general-purpose processing devices such as a microprocessor, a central processing unit, or the like. More particularly, the processing device may be complex instruction set computing (CISC) microprocessor, reduced instruction set computing (RISC) microprocessor, very long instruction word (VLIW) microprocessor, or processor implementing other instruction sets, or processors implementing a combination of instruction sets. Processing device 602 may also be one or more special-purpose processing devices such as an application specific integrated circuit (ASIC), a field programmable gate array (FPGA), a digital signal processor (DSP), network processor, or the like. The processing device 602 is configured to execute instructions 622 for performing the operations and steps discussed herein.

The computer system 600 may further include a network interface device 608 for connecting to the LAN, intranet, internet, and/or the extranet. The computer system 600 also may include a video display unit 610 (such as a liquid crystal display (LCD) or a cathode ray tube (CRT)), an alphanumeric input device 612 (such as a keyboard), a cursor control device 614 (such as a mouse), a signal generation device 616 (such as a speaker), and a graphic processing unit 624 (such as a graphics card).

The data storage device 618 may be a machine-readable storage medium 628 (also known as a computer-readable storage medium) on which is stored one or more sets of instructions or software 622 embodying any one or more of the methodologies or functions described herein. The instructions 622 may also reside, completely or at least partially, within the main memory 604 and/or within the processing device 602 during execution thereof by the computer system 600, the main memory 604 and the processing device 602 also constituting machine-readable storage media.

In one implementation, the instructions 622 include instructions for an Analysis Engine 680 and/or a software library containing methods that function as an Analysis Engine 680. The instructions 622 may further include instructions for an orchestrator 410 and specialized testing stage for Module 180i, such as the orchestrator 410 and Module 180i of FIG. 2. While the machine-readable storage medium 628 is shown in an example implementation to be a single medium, the term "machine-readable storage medium" should be taken to include a single medium or multiple media (such as a centralized or distributed database, and/or associated caches and servers) that store the one or more sets of instructions. The term "machine-readable storage medium" shall also be taken to include any medium that is capable of storing or encoding a set of instructions for execution by the machine and that cause the machine to perform any one or more of the methodologies of the present disclosure. The term "machine-readable storage medium" shall accordingly be taken to include, but not be limited to, solid-state memories, optical media and magnetic media. The term "machine-readable storage medium" shall accordingly exclude transitory storage mediums such as signals unless otherwise specified by identifying the machine readable storage medium as a transitory storage medium or transitory machine-readable storage medium.

In another implementation, a virtual machine 640 may include a module for executing instructions for an orchestrator 410 and specialized testing stage for Module 180i, such as the orchestrator 410 and Module 180i of FIG. 2. In computing, a virtual machine (VM) is an emulation of a computer system. Virtual machines are based on computer architectures and provide functionality of a physical computer. Their implementations may involve specialized hardware, software, or a combination of hardware and software.

Some portions of the preceding detailed descriptions have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities. Usually, though not necessarily, these quantities take the form of electrical or magnetic signals capable of being stored, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as "identifying" or "providing" or "calculating" or "determining" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage devices.

The present disclosure also relates to an apparatus for performing the operations herein. This apparatus may be specially constructed for the intended purposes, or it may comprise a general purpose computer selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMS, EEPROMs, magnetic or optical cards, or any type of media suitable for storing electronic instructions, each coupled to a computer system bus.

The algorithms and displays presented herein are not inherently related to any particular computer or other apparatus. Various general purpose systems may be used with programs in accordance with the teachings herein, or it may prove convenient to construct a more specialized apparatus to perform the method. The structure for a variety of these systems will appear as set forth in the description below. In addition, the present disclosure is not described with reference to any particular programming language. It will be appreciated that a variety of programming languages may be used to implement the teachings of the disclosure as described herein.

The present disclosure may be provided as a computer program product, or software, that may include a machine-readable medium having stored thereon instructions, which may be used to program a computer system (or other electronic devices) to perform a process according to the present disclosure. A machine-readable medium includes any mechanism for storing information in a form readable by a machine (such as a computer). For example, a machine-readable (such as computer-readable) medium includes a machine (such as a computer) readable storage medium such as a read only memory ("ROM"), random access memory ("RAM"), magnetic disk storage media, optical storage media, flash memory devices, etc.

EXAMPLES

Example 1—Hemoglobin A1C

Figure 3A:
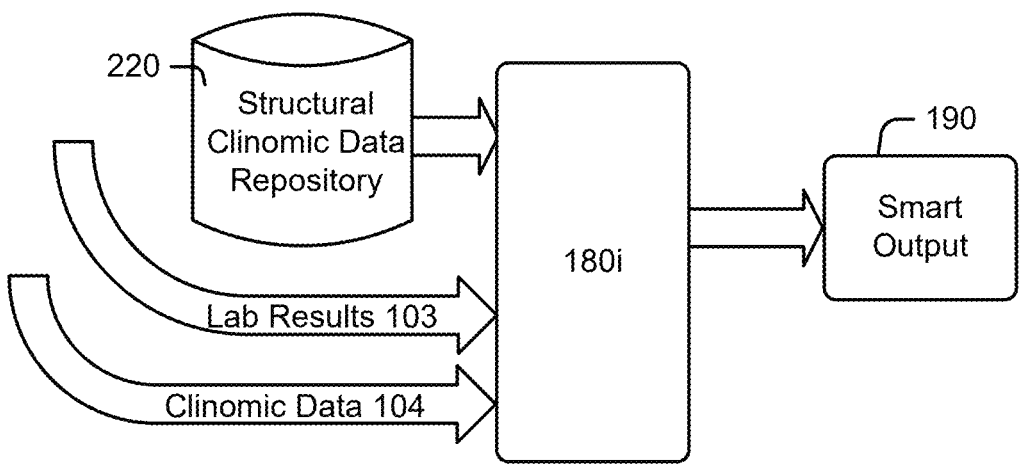
FIG. 3A is an illustration of an analysis module for a subject who has had a diagnostic laboratory test for Hemoglobin A1C, that is consistent with at least some aspects of the present disclosure.
Figure 3B:
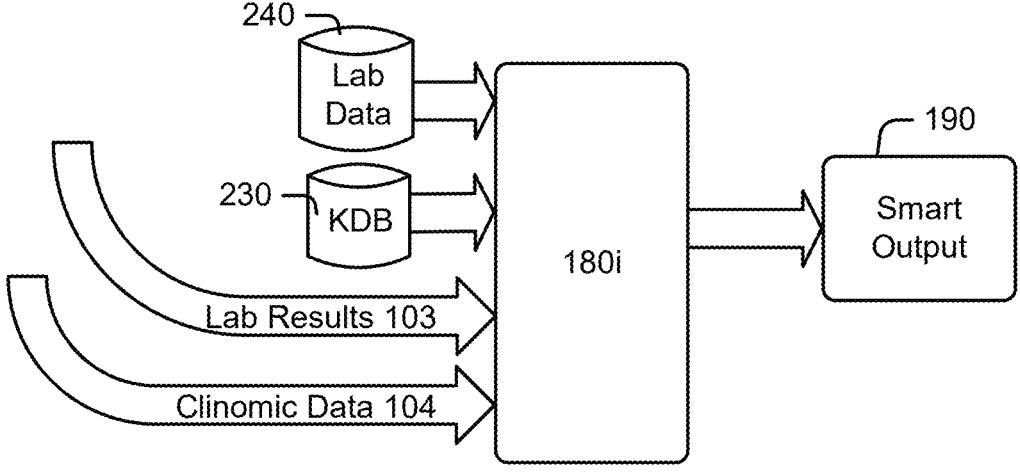
FIG. 3B is an illustration of an analysis module for a subject who has had a diagnostic laboratory test for Hemoglobin A1C and genomic sequencing, that is consistent with at least some aspects of the present disclosure.

FIGS. 3A and 3B illustrate applications of analysis modules 180a-n within analysis library 180 according to an example. Referring also and again to FIG. 1, FIG. 3A illustrates an embodiment of an analysis module 180i for subject 102 who has had a diagnostic laboratory test for Hemoglobin A1C performed at a laboratory other than laboratory 140. For subject 102, data repository 160 may include subject associated records and/or other subject records in the structural clinomic data repository 220, a lab result 103, and provider supplied clinomic data 104. Analysis module 180i may receive available subject data from clinomic data 104 and/or structural clinomic data repository 220. Analysis module 180i may identify key subject features which trigger additional scrutiny and personalized testing result adjustments. Such features may include aspects of the subject's clinomic profile as described above. For an A1C diagnostic test, key subject features may include identification of a history of kidney failure, liver disease, severe anemia, sickle cell anemia, or thalassemia, identification that the subject 102 is of African, Mediterranean, or Southeast Asian descent, or identification that the subject 102 has recently received a blood transfusion or is pregnant. Additional subject clinomic profile features which affect A1C results may include age, sex, systolic blood pressure, diastolic blood pressure, body mass index, fasting glucose, glucose AUC, corrected insulin response, and insulin resistance. Key subject features may be identified in advance based upon AI data mining, machine learning, heuristic analysis of relevant publications trolled from the internet or stored within a knowledge database 230 or calculated on-the-fly, in real time based upon analysis of a cohort of similar subjects who have features in common with the subject 102 by comparing the cohort diagnostics results and diagnosis against those of the normal expected ranges. In one example, analysis module 180i may request prior subject records for subject 102 to review subject history and train an A1C personalization model on the best precision medicine interpretation of the subject results. For example, if subject 102 always returns a higher A1C with no other indications of diabetes, the model may generate a coefficient factor which compensates for the subject's natural propensity towards a higher A1C diagnostic testing result or may similarly increase the thresholds with which a physician should compare the diagnostic testing results. In another example, analysis module 180*i* may request a number of similar subjects based upon the subject's clinomic profile to form a cohort of similar subjects from which diagnosis and treatment comparisons may be performed. Comparisons between the diagnostics results, diagnosis, treatments, and treatment outcomes may be provided in a report to the subject's physician or visually displayed in a radial plot with informative callouts which allow the physician to explore analytics associated with the cohort in real time via an online portal. In yet another example, analysis module 180*i* may request diagnostic results from subjects who also received diagnostic test results from the same laboratory and, if available, results for the same diagnostic tests from other laboratories to identify any bias that may be introduced from that laboratory's specific processing of subject specimens. For example, a laboratory's specific testing procedures may naturally deliver results which are naturally higher than the results of another laboratory. In this manner, analysis module 180*i* may deliver one or more smart outputs to smart output 190. For example, a normal range of A1C level may be between 4% and 5.6% with higher levels suggesting a likelihood of being diabetic and levels exceeding 6.5% suggesting an active diagnosis of diabetes. A subject's ethnicity may inform A1C measurements such that mean A1C levels may actually hover around 5.78% for Caucasians, 5.93% for Hispanics, 6.00% for Asians, 6.12% for American Indians, and 6.18% for Africans. Therefore, analysis module 180*i* may apply a correction factor to generate a smart output which accounts for racial differences in A1C levels as diagnostic testing is performed on a subject.

FIG. 3B illustrates an embodiment of an analysis module 180*i* for a subject 102 who has had a diagnostic laboratory test for Hemoglobin A1C performed at laboratory 140. Referring also and again to FIG. 1, for subject 102, data repository 160 may include information relating to genomic profiling of subjects based upon the type of specimen review which may be performed at a lab, a lab result 103, a knowledge database 220 may include information relating to the interaction between laboratory test results and the human medical condition based on clinomic and genomic analysis, and provider supplied clinomic data 104.

Analysis module 180*i* may receive available subject data from clinomic data 104 if any exists. Analysis module 180*i* may identify key subject features which trigger additional scrutiny and personalized testing result adjustments. Such features may include aspects of the subject's clinomic profile as described above, however, for tests performed at laboratory 140, additional genomic considerations may be evaluated based upon next-generation sequencing results additionally processed from the subject's specimen 115. For example, in an instance where analysis module 180*i* is generating an A1C diagnostic test result smart output, lab data 240 may include identification of genomic variants which have been called during a sequencing of the subject's genome.

Genetic variants which may inform a precision medicine adjustment for subject 102 include variants, variations insertions, deletions, polymorphisms, copy number alterations, or fusions in the CDKAL1, CDKN2A/B, IGF2BP2, TCF7L2, HHEX, FADS1, or G6PD genes. A compilation of the normal human genome for these and other genes may be stored in KDB 220 and methods and procedures for identifying variants, variations insertions, deletions, polymorphisms, copy number alterations, or fusions from sequencing results may be included in laboratory database 240.

Analysis module 180*i* may also request subject sequencing and diagnostic results from laboratory database 240 to train a model to identify new biomarkers which may impact a subject's A1C diagnostic results and calculate a respective smart output from the new biomarker. In such instances, the new biomarker may be referenced in databases 220, 240, or flagged for review by a variant scientist for clearance and publication. Smart outputs may include adjustments to raw diagnostic testing results, evaluation thresholds, cohort reports or real time monitoring through a software interface, or other such smart outputs which present a personalized diagnostic result for subject 102.

Referring back to the prior example, if the subject's raw A1C is 6% and the result adjustment engine increases the raw result of the A1C test by 0.81%, then the system may identify metformin as a therapy for the doctor to consider in making a therapy recommendation the subject. In another instance, referring back to the prior example, if the result adjustment engine increases the raw result of the A1C test by 0.81%, then the system may identify the subject's age, gender, race, and G6PD variant as the factors responsible for the increase. The system may also identify that the raw result of the A1C test was increased by 0.81%.

Example 2—Creatinine

Additional embodiments, not shown, may be processed at analytic module 180*i* for a subject 102. For example, analysis module 180*i* may review the subject's treatment history and observe a nephrectomy (e.g., surgical procedure to remove the kidney) was previously performed on the subject which may impact diagnostic testing results. For example, normal levels of creatinine in the blood may be approximately 0.6 to 1.2 milligrams (mg) per deciliter (dL) in adult males and 0.5 to 1.1 milligrams per deciliter in adult females. However, a person with only one kidney or only one normally-functioning kidney may have an increased normal level of approximately 1.8 or 1.9 mg/dL. Analysis module 180*i* may identify the increased normal levels through AI modeling after processing subject results or may reference previously identified or known deviations from normal from a KDB and provide a smart output with compensated results.

Example 3—Stroke Prediction

In another example, laboratory diagnostic testing may be an imaging scan such as an x-ray, CT, MRI, or other imaging scan. When the laboratory diagnostic testing is to identify subjects at risk of a stroke from an MRI scan, the diagnostic results may be the image(s) from the MRI. Brain infarcts (BI) detected on MRI are commonly seen in older persons, being described in 8%-28% of participants in population-based cohort studies. Most MRI-defined BI are covert, not being associated with overt, clinical stroke symptoms. Nonetheless, they cannot be considered silent or benign, as they are often associated with subtle neurologic symptoms and with increased risk of future stroke, cognitive decline, and in some studies dementia. Analysis module 180*i* may request subject genomic data as well as the MRI results. A subject with a LINC00539 or ZDHHC20 genomic variation may, despite a diagnostic testing result of a benign BI, be at risk for a subsequent brain clot which may result in a stroke. Analysis engine may present an additional warning alongside the diagnostic testing results that subjects having LINC00539 or ZDHHC20 genomic variations, such as detected in subject 102, are none-the-less at a higher risk for stroke even when given a clean bill of health from the MRI scan showing only a benign BI. In this manner, a smart output may be generated not only for laboratory diagnostic tests of human fluids, solids, and cells, but also imaging diagnostic tests.

Example 4—Infectious Disease Testing

In this example, one or more assays (for example, PCR-based, isothermal nucleic acid amplification-based, NGS-based, serology-based, array/microarray/array card/openarray plate/FilmArray/etc., ELISA, ELISpot, FluoroSpot, antigen-based, rapid antigen testing, or other molecular assay) are applied to a patient specimen (patient specimens may include saliva, blood, nasal/anterior nares swab, nasopharyngeal swab, nylon flocked swabs, spun polyester swabs, nasopharyngeal aspirate, bronchoalveolar lavage, specimens collected in Mawls tubes or Longhorn Primerstore MTM tubes, nasopharyngeal/nasal/nares or other specimens collected in viral transport medium/VTM, fecal, etc.) or a molecule isolated from a patient specimen (for example, RNA, DNA, total nucleic acids, cell-free DNA, cell-free RNA, diluted or undiluted) and a pathogen or pathogen-related molecule, biomarker, or signature is detected in the patient specimen. In various examples, saliva may be collected in a Spectrum DNA Saliva Collection Device SDNA-1000. The pathogen (for example, the genome of the pathogen, proteins generated by the pathogen, etc.) and/or the host's response to the pathogen (for example, an immune profile, an RNA expression pattern or signature, etc.) may be detected. Each assay may be capable of detecting multiple indicators of a pathogen. For example, a PCR-based assay may detect more than one segment of a pathogen's genome. Pathogens may include infectious agents that cause disease, viruses, bacteria, fungi, etc. In various embodiments, the patient may be any age at the time that the specimen is collected.

In various embodiments, the assay includes controls (for example, no template control/NTC, a known healthy/negative control, MS2 control, RNAse P, Xeno, other internal positive controls, controls that may be used to confirm that a PCR amplification was successful, *Bacillus* atropheus, Zeptometrix RPP 1, controls that may be used to confirm that a nucleic acid extraction/isolation step was successful, controls that may be used to confirm that a cell lysis step was successful, controls that may be used to confirm that a nucleic acid detection step was successful, etc.) and may have a limit of detection. In various embodiments, the assay includes a quantitative internal reference (for example, a standard ladder having multiple control samples, each having a known concentration of detectable molecules associated with one or more pathogens).

In various embodiments, the assay may be validated for negative/positive predictive values (NPV or PPV), accuracy, precision, and/or specificity for at least one pathogen. In various embodiments, the assay may be compared to a second assay and the positive percent agreement (PPA), negative percentage agreement (NPA) and/or overall percentage agreement (OPA) may be calculated for at least one pathogen. In various embodiments, the assay may be interference tested, for example, to determine which substances or processes could cause false results.

In one embodiment, the patient specimens are remnants of flocked nasopharyngeal swab specimens stored in viral transport medium (VTM). 200 µl of a patient specimen is combined with 10 µl of $5 \times 10^{10}$ PFU/ml MS2 bacteriophage and nucleic acids (for example, DNA, RNA, total nucleic acids (TNA)) are extracted from the combination, using a commercially available kit (for example, bioMérieux easy-MAG extractor, Beckman RNAdvance viral extraction kit using a Biomek i7 device, or another nucleic acid extraction kit, etc.). The final isolated TNA from a specimen is contained in a volume of elution buffer (for example, 110 µl).

In this embodiment, the PCR-based assay is a kit including a sealed 96-well plate, wherein each well may contain lyophilized reagents used for the assay reaction. Nucleic acid extracts (which may be contained in a volume of elution buffer, for example, 35 µl) from either specimen or controls (for example, extracted by a commercially available extraction kit or included in the assay kit) may be added directly to a well, for example, by piercing through the seal and resealing the wells after adding nucleic acid. One positive and one negative control sample may be included in each plate.

After resealing the wells, nucleic acids may be amplified. In one example, amplification includes multiplexed reverse transcription (RT)-PCR and bead hybridization. In various embodiments, this step takes approximately 2 hours. After amplification, data are collected from the plate. In one example, data collection includes measuring median fluorescence intensity (MFI) for each well (for example, using a MAGPIX instrument), for each indicator within the well (for example, each pathogen that can be detected by the assay may have a separate indicator within the well). In various embodiments, this step takes approximately 1 hour. For each class of pathogen, the MFI associated with a pathogen class in a control well (or an average of the MFI's associated with the pathogen class in multiple control wells) may be subtracted from the MFI associated with the same pathogen class in the specimen wells to calculate an adjusted MFI for that pathogen class within the specimen. The adjusted MFI may be compared to a threshold for each indicator to determine whether the pathogen associated with that indicator is present in the patient specimen.

In various embodiments, the assay is a respiratory pathogen panel (RPP) or FilmArray Respiratory Panel (FA-RP) capable of detecting multiple pathogens associated with respiratory disease and may be used in conjunction with a second assay capable of detecting signs of one or more of the same pathogens detected by the RPP.

In another embodiment, the molecular assay includes PCR amplification and amplified nucleic acids associated with a pathogen can be detected in a subsequent step adapted for one of the following formats: 96-well plate, 384-well plate, individual tube, array card (for example, 384 wells) or array plate (for example, 2,688 wells). In one example, the 384-well format is capable of testing 8 patient specimens for the presence of 42 pathogens and the test requires 5 hours to determine whether a pathogen is detected in a patient sample, and may include the use of a QuantStudio 12K Flex Real-Time PCR System with TaqMan Array Card block where each reaction has a volume of 1 µL. In one example, the 2,688-well format is capable of testing triplicates of 24 patient specimens for the presence of 31 pathogens and the test requires 5 hours to determine whether a pathogen is detected in a patient sample, and may include the use of a QuantStudio 12K Flex Real-Time PCR System with OpenArray block where each reaction has a volume of 33 nL.

In yet another embodiment, the molecular assay is an automated multiplex real-time RT-PCR assay that receives a nasopharyngeal swab specimen and requires 20 minutes to determine whether a pathogen is detected in a patient sample, including the use of a Cobas® Liat® PCR System.

In another example, nucleic acids isolated from a patient specimen are processed for next-generation sequencing (NGS). The NGS panel may be a pathogen specific panel, which may include probes that target portions of the genome of the pathogen of interest. The NGS panel may be a host specific panel, for example, an RNA-seq human whole exome panel designed to sequence cDNA generated from human mRNA transcripts isolated from the patient sample.

Sequencing reads generated by NGS are processed by a bioinformatics pipeline. For an example of a bioinformatics pipeline adapted for pathogen detection, see U.S. prov. patent app. No. 62/978,067 "Systems and Methods for Detecting Viral DNA from Sequencing," filed Feb. 18, 2020 and incorporated by reference herein in its entirety. For an example of an engine adapted for detecting a host nucleic acid signature indicative of infection by a pathogen, see U.S. patent application Ser. No. 16/802,126 "Systems and Methods for Using Sequencing Data for Pathogen Detection," filed Feb. 26, 2020 and incorporated by reference herein in its entirety.

In various embodiments, the result of the assay includes additional information beyond the presence or absence of a pathogen, which may be included in the key subject features used to personalize the reporting of the pathogen detection results or make personalized testing result adjustments. For example, a PCR assay result may include a cycle threshold (Ct) value. In various embodiments, the patient is not required to go to a medical clinic or hospital for specimen collection. In various embodiments, the person collecting the specimen is not required to have medical training or experience. In various embodiments, a specimen collection kit is delivered to the patient.

In various embodiments, the assay may be a rapid assay designed to yield results within 5, 10, 15, 20, 25, or 30 minutes of processing the specimen. In various embodiments, the assay may be completed in a laboratory, hospital, physician office, urgent care setting, or in the patient's home.

At the time of the specimen collection, the patient may be experiencing symptoms caused by the infection or the patient may be asymptomatic. The pathogen detection may be an incidental finding from periodic surveillance testing, a routine physical examination, etc. Descriptions of symptoms, the lack of symptoms, or the circumstances of the test may be included in clinical data used to personalize the reporting of the pathogen detection results. The infection may be chronic or acute. In various embodiments, the assay or combination of assays may test for the presence of multiple pathogens (for example, a multiplexed assay). A multiplexed assay may reduce the chance of a false negative result determined by an assay that only detects the presence of one or a few types of pathogens. A combination of two or more assays may process a specimen, wherein each assay has a list of pathogens that can be detected by the assay and the two or more assays may share one or more detectable pathogens in common. For example, two or more assays that are each capable of detecting SARS-COV-2 may be used to process the same specimen. Clinical and/or molecular data associated with the patient and deemed relevant to the infection may be used to assist a physician in personalizing treatment for the patient and making other clinical decisions.

In one example, the patient may or may not have a liver function test result that indicates that the patient has liver failure (for example, PT, INR, albumin, etc.). An assay detects the presence of one or more pathogens commonly associated with liver failure (for example, hepatitis A, B, C, D, E, etc.). Any of the patient's liver function test results may be included in clinical data used to personalize the reporting of the pathogen detection results.

In one example, the patient has symptoms of meningitis and the assay detects the presence of one or more pathogens associated with meningitis. In other examples, the patient has symptoms of an infectious disease selected from one of HIV, Lyme, cholera, malaria, tuberculosis, measles, pertussis, STDs, antibiotic resistant bacteria (MRSA, *C. difficile*) and the assay detects the presence of one or more pathogens associated with such disease.

In one example, the patient has gastrointestinal symptoms (*Salmonella*, and the assay detects the presence of one or more pathogens associated with gastrointestinal symptoms.

In one example, the patient has pneumonia, a respiratory illness, and/or flu-like symptoms, or is asymptomatic and the assay detects the presence of one or more pathogens associated with flu-like symptoms. Pathogens associated with the symptoms may include SARS-COV-1, SARS-CoV-2, MERS-COV, Coronavirus HKU1, Coronavirus NL63, Coronavirus 229E, Coronavirus OC43, Influenza A, Influenza A H1, Influenza A H1-2009, Influenza A H1N1, Influenza A H3, Influenza B, Influenza C, Parainfluenza virus 1, Parainfluenza virus 2, Parainfluenza virus 3, Parainfluenza virus 4, Rhinovirus/Enterovirus, Adenovirus, Respiratory Syncytial Virus, Respiratory Syncytial Virus A, Respiratory Syncytial Virus B, Human Metapneumovirus, Bocavirus, Human Bocavirus, *Chlamydophila pneumoniae, Mycoplasma pneumoniae, Legionella pneumophila, Bordetella, Bordetella holmesii, Bordetella pertussis, Streptococcus pneumoniae, Coxiella burnetii, Staphylococcus aureus, Klebsiella pneumoniae, Moraxella catarrhalis, Haemophilus influenzae, Pneumocystis jirovecii*, Enterovirus D68, Epstein-Barr virus (EBV), Mumps, Measles, Cytomegalovirus, Human herpesvirus 6 (HHV-6), Varicella zoster virus (VZV), Parechovirus, etc.

Table 3 is a table of some respiratory pathogens. In various embodiments, the diagnostic test used to detect the presence of a pathogen may detect portions of a genetic sequence associated with the pathogen.

TABLE 3

| Target |
| --- |
| Adenovirus |
| MERS-CoV |
| SARS-CoV-1 |
| SARS-CoV-2 |
| Coronavirus 229E |
| Coronavirus HKU1 |
| Coronavirus NL63 |
| Coronavirus OC43 |
| Human Bocavirus |
| Human Metapneumo virus |
| Influenza A |
| Influenza A/H1 |
| Influenza A/H1-2009 |
| Influenza A/H3 |
| Influenza B |
| Influenza C |
| Parainfluenza virus 1 |

TABLE 3-continued

| Target |
| --- |
| Parainfluenza virus 2 |
| Parainfluenza virus 3 |
| Parainfluenza virus 4 |
| Respiratory Syncytial Virus A |
| Respiratory Syncytial Virus B |
| Rhinovirus/ Enterovirus* |

The status of each pathogen (for example, whether it is detected in the patient specimen or not), may be included in a report delivered to the physician and/or patient. The report may be delivered to the physician and/or patient automatically upon completion of at least one assay ordered for the patient, or at another point in the assay and assay analysis workflow. In various embodiments, the report is delivered within 1 to 2 days of the testing laboratory receiving the patient specimen. The status of a pathogen may include separate results from multiple assays and/or combined or summarized results from multiple assays. A relative amount or abundance of the pathogen detected may be included in the report. A Ct value associated with the detected pathogen may be included in the report.

One or more therapies that can be used to treat the infection and/or disease caused by the pathogen may be included in the report.

The report may also include personalized testing result adjustments. A likelihood that the patient will respond favorably to each therapy, based on clinical and molecular data associated with the patient, may be included in the report. The degree of disease severity (for example, asymptomatic, mild, moderate, severe, fatal, etc.) predicted for the patient, based on clinical and molecular data associated with the patient, may be included in the report. The likelihood that the patient is contagious and capable of transmitting the disease to another person, and a prediction of the number of days after the specimen was collected that the patient will be contagious, may be included in the report. The patient's predicted degree of susceptibility to future infections (for example, infection by the same strain of the same pathogen, a different strain of the same pathogen, a related pathogen, or an unrelated pathogen), based on clinical and molecular data associated with the patient, may be included in the report. Recommended measures for preventing transmission of the pathogen from the patient to another individual may be included in the report. Measures may include recommendations for the patient and for individuals living with and/or otherwise interacting with the patient. Measures may include quarantine, isolation, wearing personal protective equipment (for example, masks, goggles, safety glasses, disposable gown, shoe coverings, PAPR, etc.), maintaining physical distance, designating a bathroom for only the patient to use, etc.

In the event of a pathogen detected in a patient specimen, an alert may be sent (for example, through an API) instructing the patient's cell phone service provider to initiate contact tracing protocols, to provide the location history of the patient's cell phone to a health authority and/or to notify phones that have been in a location proximal to the patient's phone that the owners of the phones had a possible exposure to the pathogen. The patient's location history data may be deidentified to maintain patient privacy.

Key subject features used to make personalized testing result adjustments may include clinical and molecular data. Clinical data types used to predict the likelihood that a patient will respond favorably to a therapy, have a particular degree of severity of disease, be contagious, and/or be susceptible to future infections may include patient age, gender, race, other patient demographics, health conditions (including diabetes, cardiac disease, hypertension, body mass, asthma, autoimmune disorders, allergies, etc.), therapy response history, blood sugar level, etc.

Molecular data types used to predict the likelihood that a patient will respond favorably to a therapy, have a particular degree of severity of disease, be contagious, and/or be susceptible to future infections may include genomic data (variants, gene alleles, etc.), transcriptomic data (expression levels, transcript isoforms, etc.), immunological profiles, cytokine expression profiles, pathogen data, epigenomic data (methylation status, methylation profile, etc.), metabolomic data, proteomic data, additional-omic data types, various biomarkers, etc. Genomic data may include information related to genes, immunologic genes, for example, TLR7, innate immune system genes, HLA (MHC) genes (including HLA-A, HLA-B, HLA-C, HLA-E, HLA-F, HLA-G, HLA-DRA, HLA-DRB1, HLA-DQA1, HLA-DAB1, HLA-DPA1, HLA-DPB1, etc.), genes associated with chromosomes three and six, ABO blood type (for example the gene located on chromosome 9q34.2), PLEC, MUC6, TNS1, LARS, PARP4, SVIL, GAA, LTBP4, MUC20, PSME4, FLNB, REPIN1, INTS1, DOCK1, SMG6, PLXND1, PDCD6IP, GOT2, TCEA1, KARS1, GPS1, PSMB2, VPS72, genes that may be correlated with a cytokine expression profile or an immune response, genes correlated with clinical outcomes relevant to the infectious disease, etc. An immunological profile may include HLA, t-cell receptor, and/or b-cell receptor sequences detected in the patient and may further include a measured quantity of at least one detected sequence or information related to those quantities. Pathogen data may include genetic sequences detected in the patient specimen associated with the pathogen, pathogen strain, etc.

Patient data may be stored in a database. Aggregate patient data may be used to track current epidemics and predict future epidemics (for example, location, magnitude, severity, etc. of the epidemic). Aggregate patient data may be analyzed to determine associations between any collected clinical or molecular data observation and disease severity, therapy response, susceptibility to a disease, other clinical outcomes, etc. Aggregate patient data may be used to analyze genetic drift of the pathogen over time, associate a strain or pathogen with geographic location, assist in contact tracing, etc. Aggregate patient data may be delivered to a health authority, for example, a state or local health department.

ILLUSTRATIVE EMBODIMENTS

Described below are several non-limiting, exemplary embodiments of the systems and methods described herein.

1. A method performed by a clinical laboratory comprising:

a. receiving a specimen or image associated with a patient;

b. using at least one laboratory technology to examine the specimen or image;

c. obtaining an initial result from the examination of the specimen or image;

d. adjusting the initial result based on a clinomic profile of the patient; and e. issuing a report listing the adjusted result.

Illustrative embodiments related to the type of clinomic profile.

2. The method of embodiment 1, wherein the clinomic profile comprises the gender of the patient.

3. The method of embodiment 1, wherein the clinomic profile comprises the race of the patient.

4. The method of embodiment 1, wherein the clinomic profile comprises molecular information of the patient.

5. The method of embodiment 1, wherein the clinomic profile comprises genetic variant information of a specimen from the patient.

6. The method of embodiment 1, wherein the clinomic profile comprises transcriptome information of a specimen from the patient.

7. The method of embodiment 1, wherein the clinomic profile comprises genetic variant information and transcriptome information of at least one specimen from the patient.

8. The method of embodiment 1, wherein the clinomic profile comprises at least one feature derived from an image associated with the patient.

9. The method of embodiment 8, wherein the image associated with the patient is an image of the patient.

10. The method of embodiment 8, wherein the image associated with the patient is an image of a specimen of the patient.

11. The method of embodiment 1, wherein the clinomic profile comprises a prior result from the examination of a prior specimen associated with the patient.

Illustrative embodiments related to the source of the clinomic profile.

12. The method of embodiment 1, wherein at least a portion of the clinomic profile is obtained from a structured clinomic data repository.

13. The method of embodiment 1, wherein at least a portion of the clinomic profile is obtained from a source patient dataset.

14. The method of embodiment 1, wherein at least a portion of the clinomic profile is obtained from a structured patient dataset.

15. The method of embodiment 1, wherein the clinomic profile is generated by:

a. receiving a plurality of source records and a structured patient dataset for the patient;

b. extracting a plurality of data elements from the source records; and c. storing the extracted data elements and the structured patient dataset in a clinomic data repository.

16. The method of embodiment 15, wherein the plurality of source records comprises a genetic test report.

17. The method of embodiment 16, wherein the plurality of data elements comprises a genomic variant data element.

18. The method of embodiment 15, wherein the plurality of source records comprises a metabolomic test report.

19. The method of embodiment 18, wherein the plurality of data elements comprises a metabolomic data element.

20. The method of embodiment 15, wherein the plurality of source records comprises a transcriptome test report.

21. The method of embodiment 20, wherein the plurality of data elements comprises a transcriptome data element.

22. The method of embodiment 21, wherein the transcriptome data element comprises an expression level.

23. The method of embodiment 21, wherein the transcriptome data element comprises an over-expression determination.

24. The method of embodiment 21, wherein the transcriptome data element comprises an under-expression determination.

Illustrative embodiments related to the type of examination.

25. The method of embodiment 1, wherein the examination is a complete blood count.

26. The method of embodiment 1, wherein the examination is a red blood cell count.

27. The method of embodiment 1, wherein the examination is a hemoglobin count.

28. The method of embodiment 1, wherein the examination is a white blood cell count.

29. The method of embodiment 1, wherein the examination is a platelet count.

30. The method of embodiment 1, wherein the examination is a hemoglobin A1C examination.

31. The method of embodiment 30, wherein the initial result is between 5.7 and 6.4 percent.

32. The method of embodiment 31, wherein the adjusted result is below 5.7 percent.

33. The method of embodiment 31, wherein the adjusted result is above 6.4 percent.

34. The method of embodiment 30, wherein the initial result is "normal" and the adjusted result is "prediabetes".

35. The method of embodiment 30, wherein the initial result is "normal" and the adjusted result is "diabetes".

36. The method of embodiment 30, wherein the initial result is "prediabetes" and the adjusted result is "normal".

37. The method of embodiment 30, wherein the initial result is "prediabetes" and the adjusted result is "diabetes".

38. The method of embodiment 30, wherein the initial result is "diabetes" and the adjusted result is "prediabetes".

39. The method of embodiment 30, wherein the initial result is "diabetes" and the adjusted result is "normal".

40. The method of embodiment 30, wherein the initial result is adjusted by adjusting one of the following thresholds: a threshold of less than 5.7 percent for "normal"; a threshold of between 5.7 and 6.4 percent for "prediabetes"; and a threshold of 6.5 percent or above for "diabetes".

41. The method of any of embodiments 31 to 40, wherein the clinomic profile comprises a genomic variant data element.

Illustrative embodiments related to adjustment of the initial test result.

42. The method of embodiment 1, wherein the initial result is adjusted by increasing a quantity of the initial result.

43. The method of embodiment 1, wherein the initial result is adjusted by decreasing a quantity of the initial result.

44. The method of embodiment 1, wherein the initial result is adjusted by increasing a percentage value of the initial result.

45. The method of embodiment 1, wherein the initial result is adjusted by decreasing a percentage value of the initial result.

46. The method of embodiment 1, wherein the initial result is adjusted by adjusting a threshold associated with the examination.

47. The method of embodiment 46, wherein the threshold is a detected/not detected threshold.

Illustrative embodiments related to the type of equipment used in the lab testing.

48. The method of embodiment 1, wherein the laboratory technology used to conduct the examination comprises a nucleic acid analyzer.

49. The method of embodiment 1, wherein the laboratory technology used to conduct the examination comprises an enzyme-linked immunosorbent assay.

50. The method of embodiment 1, wherein the laboratory technology used to conduct the examination comprises immunohistochemistry technology.

51. The method of embodiment 1, wherein the laboratory technology used to conduct the examination comprises a cholesterol measuring device.

Illustrative embodiments related to disease subtype.

52. The method of embodiment 1, wherein the adjusted result reflects a diagnosis related to cancer.

53. The method of embodiment 1, wherein the adjusted result reflects a diagnosis related to infectious disease.

54. The method of embodiment 1, wherein the adjusted result reflects a diagnosis related to diabetes.

55. The method of embodiment 1, wherein the adjusted result reflects a diagnosis related to depression.

56. The method of embodiment 1, wherein the adjusted result reflects a diagnosis related to cholesterol level.

57. The method of embodiment 1, wherein the adjusted result reflects a diagnosis related to a cardiac condition.

58. The method of embodiment 1, wherein the adjusted result reflects a diagnosis related to an immune condition.

Illustrative embodiments related to the type of specimen.

59. The method of embodiment 1, wherein the specimen is a blood specimen.

60. The method of embodiment 1, wherein the specimen is a tissue specimen.

61. The method of embodiment 1, wherein the specimen is a spinal fluid specimen.

62. The method of embodiment 1, wherein the specimen is a bone marrow specimen.

63. The method of embodiment 1, wherein the specimen is a solid tumor specimen.

64. The method of embodiment 1, wherein the specimen is circulating tumor DNA.

65. The method of embodiment 1, wherein the specimen is cell-free DNA.

66. The method of embodiment 1, wherein the specimen is plasma.

67. The method of embodiment 1, wherein the specimen is buffy coat.

68. The method of embodiment 1, wherein the image is a pathology image.

69. The method of embodiment 1, wherein the image is a radiology image.

70. The method of embodiment 1, wherein the image is a CT image.

Illustrative embodiments related to providing the revised result.

71. The method of embodiment 1, further comprising entering the revised result into an electronic health record.

72. The method of embodiment 1, wherein the report listing the adjusted result is issued to a health care professional.

73. The method of embodiment 1, further comprising providing the adjusted result to a group of expert clinicians for joint review.

74. The method of embodiment 1, wherein the issued report also includes a smart output associated with the patient.

75. The method of embodiment 1, wherein the issued report also includes a smart output associated with the adjusted result.

Illustrative embodiments related to providing a smart output.

76. The method of embodiment 1, wherein the issued report also includes a smart output associated with the initial result.

77. The method of any of embodiments 74 or 75, wherein the smart output comprises a personalized threshold of evaluation specific to the patient.

78. The method of any of embodiments 74 or 75, wherein the smart output comprises a representation of clinomic profiles from a cohort of other patients similar to the patient.

79. The method of any of embodiments 74 or 75, wherein the smart output comprises a gene-drug interaction associated with genetic variant information of the patient.

80. The method of any of embodiments 74 or 75, wherein the smart output comprises a gene-drug interaction associated with genetic variant information of the patient.

81. The method of any of embodiments 74 or 75, wherein the smart output comprises treatment information associated with the revised laboratory diagnostic testing result.

82. The method of any of embodiments 74 or 75, wherein the smart output comprises treatment information associated with the clinomic profile of the patient.

Illustrative embodiments related to specific types of laboratory technology used to conduct the examination.

83. The method of embodiment 1, wherein the laboratory technology used to conduct the examination of the image comprises radiological scanning equipment.

84. The method of embodiment 1, wherein the laboratory technology used to conduct the examination of the specimen comprises a PCR machine.

85. The method of embodiment 1, wherein the laboratory technology used to conduct the examination of the specimen comprises a CRISPR kit.

A clinical laboratory illustrative embodiment.

86. A clinical laboratory comprising:

a. one or more laboratory technologies;

b. a computer system in operative communication with a structured clinomic data repository and one or more analysis modules, each analysis module comprising an input to receive an initial result from an examination of a specimen or image of a patient using one or more of the laboratory technologies and an output to provide an adjusted result based on the initial result from the examination and a clinomic profile of the patient stored in the structured clinomic data repository.

87. The clinical laboratory of embodiment 86, wherein the computer system is in operative communication with a source patient dataset.

88. The clinical laboratory of embodiment 86, wherein the computer system is in operative communication with a structured patient dataset.

89. The clinical laboratory of embodiment 86, wherein a smart output is provided by at least one of the analysis modules.

90. The clinical laboratory of embodiment 89, wherein the smart output is associated with the initial result.

91. The clinical laboratory of embodiment 89, wherein the smart output comprises a personalized threshold of evaluation specific to the patient.

92. The clinical laboratory of embodiment 72, wherein the smart output comprises a representation of clinomic profiles from a cohort of other patients similar to the patient.

93. The clinical laboratory of embodiment 72, wherein the smart output comprises a gene-drug interaction associated with genetic variant information of the patient.

94. The clinical laboratory of embodiment 72, wherein the smart output comprises a gene-drug interaction associated with genetic variant information of the patient.

95. The clinical laboratory of embodiment 72, wherein the smart output comprises treatment information associated with the revised laboratory diagnostic testing result.

96. The clinical laboratory of embodiment 72, wherein the smart output comprises treatment information associated with the clinomic profile of the patient.

97. The clinical laboratory of embodiment 86, wherein the laboratory technology comprises a nucleic acid analyzer.

98. The clinical laboratory of embodiment 86, wherein the laboratory technology comprises an enzyme-linked immunosorbent assay.

99. The clinical laboratory of embodiment 86, wherein the laboratory technology comprises an immunohistochemistry stainer.

100. The clinical laboratory of embodiment 86, wherein the laboratory technology comprises a cholesterol measuring device.

101. The clinical laboratory of embodiment 86, wherein the laboratory technology comprises a magnetic resonance imaging device.

102. The clinical laboratory of embodiment 86, wherein the laboratory technology comprises an ultrasound device.

103. The clinical laboratory of embodiment 86, wherein the laboratory technology comprises an echocardiograph machine.

104. The clinical laboratory of embodiment 86, wherein the laboratory technology comprises a CT imaging system.

105. The clinical laboratory of embodiment 86, wherein the laboratory technology comprises a CRISPR kit.

106. The clinical laboratory of embodiment 86, wherein the laboratory technology comprises a bioinformatics pipeline.

107. The clinical laboratory of embodiment 86, wherein the laboratory technology comprises radiological scanning equipment.

108. The clinical laboratory of embodiment 86, wherein the laboratory technology comprises a PCR machine.

CONCLUSION

In the foregoing specification, implementations of the disclosure have been described with reference to specific example implementations thereof. It will be evident that various modifications may be made thereto without departing from the broader spirit and scope of implementations of the disclosure as set forth in the following claims. The specification and drawings are, accordingly, to be regarded in an illustrative sense rather than a restrictive sense.

While the invention may be susceptible to various modifications and alternative forms, specific embodiments have been shown by way of example in the drawings and have been described in detail herein. However, it should be understood that the invention is not intended to be limited to the particular forms disclosed. Thus, the invention is to cover all modifications, equivalents, and alternatives falling within the spirit and scope of the invention as defined by the following appended claims.

What is claimed is:

1. A computer-implemented method for subject monitoring, the method comprising:

obtaining, by a computing system, an initial laboratory result, comprising a measurement of a first characteristic, from an examination of a specimen or an image associated with a subject, wherein at least one laboratory technology is used to determine the initial laboratory result;

obtaining, by the computing system, a first clinomic profile of the subject from a structured clinomic data repository;

comparing, by the computing system, the first clinomic profile with each clinomic profile in the structured clinomic data repository using a subject similarity metric that quantifies a degree to which each clinomic profile in the structured clinomic data repository is similar to the first clinomic profile, wherein the structured clinomic data repository comprises 1000 or more clinomic profiles representing 1000 or more subjects, thereby identifying a subset of clinomic profiles that are similar to the first clinomic profile;

identifying, by the computing system, a second characteristic common to the subset of clinomic profiles;

adjusting a threshold of interpretation, between at least one disease state and a normal state, of the measurement of the first characteristic in the initial laboratory result based on the second characteristic;

issuing, over a computer network, a structured report listing the initial laboratory result and the adjusted threshold of interpretation of the measurement of the first characteristic in the initial laboratory result;

originating, by the computing system, on the basis of the adjusted threshold of interpretation of the measurement of the first characteristic in the initial laboratory result, a request to perform an additional assay on the subject; and obtaining, by the computing system, responsive to the request, a determination that the additional assay has been performed on the subject, thereby performing subject monitoring.

2. The computer-implemented method of claim 1, wherein the first clinomic profile comprises a gender of the subject.

3. The computer-implemented method of claim 1, wherein the first clinomic profile comprises a race of the subject.

4. The computer-implemented method of claim 1, wherein the first clinomic profile comprises molecular information of the subject.

5. The computer-implemented method of claim 1, wherein the first clinomic profile comprises genetic variant information of a specimen from the subject.

6. The computer-implemented method of claim 1, wherein the first clinomic profile comprises transcriptome information of a specimen from the subject.

7. The computer-implemented method of claim 1, wherein the first clinomic profile comprises genetic variant information and transcriptome information of at least one specimen from the subject.

8. The computer-implemented method of claim 1, wherein the first clinomic profile comprises at least one feature derived from an image associated with the subject.

9. The computer-implemented method of claim 8, wherein the image associated with the subject is an image of the subject.

10. The computer-implemented method of claim 8, wherein the image associated with the subject is an image of a specimen of the subject.

11. The computer-implemented method of claim 1, wherein the first clinomic profile comprises a prior result from an examination of a prior specimen associated with the subject.

12. The computer-implemented method of claim 1, wherein the obtaining, by the computer system, the first clinomic profile comprises:

a. receiving, by the computing system, a plurality of source records and a structured subject dataset for the subject;

b. extracting, by the computing system, a plurality of data elements from the plurality of source records; and c. storing, by the computing system, the extracted data elements and the structured subject dataset in the clinomic data repository as the first clinomic profile.

13. The computer-implemented method of claim 12, wherein the plurality of source records comprises a structured genetic test report.

14. The computer-implemented method of claim 13, wherein the plurality of data elements comprises a genomic variant data element.

15. The computer-implemented method of claim 12, wherein the plurality of source records comprises a structured metabolomic test report.

16. The computer-implemented method of claim 15, wherein the plurality of data elements comprises a metabolomic data element.

17. The computer-implemented method of claim 12, wherein the plurality of source records comprises a structured transcriptome test report.

18. The computer-implemented method of claim 17, wherein the plurality of data elements comprises a transcriptome data element.

19. The computer-implemented method of claim 18, wherein the transcriptome data element comprises an expression level.

20. The computer-implemented method of claim 18, wherein the transcriptome data element comprises an over-expression determination.

21. The computer-implemented method of claim 18, wherein the transcriptome data element comprises an under-expression determination.

22. The computer-implemented method of claim 1, wherein the examination is a complete blood count.

23. The computer-implemented method of claim 1, wherein the examination is a red blood cell count.

24. The computer-implemented method of claim 1, wherein the examination is a hemoglobin count.

25. The computer-implemented method of claim 1, wherein the examination is a white blood cell count.

26. The computer-implemented method of claim 1, wherein the examination is a platelet count.

27. The computer-implemented method of claim 1, wherein the examination is a hemoglobin A1C examination and the first characteristic is A1C.

28. The computer-implemented method of claim 27, wherein the measurement of the first characteristic in the initial laboratory result is between 5.7 and 6.4 percent A1C.

29. The computer-implemented method of claim 28, wherein the adjusted threshold of interpretation of the measurement of the first characteristic is a single value that is less than 5.7 percent A1C, and wherein, when the measurement of the first characteristic in the initial laboratory result indicates that the hemoglobin A1C is below the single value, the subject is diagnosed as normal.

30. The computer-implemented method of claim 28, wherein the adjusted threshold of interpretation of the measurement of the first characteristic is above 6.4 percent A1C and wherein, when the of the measurement of the first characteristic in the initial laboratory result indicates that the hemoglobin A1C is above the threshold of interpretation, the subject is diagnosed as diabetic.

31. The computer-implemented method of claim 27, wherein the measurement of the first characteristic in the initial laboratory result for the subject indicates the subject is normal, and the adjusted threshold of interpretation of the measurement of the first characteristic in the initial laboratory result indicates the subject is prediabetic.

32. The computer-implemented method of claim 31, wherein the first clinomic profile comprises a genomic variant data element.

33. The computer-implemented method of claim 27, wherein the measurement of the first characteristic in the initial laboratory result for the subject is normal, and the adjusted threshold of interpretation of the measurement of the first characteristic in the initial laboratory result indicates the subject is diabetic.

34. The computer-implemented method of claim 27, wherein the measurement of the first characteristic in the initial laboratory result for the subject indicates the subject is prediabetic, and the adjusted threshold of interpretation of the measurement of the first characteristic in the initial laboratory result indicates the subject is normal.

35. The computer-implemented method of claim 27, wherein the measurement of the first characteristic in the initial laboratory result for the subject indicates the subject is prediabetic, and the adjusted threshold of interpretation of the measurement of the first characteristic in the initial laboratory result indicates the subject is diabetic.

36. The computer-implemented method of claim 27, wherein the measurement of the first characteristic in the initial laboratory result for the subject indicates the subject is diabetic, and the adjusted threshold of interpretation of the measurement of the first characteristic in the initial laboratory result indicates the subject is prediabetic.

37. The computer-implemented method of claim 27, wherein the measurement of the first characteristic in the initial laboratory result for the subject indicates the subject is diabetic, and the adjusted threshold of interpretation of the measurement of the first characteristic in the initial laboratory result indicates the subject is normal.

38. The computer-implemented method of claim 27, wherein the first characteristic is A1C and the threshold of interpretation of the measurement of the first characteristic in the initial laboratory result is adjusted to less than 5.7 percent A1C for "normal", between 5.7 and 6.4 percent A1C for "prediabetes", or 6.5 percent A1C or above for "diabetes".

39. The computer-implemented method of claim 1, wherein the adjusting the threshold of interpretation of the measurement of the first characteristic of the initial laboratory result comprises increasing a quantity of the threshold of interpretation of the measurement of the first characteristic of the initial laboratory result.

40. The computer-implemented method of claim 1, wherein the adjusting the threshold of interpretation of the measurement of the first characteristic of the initial laboratory result comprises decreasing a quantity of the threshold of interpretation of the measurement of the first characteristic of the initial laboratory result.

41. The computer-implemented method of claim 1, wherein the threshold of interpretation of the measurement of the first characteristic of the initial laboratory result comprises increasing a percentage value of the threshold of interpretation of the measurement of the first characteristic of the initial laboratory result.

42. The computer-implemented method of claim 1, wherein the threshold of interpretation of the measurement of the first characteristic of the initial laboratory result comprises decreasing a percentage value of the threshold of interpretation of the measurement of the first characteristic of the initial laboratory result.

43. The computer-implemented method of claim 1, wherein the threshold of interpretation of the measurement of the first characteristic of the initial laboratory result is a detected/not detected threshold.

44. The computer-implemented method of claim 1, wherein the adjusted threshold of interpretation of the measurement of the first characteristic of the initial laboratory result reflects a diagnosis related to cancer for the subject.

45. The computer-implemented method of claim 1, wherein the adjusted threshold of interpretation of the measurement of the first characteristic of the initial laboratory result reflects a diagnosis related to infectious disease for the subject.

46. The computer-implemented method of claim 1, wherein the adjusted threshold of interpretation of the measurement of the first characteristic of the initial laboratory result reflects a diagnosis related to diabetes for the subject.

47. The computer-implemented method of claim 1, wherein the adjusted threshold of interpretation of the measurement of the first characteristic of the initial laboratory result reflects a diagnosis related to depression for the subject.

48. The computer-implemented method of claim 1, wherein the adjusted threshold of interpretation of the measurement of the first characteristic of the initial laboratory result reflects a diagnosis related to cholesterol level for the subject.

49. The computer-implemented method of claim 1, wherein the adjusted threshold of interpretation of the measurement of the first characteristic of the initial laboratory result reflects a diagnosis related to a cardiac condition for the subject.

50. The computer-implemented method of claim 1, wherein the adjusted threshold of interpretation of the measurement of the first characteristic of the initial laboratory result reflects a diagnosis related to an immune condition for the subject.

51. The computer-implemented method of claim 1, wherein the initial laboratory result is from the examination of the specimen and wherein the specimen is a blood specimen.

52. The computer-implemented method of claim 1, wherein the initial laboratory result is from the examination of the specimen and wherein the specimen is a tissue specimen.

53. The computer-implemented method of claim 1, wherein the initial laboratory result is from the examination of the specimen and wherein the specimen is a spinal fluid specimen.

54. The computer-implemented method of claim 1, wherein the initial laboratory result is from the examination of the specimen and wherein the specimen is a bone marrow specimen.

55. The computer-implemented method of claim 1, wherein the initial laboratory result is from the examination of the specimen and wherein the specimen is a solid tumor specimen.

56. The computer-implemented method of claim 1, wherein the initial laboratory result is from the examination of the specimen and wherein the specimen is circulating tumor DNA.

57. The computer-implemented method of claim 1, wherein the initial laboratory result is from the examination of the specimen and wherein the specimen is cell-free DNA.

58. The computer-implemented method of claim 1, wherein the initial laboratory result is from the examination of the specimen and wherein the specimen is plasma.

59. The computer-implemented method of claim 1, wherein the initial laboratory result is from the examination of the specimen and wherein the specimen is buffy coat.

60. The computer-implemented method of claim 1, wherein the initial laboratory result is from the image and wherein the image is a pathology image.

61. The computer-implemented method of claim 1, wherein the initial laboratory result is from the image and wherein the image is a radiology image.

62. The computer-implemented method of claim 1, wherein the initial laboratory result is from the image and wherein the image is a CT image.

63. The computer-implemented method of claim 1, the method further comprising entering, using the computer system, the adjusted threshold of interpretation of the measurement of the first characteristic of the initial laboratory result into an electronic health record associated with the subject.

64. The computer-implemented method of claim 1, wherein the issuing communicates the structured report to a health care professional across a computer network.

65. The computer-implemented method of claim 1, wherein the issuing communicates the structured report to a group of expert clinicians across a computer network.

66. The computer-implemented method of claim 1, wherein the structured report further comprises a diagnosis of the subject.

67. The computer-implemented method of claim 1, wherein the structured report further comprises a treatment for the subject.

68. The computer-implemented method of claim 1, wherein the structured report further comprises a representation of the subset of clinomic profiles.

69. The computer-implemented method of claim 1, wherein the structured report further comprises a gene-drug interaction associated with genetic variant information of the subject.

70. The computer-implemented method of claim 67, wherein the structured report further comprises a gene-drug interaction associated with genetic variant information of the specimen from the subject.

71. The computer-implemented method of claim 1, wherein the structured clinomic data repository comprises 100,000 or more clinomic profiles representing 100,000 or more subjects.

72. The computer-implemented method of claim 1, wherein the structured clinomic data repository comprises $1\times10^6$ or more clinomic profiles representing $1\times10^6$ or more subjects.

73. The computer-implemented method of claim 1, wherein the issuing comprises issuing the structured report to the subject or a medical practitioner associated with the subject over a computer network, the structured report identifies a treatment or therapy for a condition afflicting the subject, and the method further comprises receiving confirmation, over the computer network that the subject has taken the treatment or therapy for the condition responsive to the structured report.

74. The computer-implemented method of claim 73, wherein the condition is cancer.

75. The computer-implemented method of claim 1, the method further comprising using an anonymizer module to anonymize each clinomic profile in the plurality of clinomic profiles.

76. The computer-implemented method of claim 1, the method further comprising radially displaying, through an interactive software interface, each respective clinomic profile in the subset of clinomic profiles with respect to the first clinomic profile as a function of a value of the subject similarity metric between the respective clinomic profile and the first clinomic profile.

77. The computer-implemented method of claim 76, the method further comprising obtaining, through the interactive software interface, selection of one or more clinomic profiles to retain in the subset of clinomic profiles.

78. The computer-implemented method of claim 1, wherein the additional assay is a blood test.

79. The computer-implemented method of claim 1, wherein the additional assay is an imaging test.

80. The computer-implemented method of claim 1, wherein the additional assay is an accelerated screening test.

81. The computer-implemented method of claim 80, wherein the accelerated screening test is a cholesterol test, a blood glucose test, a blood count test, a prothrombin time blood test, a metabolic panel blood test, a lipid panel blood test, or a liver panel blood test.

82. A computer-implemented method for subject monitoring, the method comprising:

obtaining, by a computing system, an initial laboratory result, comprising a measurement of a first characteristic, from an examination of a specimen or an image associated with a subject, wherein at least one laboratory technology is used to determine the initial laboratory result;

obtaining, by the computing system, a first clinomic profile of the subject from a structured clinomic data repository;

comparing, by the computing system, the first clinomic profile with each clinomic profile in the structured clinomic data repository using a subject similarity metric that quantifies a degree to which each clinomic profile in the structured clinomic data repository is similar to the first clinomic profile, wherein the structured clinomic data repository comprises 1000 or more clinomic profiles representing 1000 or more subjects, thereby identifying a subset of clinomic profiles that are similar to the first clinomic profile;

identifying, by the computing system, a second characteristic common to the subset of clinomic profiles;

adjusting a threshold of interpretation, between at least one disease state and a normal state, of the measurement of the first characteristic in the initial laboratory result based on the second characteristic;

issuing a structured report listing the initial laboratory result and the adjusted threshold of interpretation of the measurement of the first characteristic in the initial laboratory result;

originating, by the computing system, on the basis of the adjusted threshold of interpretation of the measurement of the first characteristic in the initial laboratory result, a request to perform an additional assay on the subject; and obtaining, by the computing system, responsive to the request, a determination that the additional assay has been performed on the subject, thereby performing subject monitoring.

* * * * *